US 7,740,649 B2

(12) United States Patent
Mosca et al.

(10) Patent No.: US 7,740,649 B2
(45) Date of Patent: Jun. 22, 2010

(54) BONE PLATE SYSTEM AND METHODS

(75) Inventors: Lawrence Mosca, Marquette, MI (US); Matthew Peter Gephart, Marquette, MI (US); Brian Janowski, Marquette, MI (US); Brad Fredin, Ishpeming, MI (US); Francis Korhonen, Negaunee, MI (US); Matthew N. Songer, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 529 days.

(21) Appl. No.: 10/973,891

(22) Filed: Oct. 26, 2004

(65) Prior Publication Data
US 2005/0192577 A1 Sep. 1, 2005

Related U.S. Application Data

(60) Provisional application No. 60/548,140, filed on Feb. 26, 2004.

(51) Int. Cl.
*A61B 17/80* (2006.01)
(52) U.S. Cl. ........................................ 606/289; 606/280
(58) Field of Classification Search .............. 606/69–71
See application file for complete search history.

(56) References Cited
U.S. PATENT DOCUMENTS

| 434,503 A | 8/1890 | Corry |
| 556,642 A | 3/1896 | Reessing |
| 807,396 A | 12/1905 | Raveh |

(Continued)

FOREIGN PATENT DOCUMENTS

DE 251246 12/1911

(Continued)

OTHER PUBLICATIONS

Chang, J.H., Chang, G.L., Hsu, A.T. Kinematic Study of Cervical Vertebrae Adjacent to Fixation Procedures. *Institute of Biomedical Engineering*, Natl Cheng Kung University, Tainawn, Taiwan, R.O.C.

(Continued)

*Primary Examiner*—Thomas C Barrett
*Assistant Examiner*—Nicholas Woodall
(74) *Attorney, Agent, or Firm*—Fitch, Even, Tabin & Flannery

(57) ABSTRACT

Bone plate systems and anchor retainers are provided for use in surgical implants and bone repair. In a preferred form, the bone plate may include bores for receiving the bone anchors, and the bores may permit and define a path of translation or shifting of the bone anchors relative to the bone plate. The anchor retainers may be held in the bores to prevent back-out of the bone anchors. Once the anchor member is seated within the bone plate, the retainer may rest over a top surface of the anchor member so the anchor member is impeded from backing out of the bone plate. The retainer may expand or change shape to permit an anchor member to be driven through the retainer and may contract once an anchor member has been seated within the plate. In addition, a tool for insertion or extraction of the bone anchors is provided.

17 Claims, 47 Drawing Sheets

U.S. PATENT DOCUMENTS

| | | |
|---|---|---|
| 872,897 A | 12/1907 | Chapman et al. |
| 951,680 A | 3/1910 | Center |
| 1,084,680 A | 1/1914 | Wegener |
| 1,385,780 A | 7/1921 | Dodds |
| 1,409,157 A | 3/1922 | Dodds |
| 1,907,506 A | 5/1933 | Coburn |
| 1,980,336 A | 11/1934 | Hoagland |
| 3,100,516 A | 8/1963 | Naab |
| 3,244,170 A | 4/1966 | McElvenny |
| 3,596,656 A | 8/1971 | Kaute |
| 3,695,259 A | 10/1972 | Yost |
| 3,741,205 A | 6/1973 | Markolf et al. |
| 3,842,825 A | 10/1974 | Wagner |
| RE28,841 E | 6/1976 | Allgower et al. |
| 4,003,376 A | 1/1977 | McKay et al. |
| 4,037,980 A | 7/1977 | Haentjens |
| 4,113,227 A | 9/1978 | Cigliano |
| 4,338,921 A | 7/1982 | Harder et al. |
| RE31,628 E | 7/1984 | Allgower et al. |
| 4,484,570 A | 11/1984 | Sutter et al. |
| 4,488,543 A | 12/1984 | Tornier |
| 4,503,848 A | 3/1985 | Caspar et al. |
| 4,524,765 A * | 6/1985 | de Zbikowski .............. 606/69 |
| 4,762,122 A | 8/1988 | Slocum |
| 4,794,918 A | 1/1989 | Wolter |
| 4,943,292 A | 7/1990 | Foux |
| 4,957,497 A | 9/1990 | Hoogland et al. |
| 4,964,403 A | 10/1990 | Karas et al. |
| 5,002,544 A | 3/1991 | Klaue et al. |
| 5,041,113 A | 8/1991 | Biedermann et al. |
| 5,053,036 A | 10/1991 | Perren et al. |
| 5,057,111 A | 10/1991 | Park |
| 5,085,660 A | 2/1992 | Lin |
| 5,108,395 A | 4/1992 | Laurain |
| 5,127,914 A | 7/1992 | Calderale et al. |
| 5,129,899 A | 7/1992 | Small et al. |
| 5,147,361 A | 9/1992 | Ojima et al. |
| 5,151,103 A | 9/1992 | Tepic et al. |
| 5,180,381 A | 1/1993 | Aust et al. |
| 5,261,910 A | 11/1993 | Warden et al. |
| 5,269,784 A | 12/1993 | Mast |
| 5,275,601 A | 1/1994 | Gogolewski et al. |
| 5,324,290 A | 6/1994 | Zdeblick et al. |
| 5,326,206 A | 7/1994 | Moore |
| 5,364,399 A | 11/1994 | Lowery |
| 5,380,323 A | 1/1995 | Howland |
| 5,382,248 A | 1/1995 | Jacobson et al. |
| 5,397,363 A | 3/1995 | Gelbard |
| 5,423,826 A | 6/1995 | Coates et al. |
| 5,478,342 A | 12/1995 | Kohrs |
| 5,486,176 A | 1/1996 | Hildebrand et al. |
| 5,501,684 A | 3/1996 | Schlapfer et al. |
| 5,520,690 A | 5/1996 | Errico et al. |
| 5,527,311 A | 6/1996 | Procter et al. |
| 5,531,746 A | 7/1996 | Errico et al. |
| 5,534,032 A | 7/1996 | Hodorek |
| 5,549,612 A | 8/1996 | Yapp et al. |
| 5,569,251 A * | 10/1996 | Baker et al. .............. 606/69 |
| 5,571,109 A | 11/1996 | Bertagnoli |
| 5,578,034 A | 11/1996 | Estes |
| 5,601,553 A | 2/1997 | Trebing et al. |
| 5,603,713 A | 2/1997 | Aust et al. |
| 5,607,426 A | 3/1997 | Ralph et al. |
| 5,607,428 A | 3/1997 | Lin |
| 5,616,144 A | 4/1997 | Yapp et al. |
| 5,620,443 A | 4/1997 | Gertzbein et al. |
| 5,643,265 A | 7/1997 | Errico et al. |
| 5,647,872 A | 7/1997 | Gilbert et al. |
| 5,651,651 A | 7/1997 | Spencer |
| 5,653,708 A | 8/1997 | Howland |
| 5,676,666 A | 10/1997 | Oxland et al. |
| 5,676,703 A | 10/1997 | Gelbard |
| 5,681,311 A | 10/1997 | Foley et al. |
| 5,681,312 A | 10/1997 | Yuan et al. |
| 5,709,686 A | 1/1998 | Talos et al. |
| 5,713,900 A | 2/1998 | Benzel et al. |
| 5,725,588 A | 3/1998 | Errico et al. |
| 5,735,850 A | 4/1998 | Baumgartner et al. |
| 5,735,853 A | 4/1998 | Olerud |
| 5,735,899 A | 4/1998 | Schwartz et al. |
| 5,741,258 A | 4/1998 | Klaue et al. |
| 5,766,254 A | 6/1998 | Gelbard |
| 5,797,912 A | 8/1998 | Runciman et al. |
| 5,800,433 A | 9/1998 | Benzel et al. |
| 5,810,823 A | 9/1998 | Klaue et al. |
| 5,840,078 A | 11/1998 | Yerys |
| 5,843,082 A | 12/1998 | Yuan et al. |
| 5,876,402 A | 3/1999 | Errico et al. |
| 5,879,389 A | 3/1999 | Koshino |
| 5,888,221 A | 3/1999 | Gelbard |
| 5,904,683 A | 5/1999 | Pohndorf et al. |
| 5,951,558 A | 9/1999 | Fiz |
| 5,954,722 A | 9/1999 | Bono |
| 5,976,141 A | 11/1999 | Haag et al. |
| 6,017,345 A | 1/2000 | Richelsoph |
| 6,022,350 A | 2/2000 | Ganem |
| 6,030,389 A | 2/2000 | Wagner et al. |
| 6,036,693 A | 3/2000 | Yuan et al. |
| 6,129,730 A | 10/2000 | Bono et al. |
| 6,139,550 A | 10/2000 | Michelson |
| 6,152,927 A | 11/2000 | Farris et al. |
| 6,159,213 A | 12/2000 | Rogozinski |
| 6,183,476 B1 | 2/2001 | Gerhardt et al. |
| 6,193,720 B1 | 2/2001 | Yuan et al. |
| 6,193,721 B1 | 2/2001 | Michelson |
| 6,214,005 B1 | 4/2001 | Benzel et al. |
| 6,224,602 B1 | 5/2001 | Hayes |
| 6,228,085 B1 | 5/2001 | Theken et al. |
| 6,235,032 B1 | 5/2001 | Linkl |
| 6,235,033 B1 | 5/2001 | Brace et al. |
| 6,235,034 B1 | 5/2001 | Bray |
| 6,241,731 B1 | 6/2001 | Fiz |
| 6,254,603 B1 | 7/2001 | Gertzbein et al. |
| 6,257,593 B1 | 7/2001 | White |
| 6,258,089 B1 | 7/2001 | Campbell et al. |
| 6,261,042 B1 | 7/2001 | Pratt |
| 6,261,291 B1 | 7/2001 | Talaber et al. |
| 6,273,889 B1 | 8/2001 | Richelsoph |
| 6,290,703 B1 | 9/2001 | Ganem |
| 6,293,949 B1 | 9/2001 | Justis et al. |
| 6,306,136 B1 | 10/2001 | Baccelli |
| 6,306,139 B1 | 10/2001 | Fuentes |
| 6,328,738 B1 | 12/2001 | Suddaby |
| 6,331,179 B1 | 12/2001 | Fried et al. |
| 6,332,887 B1 | 12/2001 | Knox |
| 6,335,034 B1 | 1/2002 | Drizen et al. |
| 6,342,055 B1 | 1/2002 | Eisermann et al. |
| 6,342,057 B1 | 1/2002 | Brace et al. |
| 6,361,537 B1 | 3/2002 | Anderson |
| 6,379,364 B1 | 4/2002 | Brace et al. |
| 6,381,806 B1 | 5/2002 | Stanesic et al. |
| 6,383,186 B1 | 5/2002 | Michelson |
| 6,391,030 B1 | 5/2002 | Wagner et al. |
| 6,398,783 B1 | 6/2002 | Michelson |
| 6,402,755 B1 | 6/2002 | Pisharodi |
| 6,402,756 B1 | 6/2002 | Ralph et al. |
| 6,406,478 B1 | 6/2002 | Kuo |
| 6,413,259 B1 | 7/2002 | Lyons et al. |
| 6,416,528 B1 | 7/2002 | Michelson |
| 6,428,542 B1 | 8/2002 | Michelson |
| 6,454,769 B2 | 9/2002 | Wagner et al. |
| 6,454,771 B1 | 9/2002 | Michelson |
| 6,458,133 B1 | 10/2002 | Lin |
| 6,471,704 B2 | 10/2002 | Gertzbein et al. |

| | | |
|---|---|---|
| 6,478,797 B1 | 11/2002 | Paul |
| 6,503,250 B2 | 1/2003 | Paul |
| 6,527,776 B1 | 3/2003 | Michelson |
| 6,533,786 B1 | 3/2003 | Needham et al. |
| 6,572,619 B2 | 6/2003 | Santilli |
| 6,575,975 B2 | 6/2003 | Brace et al. |
| 6,579,290 B1 | 6/2003 | Hardcastle et al. |
| 6,585,769 B1 * | 7/2003 | Muhanna et al. ......... 623/13.14 |
| 6,592,586 B1 | 7/2003 | Michelson |
| 6,595,993 B2 | 7/2003 | Donno et al. |
| 6,599,290 B2 | 7/2003 | Bailey et al. |
| 6,602,255 B1 * | 8/2003 | Campbell et al. ........... 606/290 |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,623,486 B1 | 9/2003 | Weaver et al. |
| 6,626,907 B2 | 9/2003 | Campbell et al. |
| 6,652,525 B1 | 11/2003 | Assaker et al. |
| 6,669,700 B1 | 12/2003 | Farris et al. |
| 6,695,846 B2 | 2/2004 | Richelsoph et al. |
| 6,755,833 B1 | 6/2004 | Paul et al. |
| 6,890,334 B2 | 5/2005 | Brace et al. |
| 7,001,387 B2 | 2/2006 | Farris et al. |
| 7,008,426 B2 | 3/2006 | Paul |
| 7,025,769 B1 | 4/2006 | Ferree |
| 7,070,599 B2 | 7/2006 | Paul |
| 7,077,843 B2 * | 7/2006 | Thramann et al. ............ 606/69 |
| 7,204,837 B2 | 4/2007 | Paul |
| 2001/0014807 A1 | 8/2001 | Wagner et al. |
| 2001/0021851 A1 | 9/2001 | Eberlein et al. |
| 2001/0037112 A1 | 11/2001 | Brace et al. |
| 2001/0041894 A1 | 11/2001 | Campbell et al. |
| 2001/0047172 A1 | 11/2001 | Foley et al. |
| 2001/0047174 A1 | 11/2001 | Donno et al. |
| 2002/0013586 A1 | 1/2002 | Justis et al. |
| 2002/0016595 A1 | 2/2002 | Michelson |
| 2002/0022843 A1 | 2/2002 | Michelson |
| 2002/0045896 A1 | 4/2002 | Michelson |
| 2002/0045898 A1 | 4/2002 | Freid et al. |
| 2002/0045899 A1 | 4/2002 | Errico et al. |
| 2002/0049444 A1 | 4/2002 | Knox |
| 2002/0058939 A1 | 5/2002 | Wagner et al. |
| 2002/0065517 A1 | 5/2002 | Paul |
| 2002/0068938 A1 | 6/2002 | Jackson |
| 2002/0077630 A1 | 6/2002 | Lin |
| 2002/0111630 A1 | 8/2002 | Ralph et al. |
| 2002/0120271 A1 | 8/2002 | Dixon et al. |
| 2002/0120272 A1 | 8/2002 | Yuan et al. |
| 2002/0120273 A1 | 8/2002 | Needham et al. |
| 2002/0128654 A1 | 9/2002 | Steger et al. |
| 2002/0128655 A1 | 9/2002 | Michelson |
| 2002/0151893 A1 | 10/2002 | Santilli |
| 2002/0151899 A1 | 10/2002 | Bailey et al. |
| 2002/0151900 A1 | 10/2002 | Glascott |
| 2002/0156474 A1 | 10/2002 | Wack et al. |
| 2002/0161370 A1 | 10/2002 | Frigg et al. |
| 2002/0173790 A1 | 11/2002 | Chang et al. |
| 2002/0183747 A1 | 12/2002 | Jao et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023242 A1 | 1/2003 | Harrington, Jr. |
| 2003/0040749 A1 | 2/2003 | Grabowski et al. |
| 2003/0045880 A1 | 3/2003 | Michelson |
| 2003/0060828 A1 | 3/2003 | Michelson |
| 2003/0078583 A1 | 4/2003 | Biedermann et al. |
| 2003/0093082 A1 | 5/2003 | Campbell et al. |
| 2003/0105462 A1 | 6/2003 | Haider |
| 2003/0130661 A1 | 7/2003 | Soman |
| 2003/0149434 A1 | 8/2003 | Paul |
| 2003/0153920 A1 | 8/2003 | Ralph et al. |
| 2003/0181912 A1 | 9/2003 | Michelson |
| 2003/0187440 A1 | 10/2003 | Richelsoph et al. |
| 2003/0187441 A1 | 10/2003 | Bolger et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2004/0030338 A1 | 2/2004 | Paul |
| 2004/0087951 A1 | 5/2004 | Khalili |
| 2004/0097935 A1 | 5/2004 | Richelsoph et al. |
| 2004/0122426 A1 | 6/2004 | Michelson |
| 2004/0127899 A1 * | 7/2004 | Konieczynski et al. ........ 606/69 |
| 2005/0038436 A1 | 2/2005 | Michelson |
| 2005/0049593 A1 | 3/2005 | Duong et al. |
| 2006/0122602 A1 | 6/2006 | Konieczynski et al. |
| 2006/0122604 A1 | 6/2006 | Gorhan et al. |
| 2006/0149256 A1 | 7/2006 | Wagner et al. |
| 2006/0200147 A1 | 9/2006 | Ensign et al. |
| 2006/0241616 A1 | 10/2006 | Konieczynski et al. |

FOREIGN PATENT DOCUMENTS

| | | |
|---|---|---|
| EP | 0 201 024 B1 | 4/1986 |
| EP | 0 242 842 B1 | 4/1987 |
| EP | 0 410 309 A1 | 7/1990 |
| EP | 0 599 640 B1 | 11/1993 |
| EP | 0 683 646 B1 | 1/1994 |
| EP | 1 106 144 A1 | 1/1994 |
| EP | 0 699 057 B1 | 3/1995 |
| EP | 0 767 631 B1 | 6/1995 |
| EP | 0 828 459 B1 | 4/1996 |
| EP | 1 364 623 A1 | 4/1996 |
| EP | 0 876 128 B1 | 5/1996 |
| EP | 0 874 595 B1 | 12/1996 |
| EP | 0 809 971 A3 | 4/1997 |
| EP | 0 809 971 B1 | 4/1997 |
| EP | 0 809 972 A3 | 4/1997 |
| EP | 0 897 697 A1 | 5/1998 |
| EP | 0 984 728 B1 | 5/1998 |
| EP | 1 340 468 A2 | 5/1998 |
| EP | 0 999 796 B1 | 7/1998 |
| EP | 0 903 113 A2 | 8/1998 |
| EP | 0 995 404 A1 | 10/1998 |
| EP | 0 988 833 A2 | 8/1999 |
| EP | 1 169 971 A2 | 6/2001 |
| EP | 1 285 632 A1 | 8/2001 |
| EP | 1 306 058 A2 | 7/2002 |
| EP | 1 346 697 A2 | 3/2003 |
| EP | 1 336 383 B1 | 8/2003 |
| EP | 1346697 | 8/2003 |
| FR | 994718 | 11/1951 |
| FR | 2435243 | 4/1980 |
| FR | 2519857 | 7/1983 |
| FR | 2794963 | 12/2000 |
| FR | 2810532 | 12/2001 |
| SU | 1424824 | 9/1988 |
| WO | WO 88/03781 | 6/1988 |
| WO | WO 94/17744 | 8/1994 |
| WO | WO 95/31941 | 5/1995 |
| WO | WO 96/00530 | 1/1996 |
| WO | WO 96/05778 | 2/1996 |
| WO | WO 96/08206 | 3/1996 |
| WO | WO 96/39975 | 12/1996 |
| WO | WO 97/22306 | 6/1997 |
| WO | WO 98/51226 | 5/1998 |
| WO | WO 98/34553 | 8/1998 |
| WO | WO 98/34556 | 8/1998 |
| WO | WO 00/25689 | 10/1998 |

| WO | WO 99/04718 | 2/1999 |
| WO | WO 99/21502 | 5/1999 |
| WO | WO 99/56653 | 11/1999 |
| WO | WO 00/03653 | 1/2000 |
| WO | WO 00/66011 | 5/2000 |
| WO | WO 01/26567 | 10/2000 |
| WO | WO 00/78238 | 12/2000 |
| WO | WO 01/01874 | 1/2001 |
| WO | WO 01/26566 | 4/2001 |
| WO | WO 01/82804 | 4/2001 |
| WO | WO 01/82805 | 4/2001 |
| WO | WO 01/89428 | 5/2001 |
| WO | WO 01/49191 | 7/2001 |
| WO | WO 03/17856 | 8/2001 |
| WO | WO 01/64144 | 9/2001 |
| WO | WO 01/89400 | 11/2001 |
| WO | WO 03/53262 | 12/2001 |
| WO | WO 02/76317 | 3/2002 |
| WO | WO 03/007826 | 7/2002 |
| WO | WO 02/080789 | 10/2002 |
| WO | WO 02/098276 | 12/2002 |
| WO | WO 02/098277 | 12/2002 |
| WO | WO 03/063714 | 8/2003 |
| WO | WO 03/071966 | 9/2003 |
| WO | WO2006055156 | 5/2006 |

OTHER PUBLICATIONS

Tippets, Richard H., MD, Apfelbaum, Ronald I., MD (1988). Anterior Cervical Fusion with the Caspar Instrumentation Sytem, *Neurosurgery*, vol. 22, No. 6, Part 1.

Benzel, Edward, MD, Leon Steven P. MD. Enhancing Cervical Spine Fusion[CME], www.medscape.com.

Paramore, Christopher G., MD, Dickman, Curtis A., MD, Sonntag, Volker K.H., MD. Radiographic and Clinical Follow-up Review of Caspar Plates in 49 Patients. *J. Neurosurg.*/vol. 84/Jun. 1996, 957-961.

Clausen, John D.,B.S; Ryken, Timothy C., MD; Traynelis, Vincent C., MD, Sawin, Paul D., MD; Dexter, Franklin, MD, Ph.D.; Goel, Vijay K., Ph.D. Biomechanical Evaluation of Caspar and Cervical Spine Locking Plate Systems in a Cadveric Model. *J. Neurosurg.*/vol. 84/Jun. 1996, 1039-1045.

Bose, Bikash, MD, FACS. Anterior cervical fusion using Caspar plating: analysis of results and review of the literature. *Surg Neurol 1998*, Jan. 49 (1):25-31.

Pitzen, T.; Steudel, W.I.; Oxland, T. The effect of posterior element injury on cervical spine flexibility while using anterior plates with and without posterior fixation, An in vitro trauma model *Neurochirurgische Klinik, Universitatskliniken des Saarlanders, Homburg; Division of Orthopedic Engineering Research*, University of British Columbia, Vancouver, Canada.

Caspar W; Barbier DD; Klara PM. Anterior cervical fusion and Caspar plate stabilization for cervical trauma. *Neurosurger 1989*, Oct. 25(4):491-502.

Armstrong, Gordon W.S., Donald Chow. The Contoured Anterior Spinal Plate. *Spinal Instrumentation*, 1992.

Zdeblic, Thomas A., MD; Ghanayem, Alexander, J. MD; Rapoff, Andrew J., MS; Swain, Carol, MS; Bassett, Tim, MD; Cooke, Mary E., MS; Markel, Mark DVM, Cervical Interbody Fusion Cages, An Animal Model With and Without Bone Morphogenetic Protein. *SPINE*, vol. 23, No. 7, pp. 758-766.

Moftakhar, Roham, MD; Trost, Gregory R., MD. Anterior cervical plates: a historical perspective *Neurosurg Focus 16* vol. 16 (1): Article 8, 2004.

Omeis, Ibrahim, MD; DeMattia, Joseph A., MD; Hillard, Virany Huynh, MD; Murali, Raj, MD; Das, Kaushik, MD, History of instrumentation for stabilization of the subaxial cervical spine. *Neurosurg, Focus*, vol. 16, Article 10, 2004.

Takahashi, Toshiyuki; Tominaga, Teija; Yoshimoto, Takashi. Biomechanical evaluation of hydroxyapatite intervertebral graft and anterior cervical plating in a porcine cadaveric model. *Bio-Medical Materials and Engineering* 7 (1997) 121-127.

Chen, Ing-Ho; Yang, Rong-Sen; Chen, Po-Quang. Plate Fixation for Anterior Cervical Interbody Fusion. *J. Formosan Med. Assoc.* 1991, vol. 90, No. 2.

\* cited by examiner

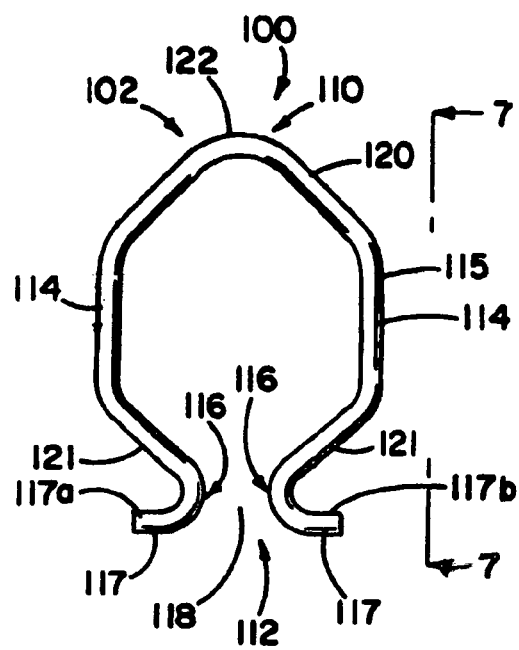
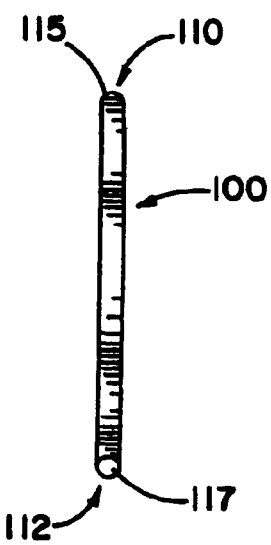
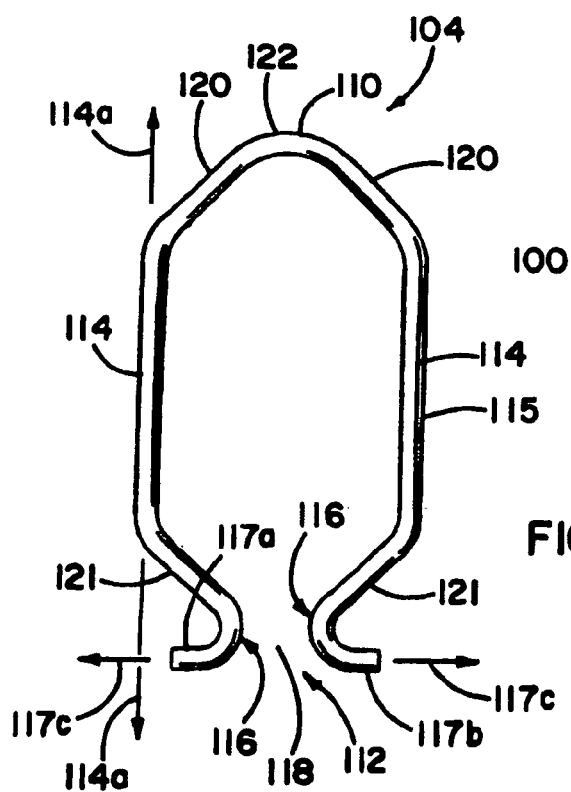
FIG. 6
FIG. 7
FIG. 8

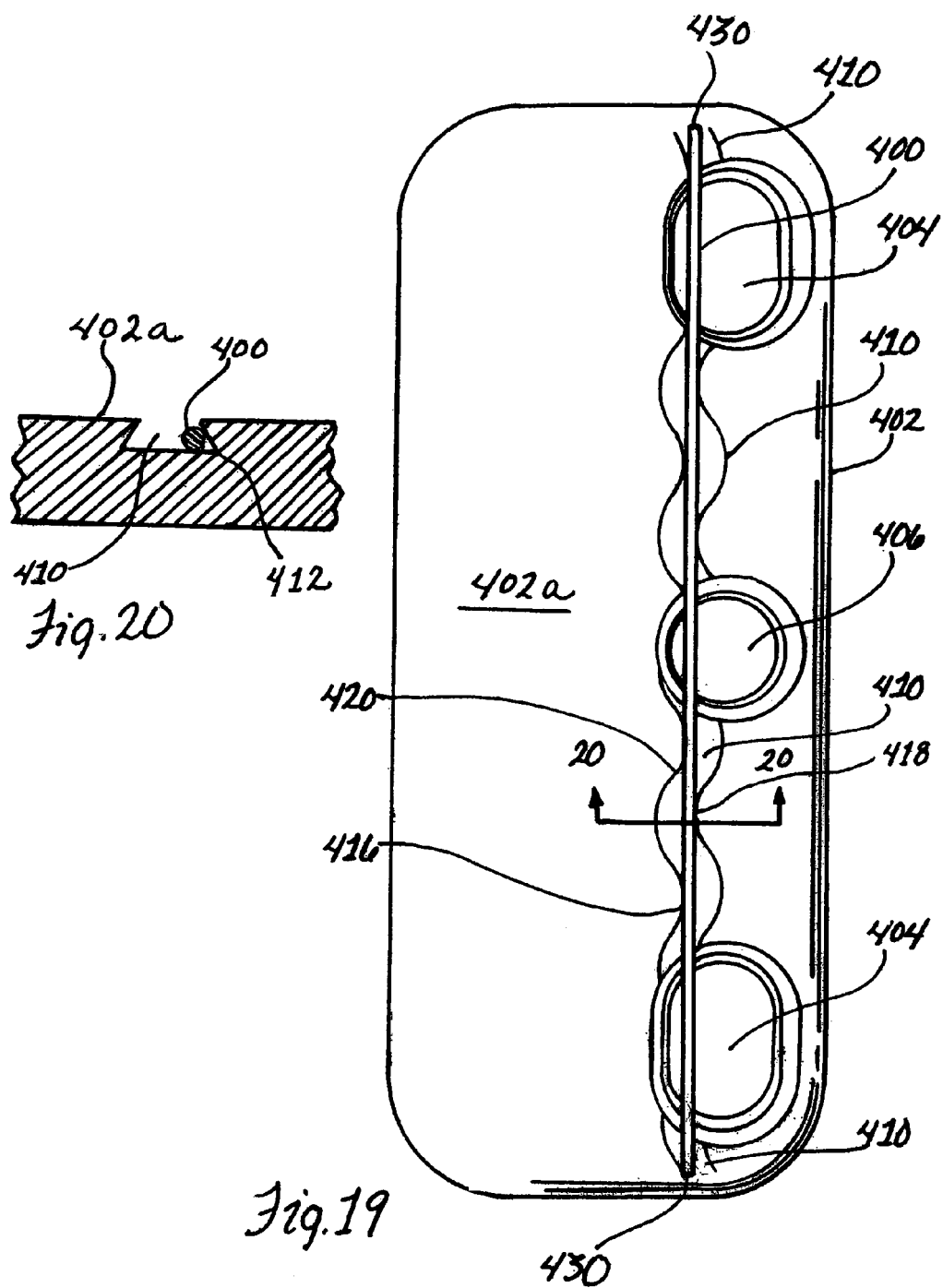

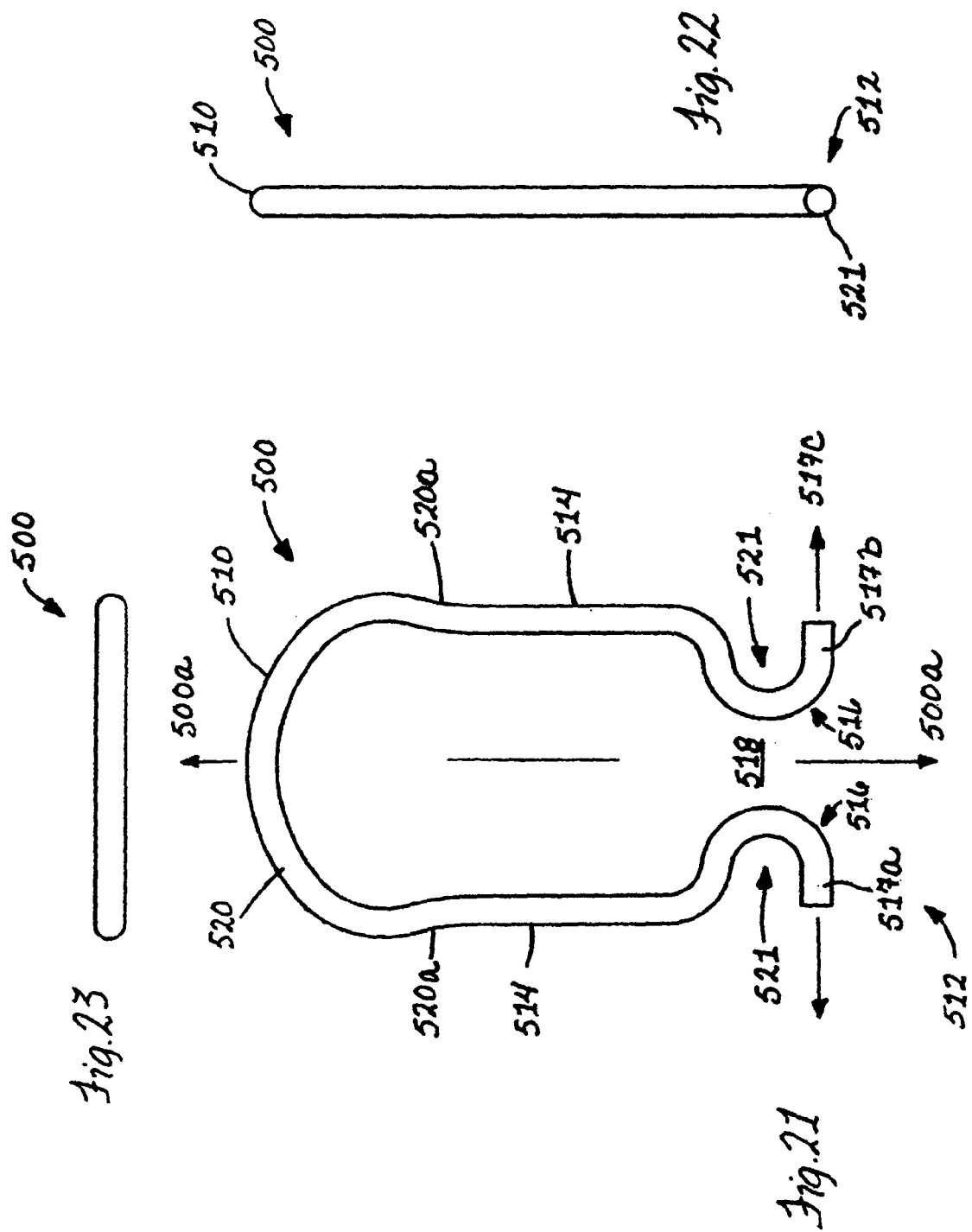

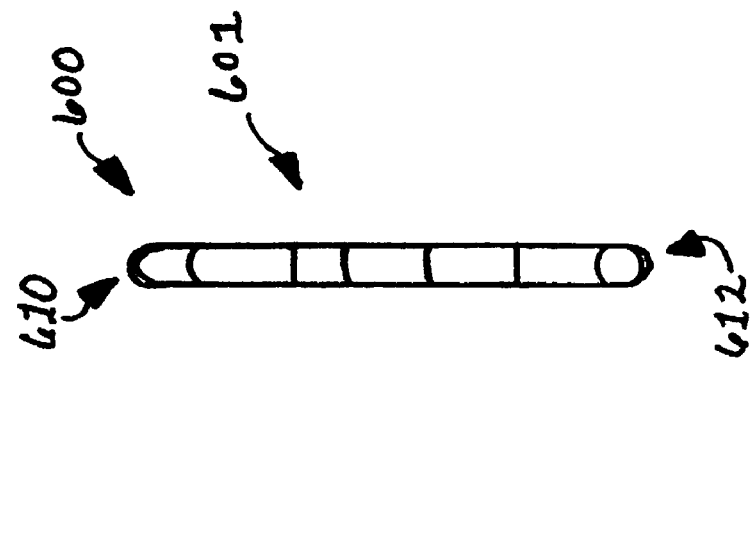
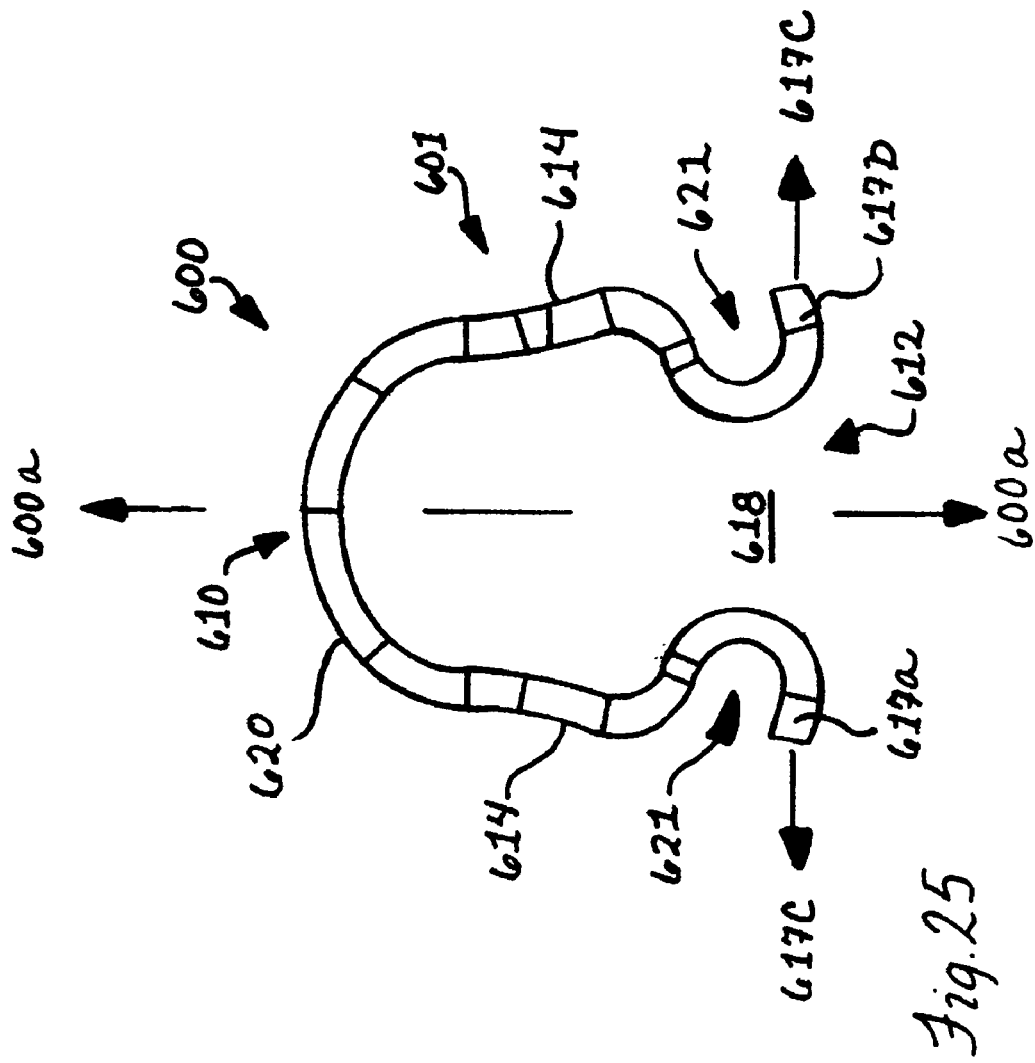

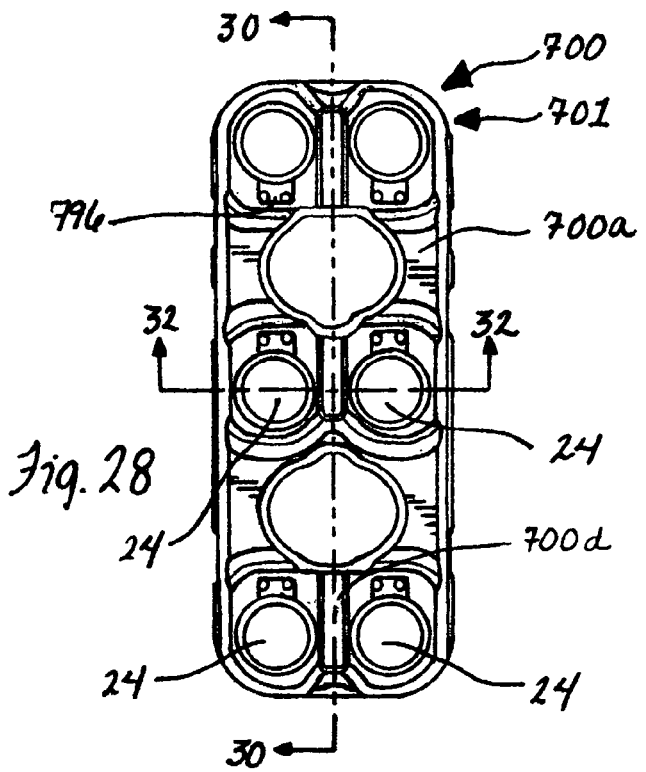
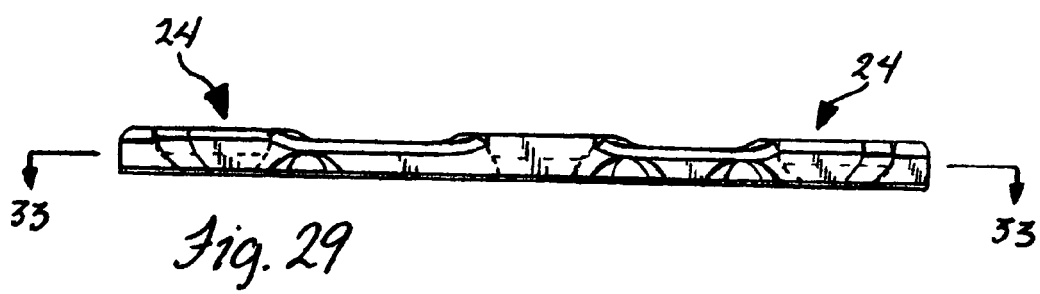

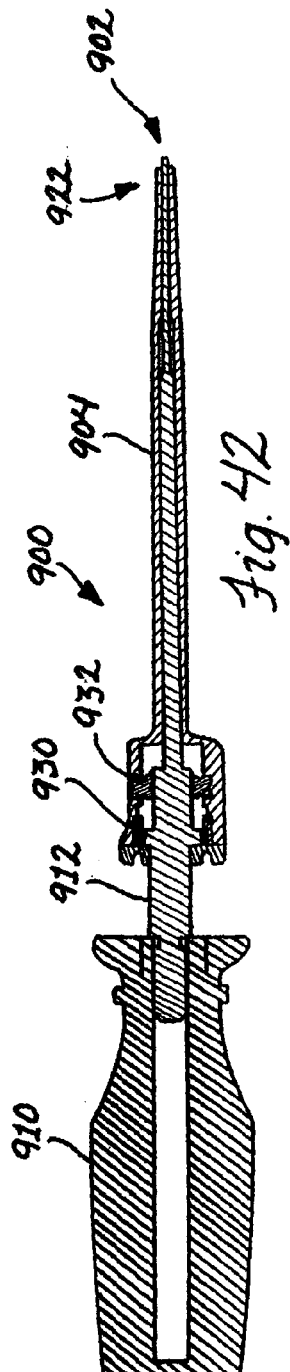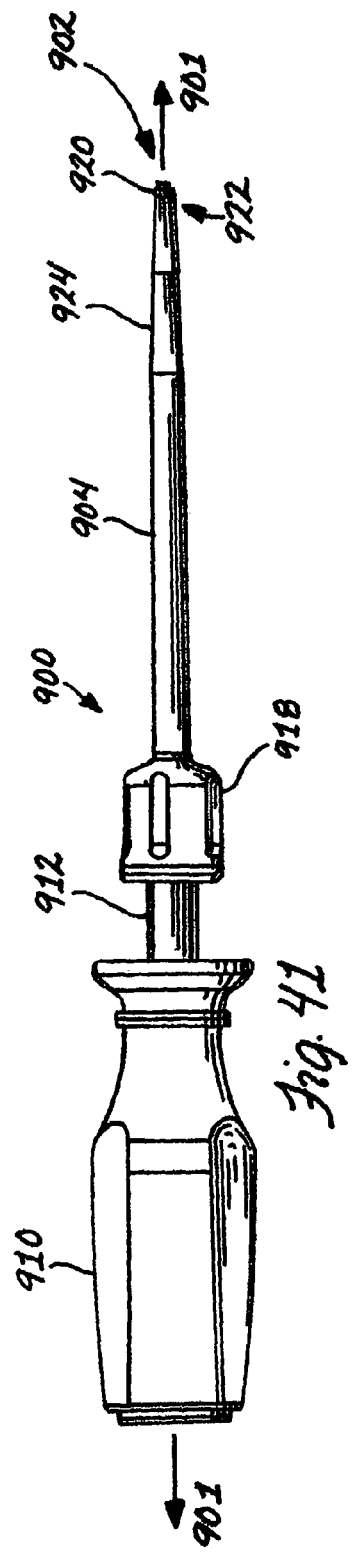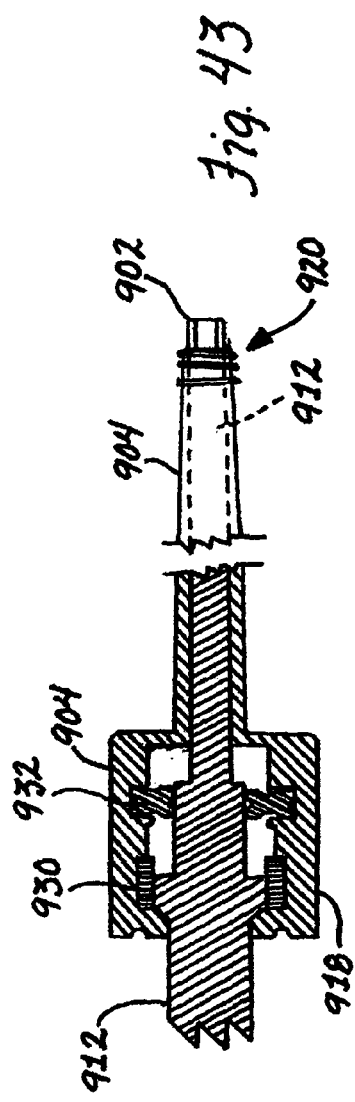

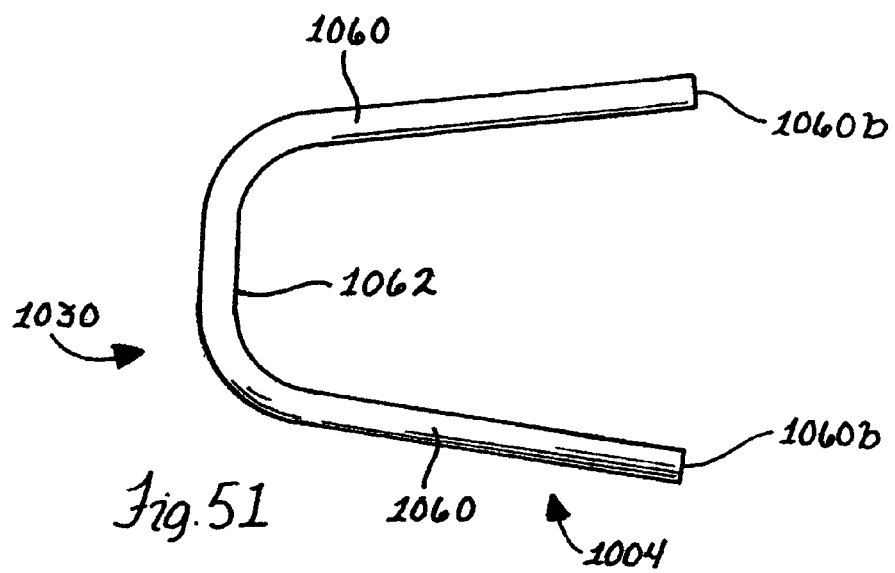
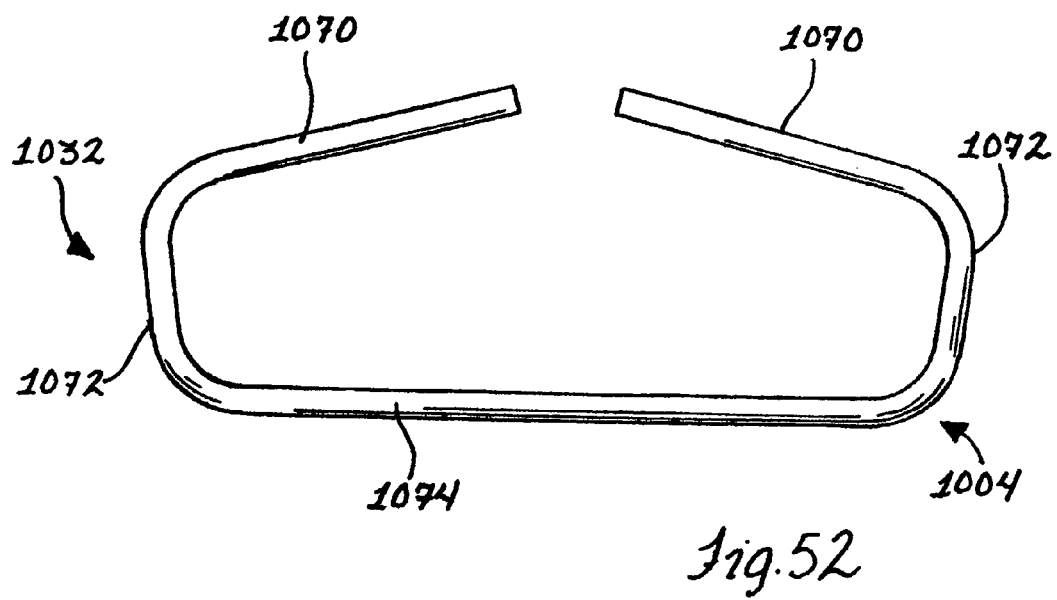

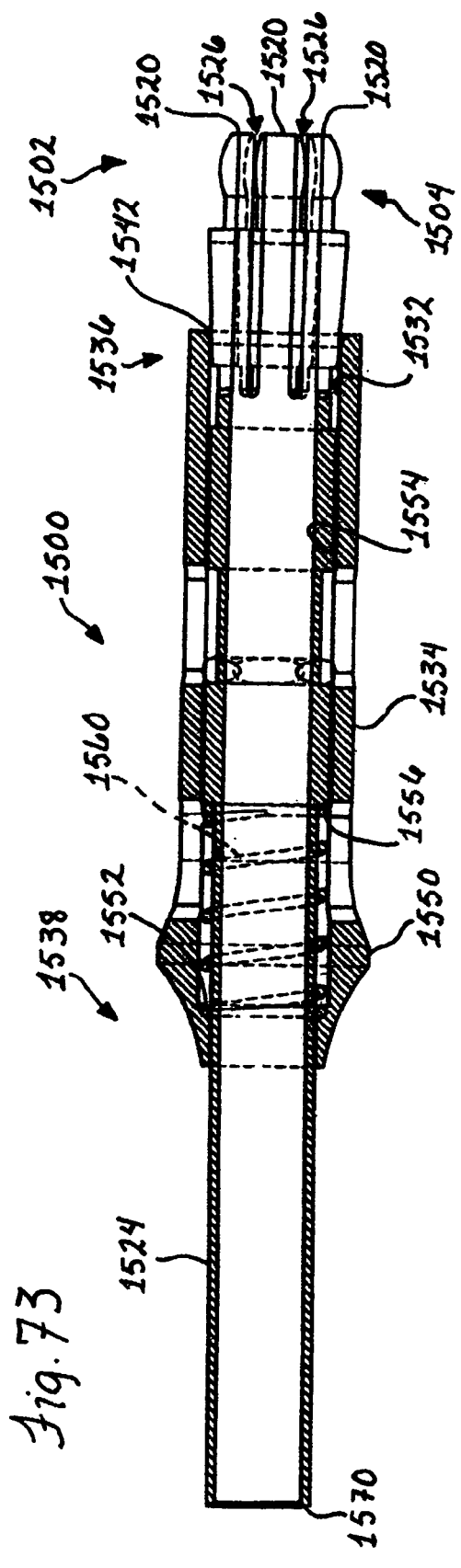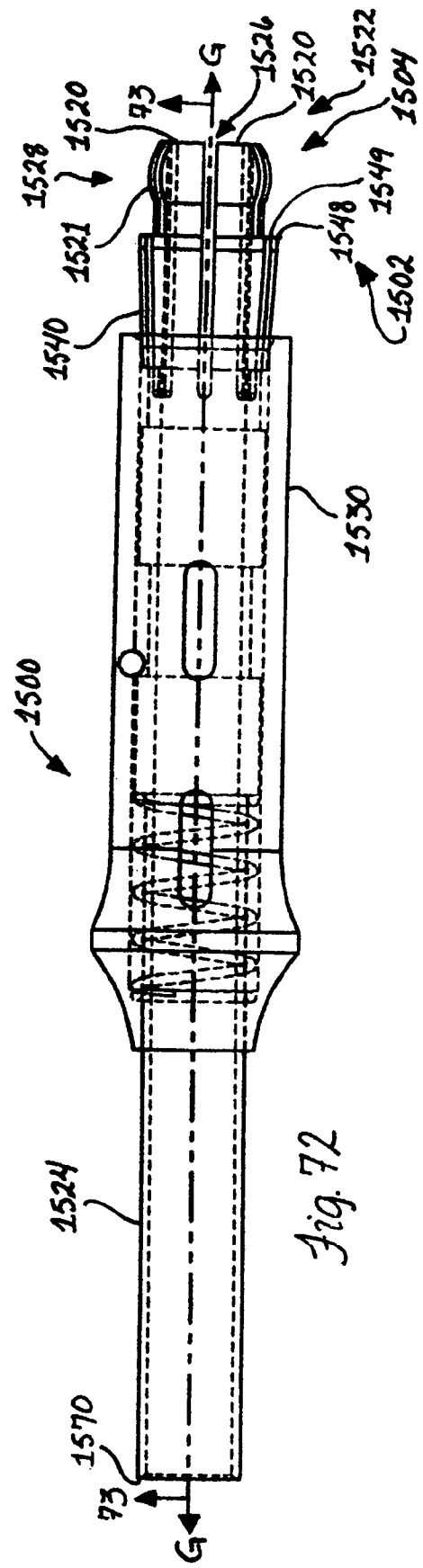

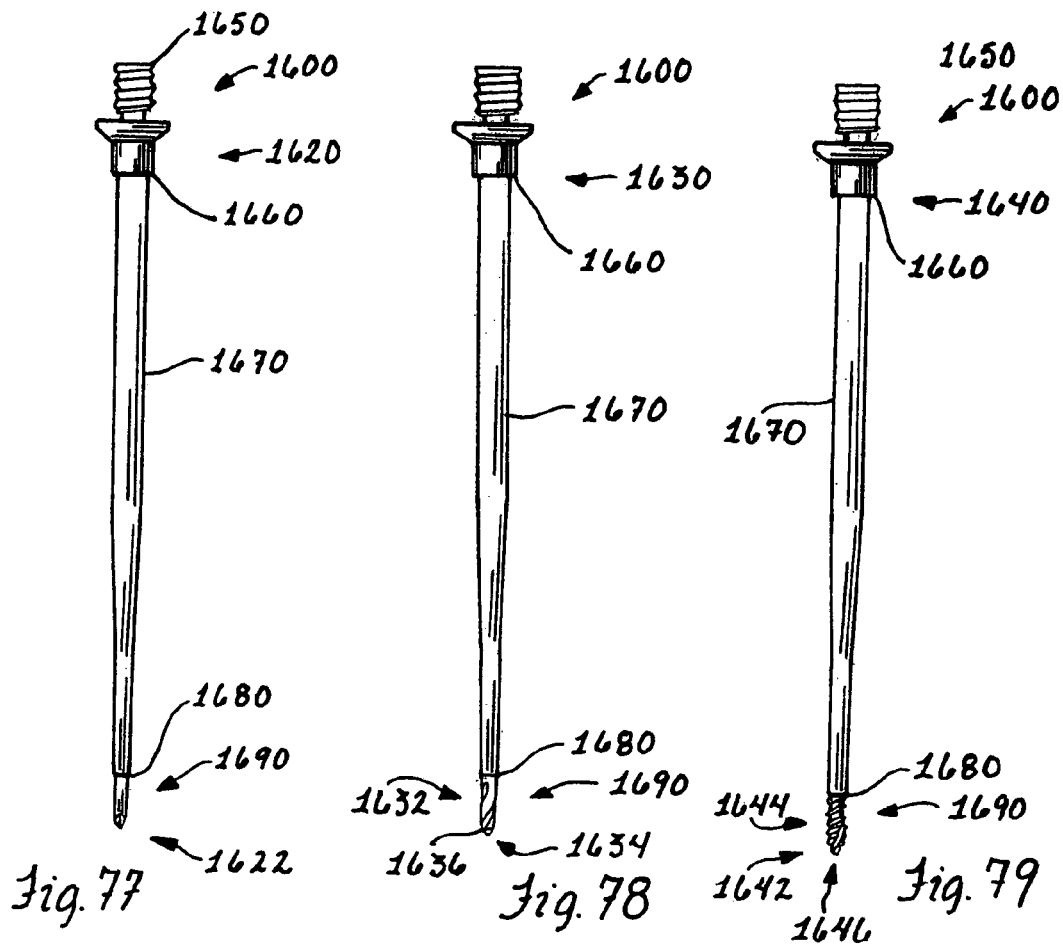
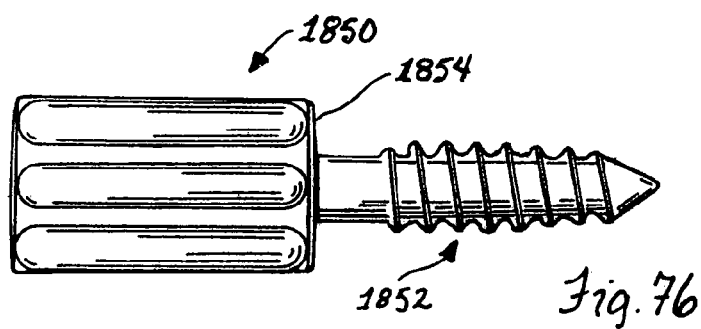

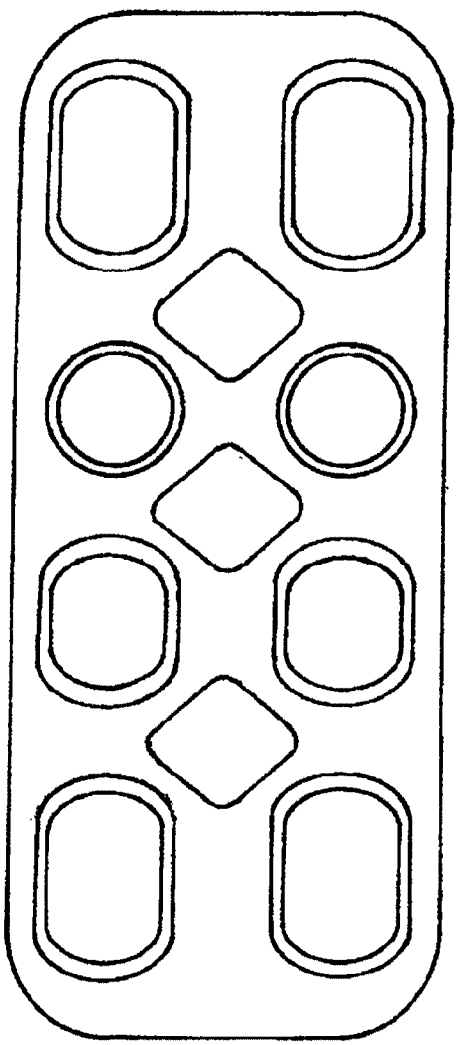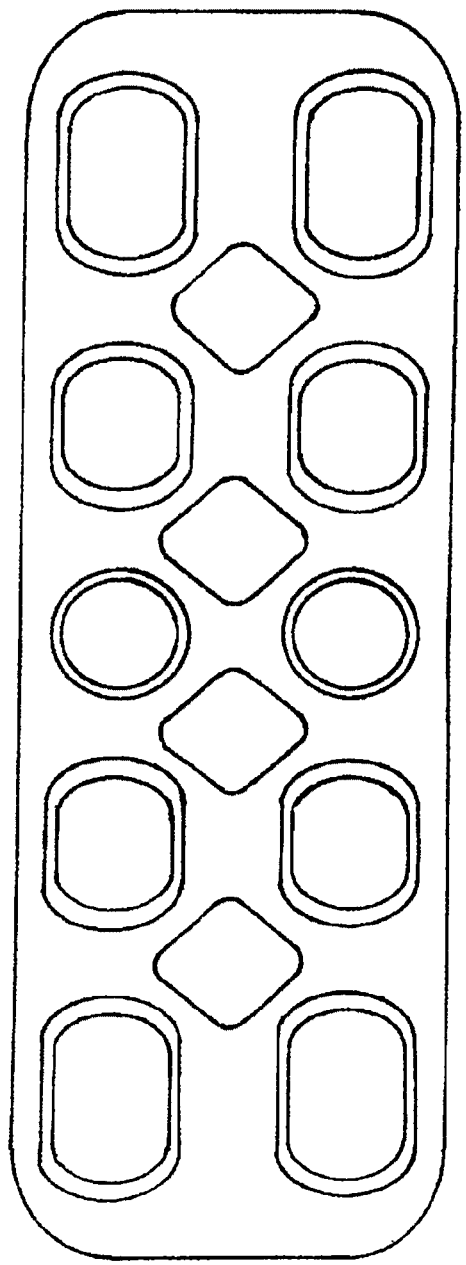
Fig.82
Fig.83

BONE PLATE SYSTEM AND METHODS

CROSS-REFERENCE TO RELATED APPLICATIONS

This application claims the benefit of U.S. Provisional Patent Application No. 60/548,140, filed Feb. 26, 2004, entitled "Bone Plate System."

FIELD OF THE INVENTION

The invention relates to bone plate systems and, more particularly, to a bone plate system including a retention system to prevent the bone anchors from backing out of the plate, and to methods for implanting a bone plate system.

BACKGROUND OF THE INVENTION

There are presently many different types of plate and fixture systems for securing two or more bones or bone fragments in relative position so that the bones may fuse or heal, or so that tissue adjacent the bones may heal without disruption from the movement of the secured bones. As used herein, the term bone may refer to a bone, or a bone fragment or portion, and the term may refer to a portion of a bone that is covered with another material, such as the endplates covering the top and bottom surface of a vertebra. These systems have been used to secure spinal vertebrae and, more specifically, cervical vertebrae.

Bone plate systems are typically used to assist or direct spinal fusion or vertebral healing procedures. These procedures promote earlier post-operative patient mobility, decrease a need for post-operative collars, decrease the incidence of graft dislodgement if a graft is used, and improve success in correcting spinal deformities.

Furthermore, these systems have been found to assist in controlling and/or exerting a loading force applied to the surgical site. As used herein, the term fusion refers to the joining of materials, such as bone or graft material, and the fusion site is the entire region in which fusion may be desired. By applying a compressive load, it has been found that bone heals more optimally and with greater integrity, a principle known as Wolf's law.

A shortcoming with bone plates is the backing out or loosening of the screws. If the screws loosen, the bones are not properly secure and may move relative to each other. This may compromise the ability to achieve optimal bone fusion and bone alignment, or it may lead to loss of graft material, and damage or loss of bone. Furthermore, when the plate is a dynamic or dynamized plate, such that at least some screws may move relative to the plate, these issues may be further compounded or exacerbated by a screw backing out.

In order to increase the amount of loading or compressive force, a number of plate designs have been devised. For instance, compression slots have been formed in a plate whereby a screw receiving bore is in the form of a slot with tapered walls, and a screw with a tapered shank is driven against the tapered wall such that a force between the shank and the slot is directed transverse to the shank. Accordingly, that force compresses the screw and the bone to which the screw is connected towards another bone connected to the plate. Another manner for permitting compressive force between joined bones is to utilize a dynamic plate having at least one elongated screw aperture that allows settling of the vertebrae by gravity by allowing at least one secured bone to move slightly relative to the plate. However, heretofore known arrangements of fixed and dynamized apertures in such plates provide less than optimal capacity for controlling the movement and/or compression between more than two levels of secured vertebrae.

Accordingly, there is a need for improved bone plates, bone plate systems for retarding screw backout, and improved methods for utilizing bone plate systems.

BRIEF DESCRIPTION OF THE DRAWINGS

FIG. 6 is a plan view of a retainer;

FIG. 7 is a side elevational of the retainer of FIG. 6 taken along the line 7-7;

FIG. 8 is a plan view of another retainer;

FIG. 19 is a plan view of another embodiment of a bone plate system including a bone plate having bores and a retainer located proximate thereof;

FIG. 20 is cross-sectional view of the bone plate and retainer of FIG. 19 taken along the line 20-20;

FIG. 21 is a plan view of a further embodiment of a retainer;

FIG. 22 is a side elevational view of the retainer of FIG. 21;

FIG. 23 is an end view of the retainer of FIG. 21;

FIG. 25 is a plan view of a further embodiment of a retainer;

FIG. 26 is a side elevational view of the retainer of FIG. 25;

FIG. 28 is a plan view of a further embodiment of a bone plate;

FIG. 29 is a side elevational view of the bone plate of FIG. 28;

FIG. 30 is a cross-sectional view of the bone plate of FIG. 28 taken through the line 30-30;

FIG. 41 is side elevational view of a driver for use with bone plates, retainers, and screws;

FIG. 42 is a cross-sectional view of the driver of FIG. 41;

FIG. 43 is a fragmentary view in partial cross-section of the driver of FIG. 41;

FIG. 51 is a top plan view of the retainer of FIG. 45 for operating in a single hole;

FIG. 52 is a top plan view of the retainer of FIG. 45 for operating in a pair of holes;

FIG. 66 is an exploded view of the bending tool;

FIG. 72 is a side elevation view of a drill guide for directing cutting members;

FIG. 73 is a cross-sectional view of the drill guide;

FIG. 76 is a side elevational view of a holding pin for maintaining the position of a bone plate during implantation;

FIG. 77 is a side elevational view of an awl for creating a pilot hole for implanting a bone plate, shown without corresponding gripping handle;

FIG. 78 is a side elevational view of a drill for opening a hole for implanting a bone plate, shown without corresponding gripping handle;

FIG. 79 is a side elevational view of a tap for providing threads in a hole for implanting a bone plate, shown without corresponding gripping handle;

FIG. 82 is a top plan view of an embodiment of a four-tier bone plate; and FIG. 83 is a top plan view of an embodiment of a five-tier bone plate.

DETAILED DESCRIPTION OF THE PREFERRED EMBODIMENT(S)

Referring to the FIGURES, exemplary bone plate systems for securing a plurality of bones 12 in a desired orientation or arrangement are illustrated including features in accordance with the present invention. In some forms, the bone plate system is a dynamized plate, or has at least one set of dynamic holes, so that bones 12 may compress and shift toward each other, such as the bone plate system 10 depicted in FIG. 1. In other forms, such as exemplified in FIG. 28, a bone plate system 700 is illustrated as non-dynamized. It should be noted that a bone plate system may be provided including a bone plate where each bore thereof is dynamic, as is described herein, or non-dynamic, also described herein. In addition, a dynamized bone plate may utilize a combination of dynamic and non-dynamic bores.

Figure 1:
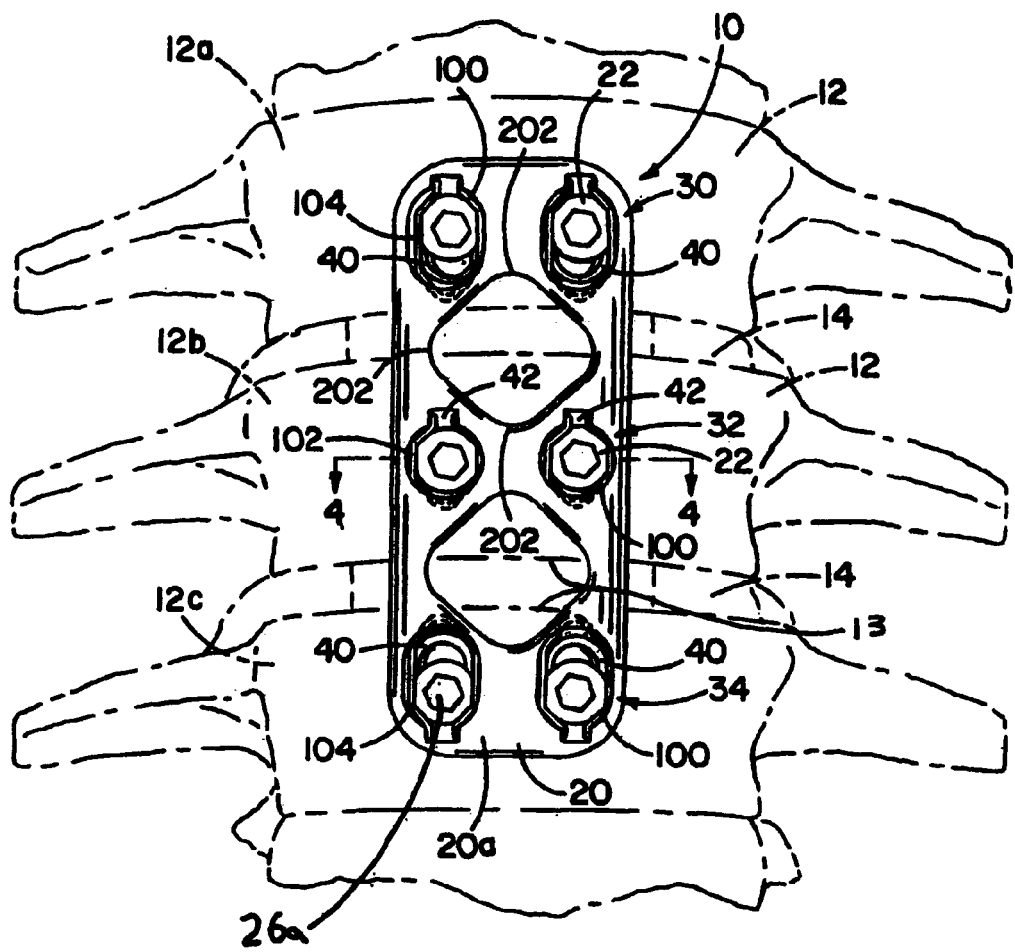
FIG. 1 is a plan view of a bone plate system including features in accordance with the present invention and securing vertebrae in a particular orientation.

Referring now to FIG. 1, the bone plate system 10 assists in the healing and repair of damaged, fractured, or broken bones 12. In the illustration of FIG. 1, the bones 12 are adjacently located vertebrae of a spine, each spaced by a spinal disc 14. The bone plate system 10 may also be used, accordingly, to assist in the healing necessary after trauma has been experienced by the spinal disc 14. For instance, the bone plate system 10 may be utilized for stabilization and securement when adjacent vertebrae are fused, with or without the assistance of a bone graft between the vertebrae.

In each of these examples, the bone plate system 10 is used to secure the bones 12 (and any prosthetic or graft) in a desired spatial relationship. Typically, the desired spatial relationship between the bones 12 (vertebrae) is generally vertical, such as the vertebrae would be in a normal, healthy spine when the person is standing. As discussed above, compression or loading of bones promotes healing of the bones or bone fragments and improves the integrity of the fusion therebetween. Particular to some bones in the human anatomy is that the weight of the person, due to gravity, compresses those bones, such as a femur. For spines, the fusion of adjacent vertebrae can similarly benefit from using the weight of the person to compress the adjacent vertebrae.

Accordingly, though the bones 12 are secured in a desired spatial relationship, the dynamized bone plate system 10 preferably allows the bones 12 to shift relative to each other. In other words, to capitalize on the compression imparted to the adjacent vertebrae by the weight of a person, the bone plate system 10 is designed to allow the bones 12 to compress in a manner dictated by the bone plate system 10.

The bone plate system 10 includes a bone plate 20 secured to the bones 12 with bone anchors which are, in the preferred form, bone screws 22 each having a head 26 and a threaded shank 28. The bone screws 22 are preferably polyaxial for being driven into the bones 12 at an angle in relation to the plate desired by the surgeon or dictated by the surgical site. However, fixed angle screws, as described herein, may also be used.

In use, a surgeon would secure the bone plate 20 by driving the bone screws 22 through bores 24 formed in the plate 20 for receiving the screws 22 and by driving the shank 28 of the screws 22 into the bones 12. The plate 20 preferably has a pair of bores 24 forming a tier and being located at each level at which a bone 12 or bone cement is to be secured thereto. As depicted, the plate 20 has an uppermost tier 30, an intermediary tier 32, and a lowermost tier 34, each respectively in general proximity to an uppermost vertebrae 12a, an intermediary 12b vertebrae, and a lowermost vertebrae 12c, where the plate 20 is utilized for securing the three vertebrae 12a, 12b, 12c in a spatial relationship. Although depicted as three tiers 30, 32,34, any number of tiers could be provided for securing a plurality of bones, bone segments, or implanted materials.

In order to permit the above-described compressive shifting of the bones 12 due to the weight of a person, the plate 20 is a dynamized or dynamic plate. In the presently depicted embodiments, the plate 20 allows the bones 12 to compress towards each other by allowing at least a portion of the bone anchors in the form of screws 22 to shift relative to the plate 20 in a manner defined by the plate 20. To enable this compression, at least some of the bores 24 are dynamized bores 40.

Figure 2:
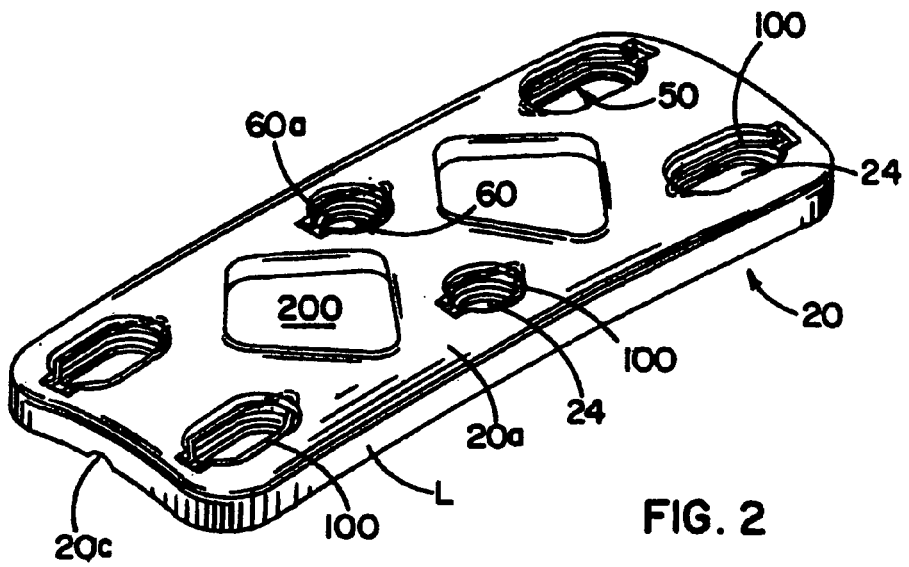
FIG. 2 is a perspective view of the bone plate of FIG. 1.
Figure 3:
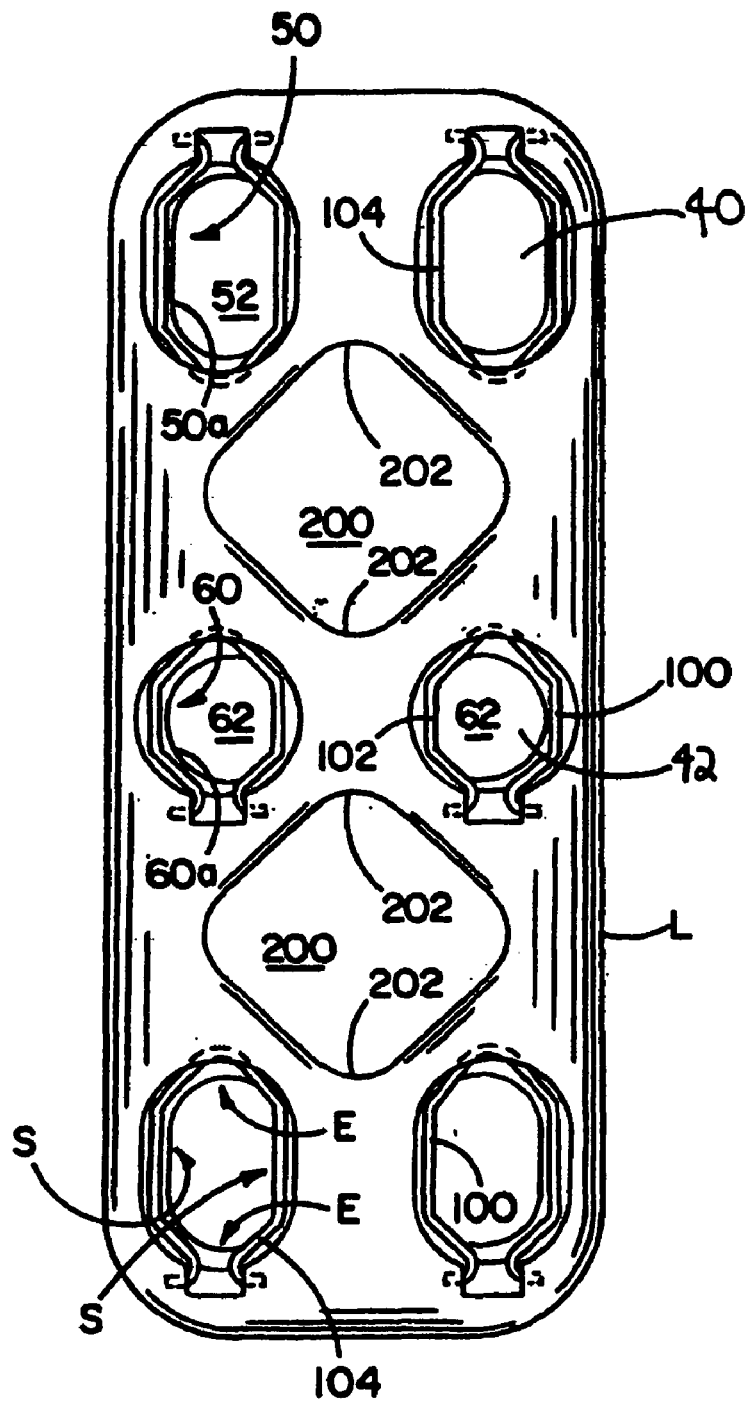
FIG. 3 is plan view of the bone plate of FIG. 2.

In the embodiments illustrated in FIGS. 1-3, the bores 24 of the uppermost and lowermost tiers 30, 34 are dynamized bores 40, while the bores 24 of the intermediary tier 32 are non-dynamized bores 42 such that the non-dynamized bores 42 permit either no or minimal shifting of the screw head 26 and shank 28 within and/or relative to the non-dynamized bore 42. In this manner, the uppermost bone 12a secured by the dynamized bores 40 of the uppermost tier 30 may translate toward the intermediary bone 12b secured by the non-dynamized bores 42 of the intermediary tier 32. Likewise, the lowermost bone 12c secured by the dynamized bores 40 of the lowermost tier 34 and the intermediary bone 12b secured by the non-dynamized bores 42 of the intermediary tier 32 may translate relatively toward each other, in which case both the uppermost bone 12a and intermediary bone 12b are jointly translating towards the lowermost bone 12c. It should be noted that the plate 20 may be equipped with two, or more, tiers 30, 32, 34 with each tier having non-dynamized bores 42, or each tier having dynamized bores 40, or any combination thereof, as desired. For instance, the plate 20 may have four tiers (not shown) including an uppermost tier, a lowermost tier, and superior and inferior intermediary tiers, preferably with one of the intermediary tiers having non-dynamized bores, most preferably the inferior intermediary tier having non-dynamized bores.

By orienting the dynamized bores 40 above and below the non-dynamized bores 42, as depicted and described, the amount of translation by the three bones 12a, 12b, 12c is such that the uppermost and lowermost bones 12a, 12c translate relatively towards the intermediary bone 12b the proper amount. In contrast and by example, if the uppermost and intermediary tiers 30,32 were provided with dynamized bores, the uppermost tier 30 would not only need to shift a distance towards the intermediary tier 32, but would also need to shift more than the distance that the intermediary tier 32 shifts towards the lowermost tier 34. In other words, the cumulative translation required for the uppermost tier 30 is minimized in the present arrangement, which improves effectiveness and minimizes explantation or crushing of a fusion graft. Furthermore, the present arrangement creates better fixation between the plate 20 and the bones 12 by reducing respective moment arms between the screws 22 of the intermediary tier 32 and screws 22 of the uppermost and lowermost tiers 30, 34.

Figure 5A:
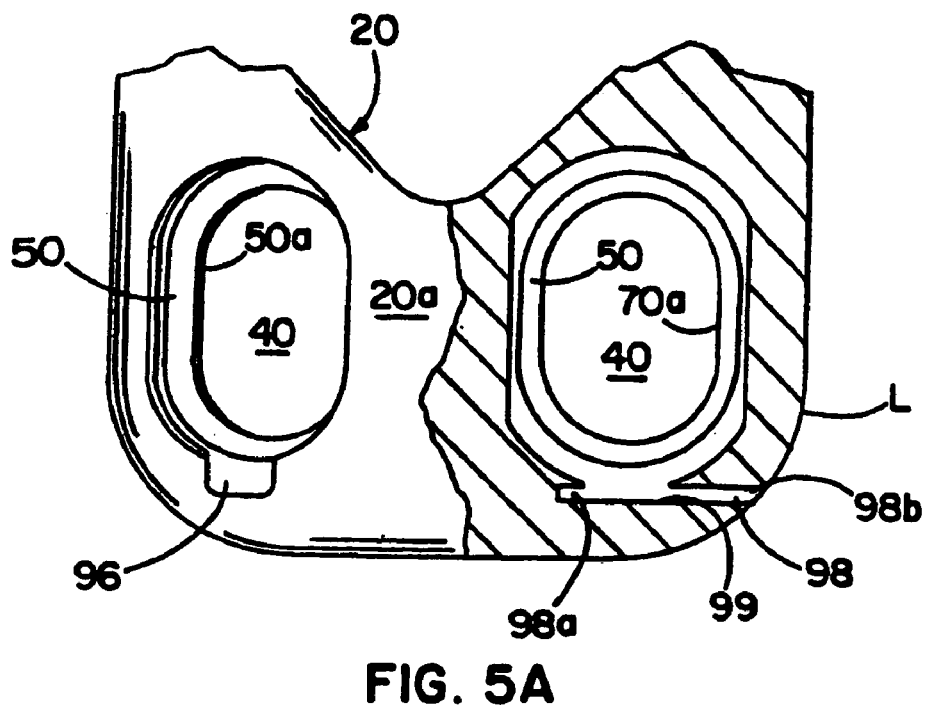
FIGS. 5A and 5B are partial cross-sectional views of the bone plate with and without a retainer, respectively, located within a bore of the bone plate.

More specifically, and with reference to FIG. 5A, the dynamized bore 40 has an interior surface 50 with a racetrack, or oval, shape for receiving the screw head 26 where a lowermost portion 50a of the interior surface 50 defines a racetrack-shaped throughbore 52 for receiving the screw shank 28. As used herein, a racetrack shape refers to a shape with oppositely oriented arcuate portions joined by straight portions. Accordingly, when a screw 22 is located within the dynamized bore 40 and secured in a bone 12, the screw 22 can shift towards the center (the intermediary tier 32) of the plate 20 due to compression of the bones 12. Specifically, the screw head 26 can translate along the interior surface 50, and the screw shank 28 can translate within the throughbore 52, such translation being due to the weight of the erect person exerting a compression force along the spine. The interior surface 50 and throughbore 52 define the path of translation or shifting for the screw 22.

The dynamized and non-dynamized bores 40, 42 have generally similar construction, with some notable differences. The non-dynamized bores 42 have an interior surface 60 for receiving the screw head 26, and the interior surface 60 has a lowermost portion 60a defining a throughbore 62 for receiving the screw shank 28. The interior surface 60 and lowermost portion 60a generally correspond to the interior surface 50 and lowermost portion 50a of the dynamized bore. However, in contrast, the interior surface 60, lowermost portion 60a, and throughbore 62 of the non-dynamized bore 42 are not racetrack-shaped, instead being generally circular, so that the screw 22 received therein is not permitted to shift or translate relative to the plate 20 due to compression force on the spine when the screw is secured to the plate 20 and the bone 12. Simply stated, the non-dynamized bores 42 and features thereof for receiving a screw 22 are generally circular, while the dynamized bores 40 are elongated from a circle to have arcuate or circular ends with generally straight sections therebetween. Therefore, a lateral cross-section of a bore 24, whether dynamized or non-dynamized, includes the same general features.

Figure 4:
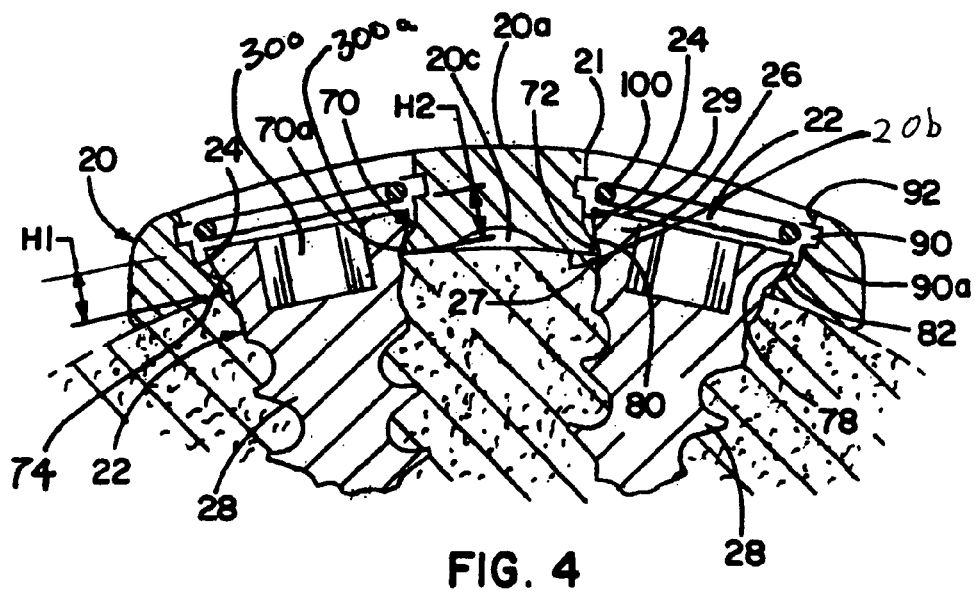
FIG. 4 is a cross-sectional view of the bone plate system of FIG. 1 taken along the line 4-4.

A plate 20 with representative pairs of bores 24 and screws 22 located therein is depicted in FIG. 4. Each bore 24 has an inner surface 70 and a lowermost portion 70a defining a throughbore 72 corresponding to the above described interior surfaces 50, 60, lowermost portions 50a, 60a, and throughbores 52, 62 of the dynamized and non-dynamized bores 40,42. When a screw 22 is secured within the bore 24, the screw head 26 secures against the inner surface 70, and the screw shank 28 extends from the throughbore 72 and is secured within the bone 12. A bridge or neck 27 portion connects the head 26 to the shank 28. Each portion of the screw 22, other than helical threads of the shank 28, is generally circular.

The preferred screw 22 is polyaxial so that the screw may be driven through the bore 24 at a selected angle. Accordingly, the screw head 26 is larger than the screw shank 28 and the throughbore 72, and the screw shank 28 is smaller than the throughbore 72. The inner surface 70 has a brace surface 74 within which the bridge 27 of the screw 22 is positioned, the bridge 27 being smaller in diameter than the bore 24 within the brace surface 74.

The brace surface 74 transitions to a seat surface 78 at a shoulder position 80. When the screw 22 is secured in a bone 12, the screw head 26 rests against the shoulder position 80, and the screw head 26 has an arcuate profile 82 that is able to seat properly against the shoulder 80 at the selected angle, as is depicted in FIG. 4. The neck or bridge 27 is sized relative to the bore 24 within the brace surface 74 to allow the proper amount of angulation for the screw 22 to be pivoted for a selected angle. That is, greater difference in diametral size of the neck 27 and the bore 24 within the brace surface 74 permits greater pivoting extent for the screw 22 located therein.

It should be noted that the shoulder 80 may have a number of constructions, such as simply an edge, or may be a chamfer, for instance. The seat surface 78 is preferably larger in diameter than the screw head 26 to provide clearance so that the screw 22 may be mounted in a selected angle. Alternatively, the seat surface 78 and screw head 26 may be spherical with closely matched diameters so that the screw head 26 may polyaxially slide against the seat surface 78 for driving the screw 22 in the bone 12 at the selected angle.

As discussed, screw back-out impairs the integrity of the securement of the bone plate system 10 to the bones 12. Therefore, in order to prevent back-out of the screws 22, the bone plate system 10 includes anchor retainers 100, and preferably a retainer 100 is provided for each bore 24. Above the seat surface 78 is a recess 90 extending around the inner periphery of the inner surface 70. A portion of the retainers 100 may be secured or located in the recess 90. The screw head 26 has a height H1 that is less than a height H2 of the seat surface 78. The height differential between H1 and H2 allows the screw 22 to pivot a predetermined amount before the screw head top surface 29 interferes with the retainer 100 when it is pivoted. Accordingly, it is preferred that the top surface 29 of the screw 22 is generally positioned below a lower edge 90a of the recess 90 when the screw 22 is secured straight through the bore 24, or is positioned below or generally coincident with the lower edge 90a when the screw is secured at a selected pivoted angle.

Above the recess 90, the inner surface 70 has a receiving portion 92 that terminates at a top edge 21 meeting with a top surface 20a of the plate 20. For a non-dynamized bore 42, each described portion of the inner surface 70 is generally circular in shape. In addition, each described portion of the inner surface 70 for a dynamized bore 40 is generally circular at the arcuate ends E and is straight for the straight sides S (see FIG. 3).

Once the screws 22 are located within the bores 24, at least a portion of each retainer 100 is over top surface 29 of the screw head 26 such that the retainer 100 prevents the screw 22 from backing out through the bore 24. The retainers 100 are preferably preset in the plate 20 during the assembly process such that a surgeon can handle the plate 20 and retainers 100 as a single unit. However, alternatively, the screws 22 may be driven into the bones 12 to secure the plate 20 thereto, and the retainers 100 may then be inserted to prevent back-out of the screws 22. As depicted in FIG. 1, the plate 20 is shown secured to bones 12 with screws 22, and the screws 22 are prevented from backing out by the retainers 100.

In order to permit the screws 22 to be driven into the plate 20, the preset retainers 100 expand while the screw 22 is being driven therethrough. FIGS. 6-8 depict retainers 100 and, more particularly, depict a retainer 102 for a non-dynamized bore 42 (see FIG. 6) and a retainer 104 for a dynamized bore 40 (see FIG. 8). Each retainer 102, 104 has a closed end 110, an open end 112 opposite the closed end 110, and straights 114 located between the closed and open ends 110, 112. The retainer 100 is held within the plate 20 by the recess 90.

Figure 9:
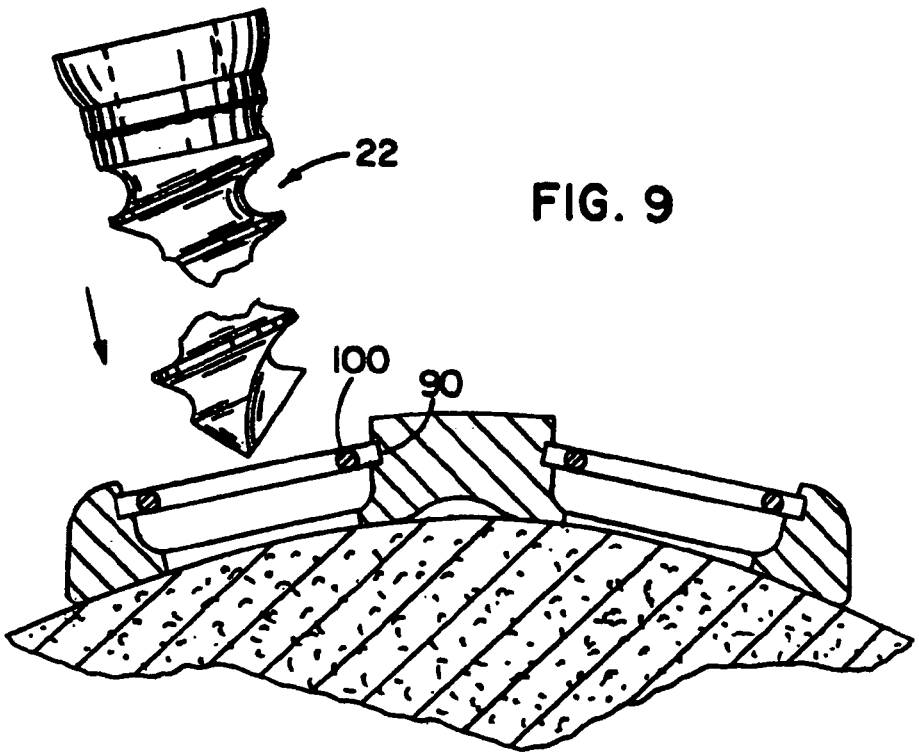
FIG. 9 is a cross-sectional view of the bone plate system and a screw indicating insertion into the bone plate and a bone to which the bone plate system is to be secured.
Figure 10:
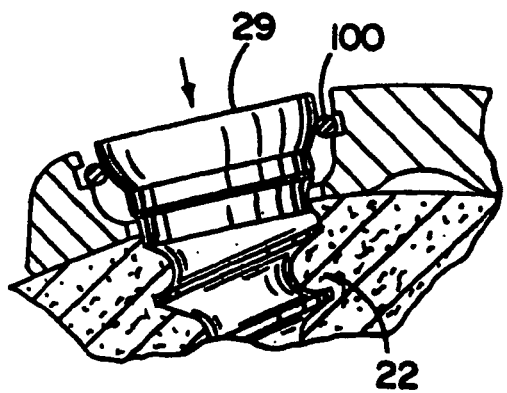
FIG. 10 is a cross-sectional view of the bone plate system and screw of FIG. 9 with the screw partially inserted into the bone plate and bone.
Figure 11:
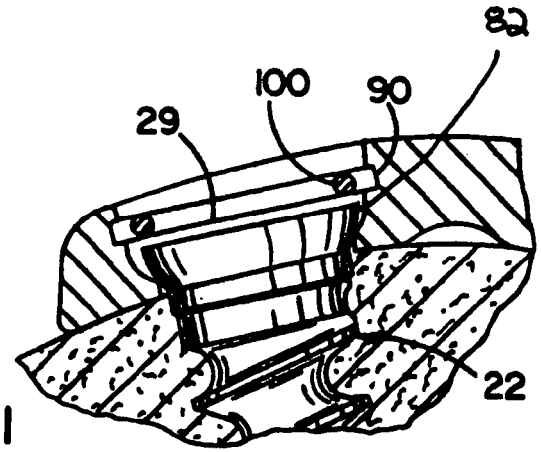
FIG. 11 is a cross-sectional view of the bone plate system and screw of FIG. 9 with the screw fully inserted into the bone plate and bone.

Prior to the screw 22 being inserted into the plate 20, the straights 114 of the retainer 100 are positioned in a static position as is depicted in FIG. 9. More specifically, the straights 114 extend through the bore 24 to interfere with the path of the screw head 26 to contact the seat surface 78. As the screw 22 is driven into the bone 12, the screw head 26 contacts the straights 114, as is depicted in FIG. 10. As the screw 22 continues into the bone 12 and plate 20, the arcuate profile 82 of the screw head 26 cams against the straights 114 and forces, wedge-like, the straights 114 away from each other and into the recess 90. Once the screw head 26 passes through and below the retainer 100 and its straights 114, the retainer 100 generally returns to its static position such as that prior to insertion of the screw, as can be seen in FIG. 11. The screw 22 is, as discussed above, seated in the bone 12 and plate 20 such that the top surface 29 is generally below or approximately coincident with the lowermost edge 90a of the recess 90 so that the retainer 100 held within the recess 90 is over the top surface 29 of the screw head 26 to prevent screw back out.

As mentioned above, the recess 90 secures and holds the preset retainers 100 in the bores 24. The closed end 110 of the retainer includes two arms 120 joined by an elbow 122 that is slightly arcuate, though preferably with a smaller radius of curvature than the bores 24. The open end 112 includes two arms 121 each terminating with a leg 116 separated by a gap 118. Each leg 116 has a straight portion in the form of a foot 117a, 117b, aligned along an axis 117c generally orthogonal to an axis 114a of the straights 114.

Figure 5B:
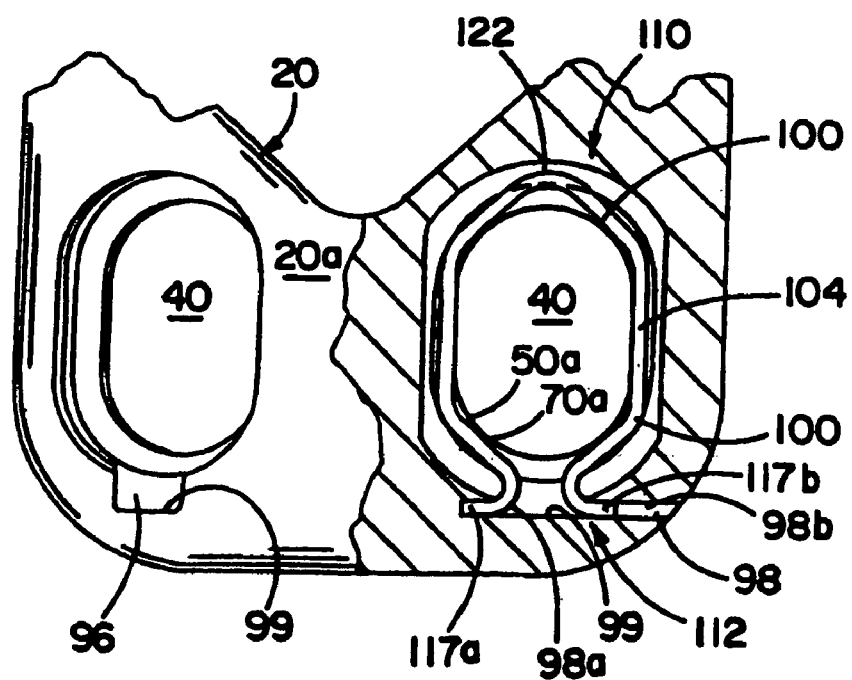

To insert the retainer 100 within the bore 24 of the plate 20, the open end 112 is compressed so that the legs 116 are brought together and the gap 118 therebetween is reduced or eliminated. The retainers 100 are elastically resilient so that the closed end 110 may bend due to this compression, so that the open end 112 may be compressed and return to its natural shape when released, and so that the retainer 100 may expand and contract as the screw head 28 passes through and beyond the retainer 100. The closed end 110 is then inserted into the recess 90, and the open end 112 is then inserted into a tab-shaped recess 96, as depicted in FIGS. 5A and 5B.

Each bore 40, 42 includes the tab-shaped recess 96 extending from the top surface 20a of the plate 20 through the receiving portion 92 of the inner surface 70 of the bore 24, and the tab recess 96 joins with the recess 90. The tab recess 96 allows the compressed legs 116 to be received in a portion of the recess 90. In addition, a retainer pilot 98 is provided as a bore for receiving the feet 117 of the retainer 100. The retainer pilot 98 may be drilled from a lateral side L of the plate 20 so that it is coincident with and through the tab recess 96. Accordingly, the edges of the retainer pilot 98, the tab recess 96, and the recess 90 that are outboard from the bore 24 are preferably aligned and coincident at a surface 99. The left and right feet 117a and 117b are inserted in respective portions of the retainer pilot 98a and 98b for holding and securing the feet 117 therein so that the retainer 110 is secured within the bore 24. It should be noted that the present embodiments of the retainers 102, 104 are described where the recess 90 extends around the entire periphery of the inner surface 70 of the bores 24. However, it should be clear that much of the receiving portion of the inner surface 70 above such a recess 90 could be eliminated, provided that a receptacle (the recess 90 in the present embodiment) or other structure is provided for receiving or otherwise securing the closed end within the bore 24, provided that a structure is provided for securing the feet 117 to the plate 20, and provided there is enough clearance around the straights 114 to permit the straights 114 to be moved clear of the screw head 26 when the screw 22 is inserted into the bore 24.

As discussed, the retainer pilot 98 may be drilled into the lateral side L of the plate 20 and, therefore, has a circular cross-section. Accordingly, the feet 117 of the retainer 100 have a cross-sectional shape so that the feet 117 fit securely within the retainer pilot 98. That is, the feet 117 should be sized, in cross-section, to slide in and out of the retainer pilot 98 while not having a significant amount of play or looseness so that the retainer 100 rests firmly in positions over the top surface 29 of the screw head 26 for preventing back-out.

In one form of the retainer 100, the entire cross-section is generally circular, as can be seen in FIG. 7, so that the cross-section is substantially similar to that of the drilled retainer pilot 98. However, the retainer 100 need not have a uniform geometry such that the feet 117 and the straights 114 can have varying and/or different cross-sectional shapes.

Figure 12:
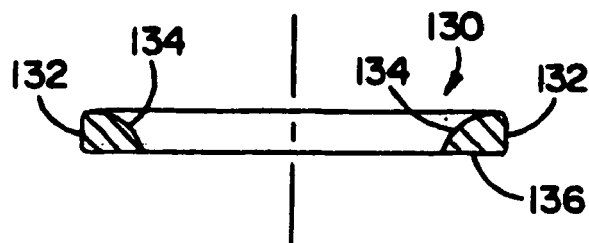
FIG. 12 is a cross-sectional view of another retainer.
Figure 13:
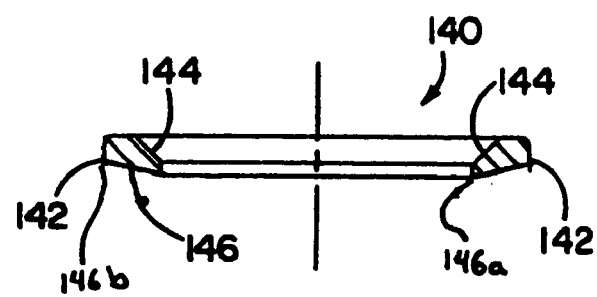
FIG. 13 is a cross-sectional view of another retainer.

In order to further retard the possibility of screw back-out, the retainer 100 may have an alternative cross-sectional geometry, as depicted in FIGS. 12 and 13, provided the feet 117 are properly fitted within the retainer pilot 98. In FIG. 12, a retainer 130 is depicted having straights 132 with arcuate surfaces 134 facing inward towards the opposite straight 132. The arcuate surfaces 134 allow the arcuate profile 82 of the screw head 26 to wedge the retainer 130 open when the screw 22 is being driven therethrough. The straights 132 further have a generally flat bottom surface 136 that contacts the top surface 29 of a screw head 26 and provides resistance against screw back-out if the normal clearance between the retainer 130 and screw head 26 is breached.

Similarly in FIG. 13, a retainer 140 is illustrated having straights 142 with a chamfer or cam surface 144 facing inward towards the opposite straight 142. It should be noted that the entire retainer 140, not simply the straights 142, may have the chamfer surface 144. The chamfers 144 allow the arcuate profile 82 of the screw head 26 to wedge the retainer 140 open when the screw 22 is being driven therethrough. Furthermore, the straights 142 may have a generally flat bottom surface, such as depicted in FIG. 12, or may have bottom surface 146 that rises from an inside edge 146a to an outside edge 146b. Again, the bottom surface 146 is generally spaced above the top surface 29 of a screw head 26 when the retainer 140 and screw 22 are fully secured in a bone plate 20. However, this bottom surface 146 provides further resistance against screw back-out since the displaced screw back-out force will tend not to open the retainer to allow the spring to escape.

Additionally, the screw head top surface 29 is preferably flat. A convex shape may promote or assist screw back out as the convex head may force the retainer 100 open. Alternatively, a concave shape may be employed for the top surface 29, though such may decrease depth provided for a driver recess 26a and, therefore, may make the screw head 26 more fragile when being driven.

Figure 14:
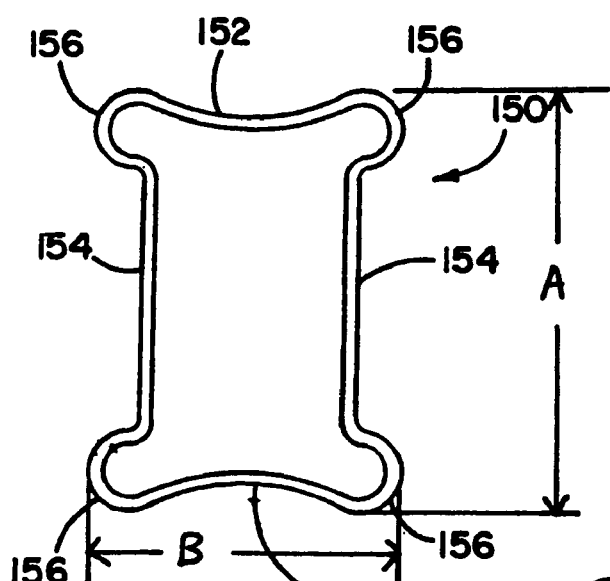
FIG. 14 is a plan view of another retainer.
Figure 15:
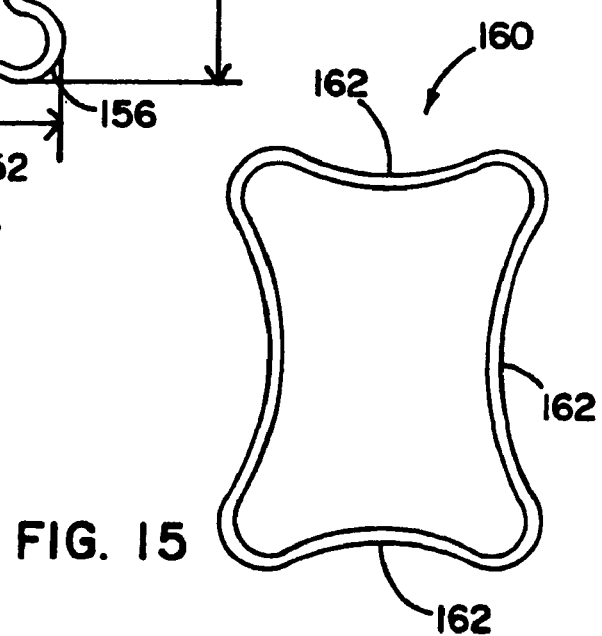
FIG. 15 is a plan view of another retainer.

Additional retainer forms having a closed-loop form are provided in FIGS. 14 and 15. Closed-loop retainers may be formed as a closed loop, such as by stamping, or may be a single length of material where the two ends are then joined, such as with butt-welding or crimping. Closed-loop retainers, as described herein, provide an additional benefit of more uniform expansion than the retainers with an open end because a greater portion of the spring deflects when a screw 22 is inserted.

A closed-loop retainer 150 includes oppositely located concave sections 152, two straights 154, and asymmetrical lobes 156 joining the concave sections 152 to the straights 154. As discussed above, the arcuate profile 82 of the screw head 26 may be driven against the straights 154 to force the retainer 150 open as the screw passes through, and the retainer 150 is resiliently elastic so that the retainer 150 generally returns to its undistorted shape after the screw head 26 has passed therethrough. The concave sections 152 allow the closed loop to be elastically compressed to reduce its overall size or footprint so that it may be inserted and seated within a bore 24. For this embodiment, the bore 24 may include the recess 90, as discussed above. Again, the recess 90 is provided to hold the retainer 150 in place, and to do so needs to provide a receptacle or structure for securing the lobes 156. As depicted, the retainer 150 has a larger longitudinal dimension A than lateral dimension B, such as is used with a dynamized bore 40. For a non-dynamized bore 42, the straights 154 would be shorter so that the retainer 150 may be placed within a generally circular recess 90.

As a further alternative, a retainer 160 may be provided having four concave sections 162 to allow for resilient compression of the retainer 160 for insertion, resilient expansion for allowing the screw head 26 to pass therethrough, and resilient contraction after the screw head 26 has passed therethrough so that the retainer rests on the top surface 29 of the screw head 26. For the closed loop retainers 150, 160, the tab recess 96 is not necessary.

It should be noted that, for retainers 150, 160 or other square, closed loop retainers used in non-dynamized bores, the bore may be generally square shaped.

Figure 16:
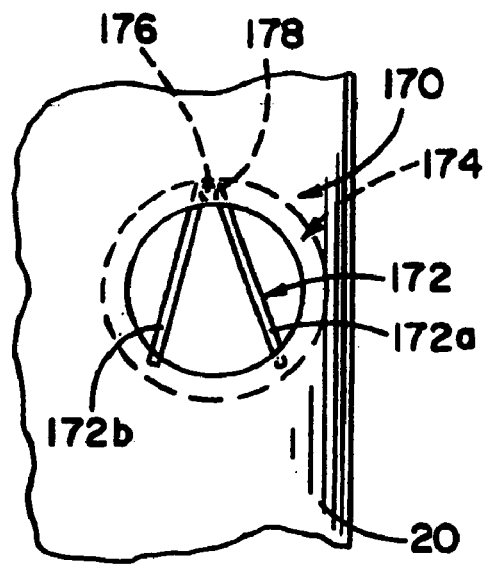
FIG. 16 is a plan view of another embodiment of a bore plate system including a bone plate having a bore and a retainer located therein.

In another form of the bone plate system 10 illustrated in FIG. 16, the plate 20 has a bore 170 and a retainer 172 secured therein for resiliently expanding to permit a screw head 26 to pass therethrough and contracting once the screw head 26 has passed therethrough, and for resting over the top surface 29 of the screw head 26. The retainer 172 is generally V-shaped with portions 172a, 172b, and is located within a recess 174 formed in the bore 170 in a manner similar to that described above. However, the recess 174 may also be a depression formed in the top surface 20a of the plate 20.

The retainer 172 is staked or anchored by an anchor mount 176 located at the apex or bend 178 of the V-shape of the retainer 172. The anchor mount 176 holds the retainer 170 to the plate 20, and may be a peg or pin inserted through the plate 20.

Like the previously discussed retainers, the retainer 172 is forced open by the arcuate profile 82 of the screw head 26 as the screw 22 is being driven between the portions 172a, 172b of the V-shape. Once the screw 22 has passed through, the portion 172a, 172b generally return to their previous position to rest on the top surface 29 of the screw head 26 and to prevent screw back out. As depicted, the bore 170 is a non-dynamized bore, and the retainer 172 is structured accordingly. For a dynamized bore, the bore 170 would be elongated and the retainer 172 would be structured to complement the dynamized bore as has been discussed above.

Figure 17:
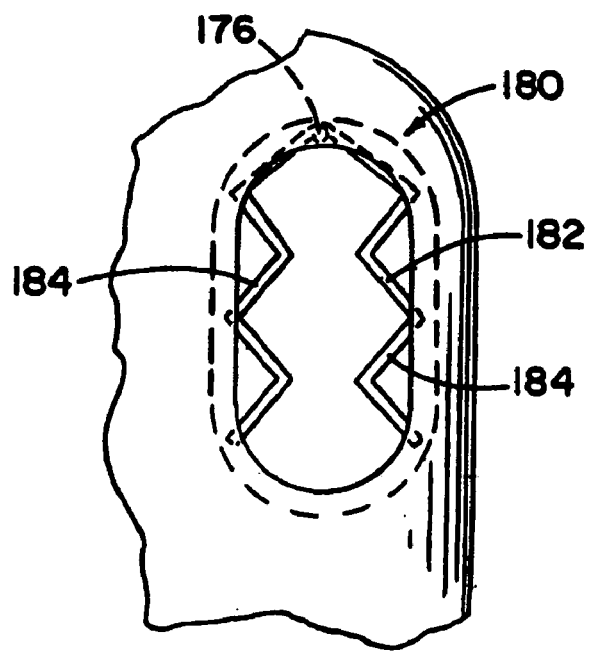
FIG. 17 is a plan view of another embodiment of a bore plate system including a bone plate having a bore and a retainer located therein.

In another form of the bone plate system 10, as illustrated in FIG. 17, the plate 20 has a bore 180 and a retainer 182 generally performing and being retained in the same manner as the bore 170 and retainer 172. However, the bore 180 is a dynamized bore, and the retainer 182 is structured in a complementary fashion. The retainer 182 is provided with two sets of opposed zig-zag arms 184. The screw 22 may be driven between these arms 184 in the same manner as for the straights of the retainers discussed above, or for the portions 172a and 172b for the V-shaped retainer 172. Once the screw 22 is driven through, the arms 184 of the retainer 182 generally return to their previous position, as is discussed above. This retainer 182 may also be formed as a closed loop like the retainer shown in FIG. 14.

Figure 18:
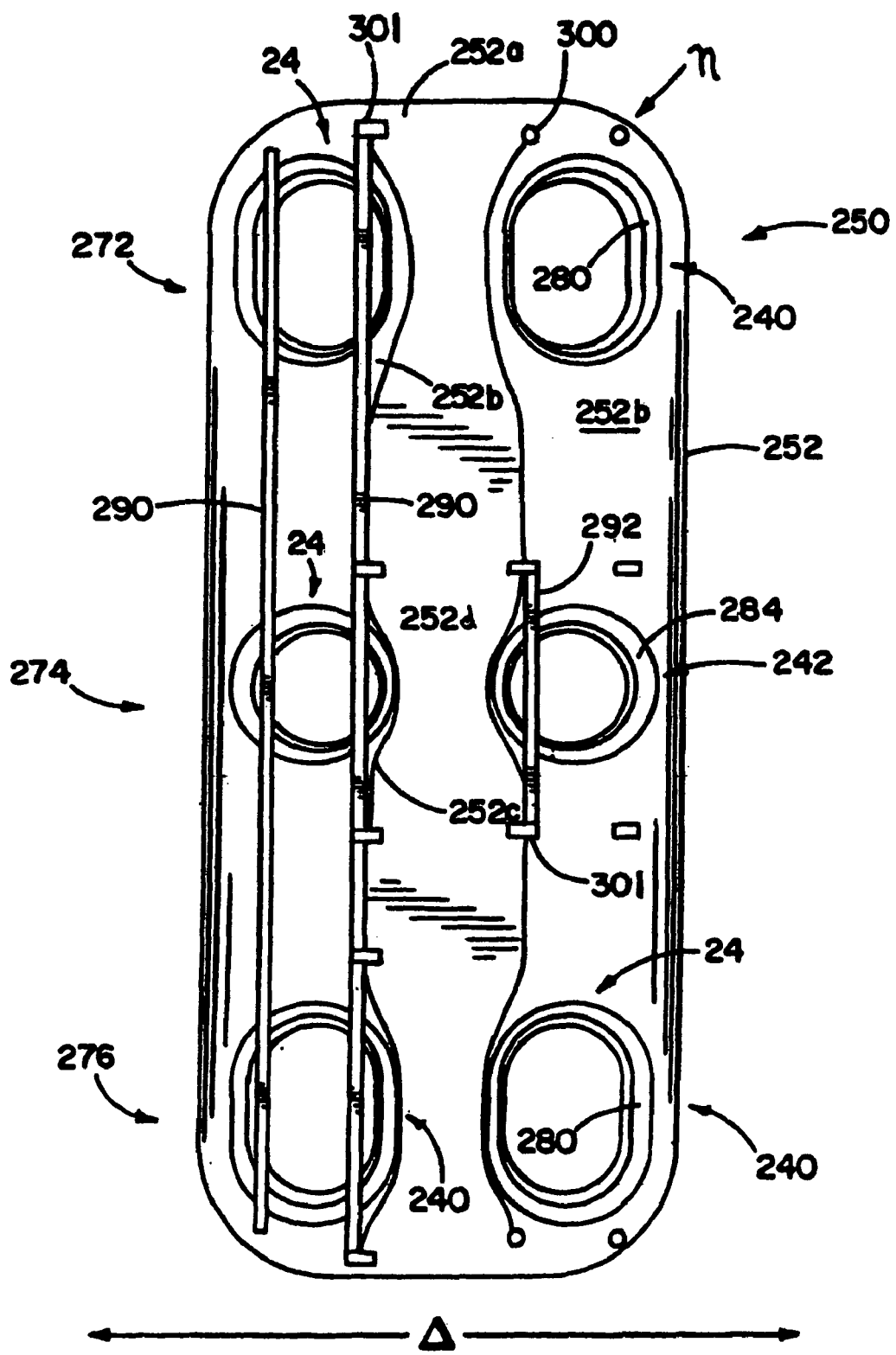
FIG. 18 is a plan view of another embodiment of a bone plate system including a bone plate having a bore and a retainer located proximate thereof.
Figure 24:
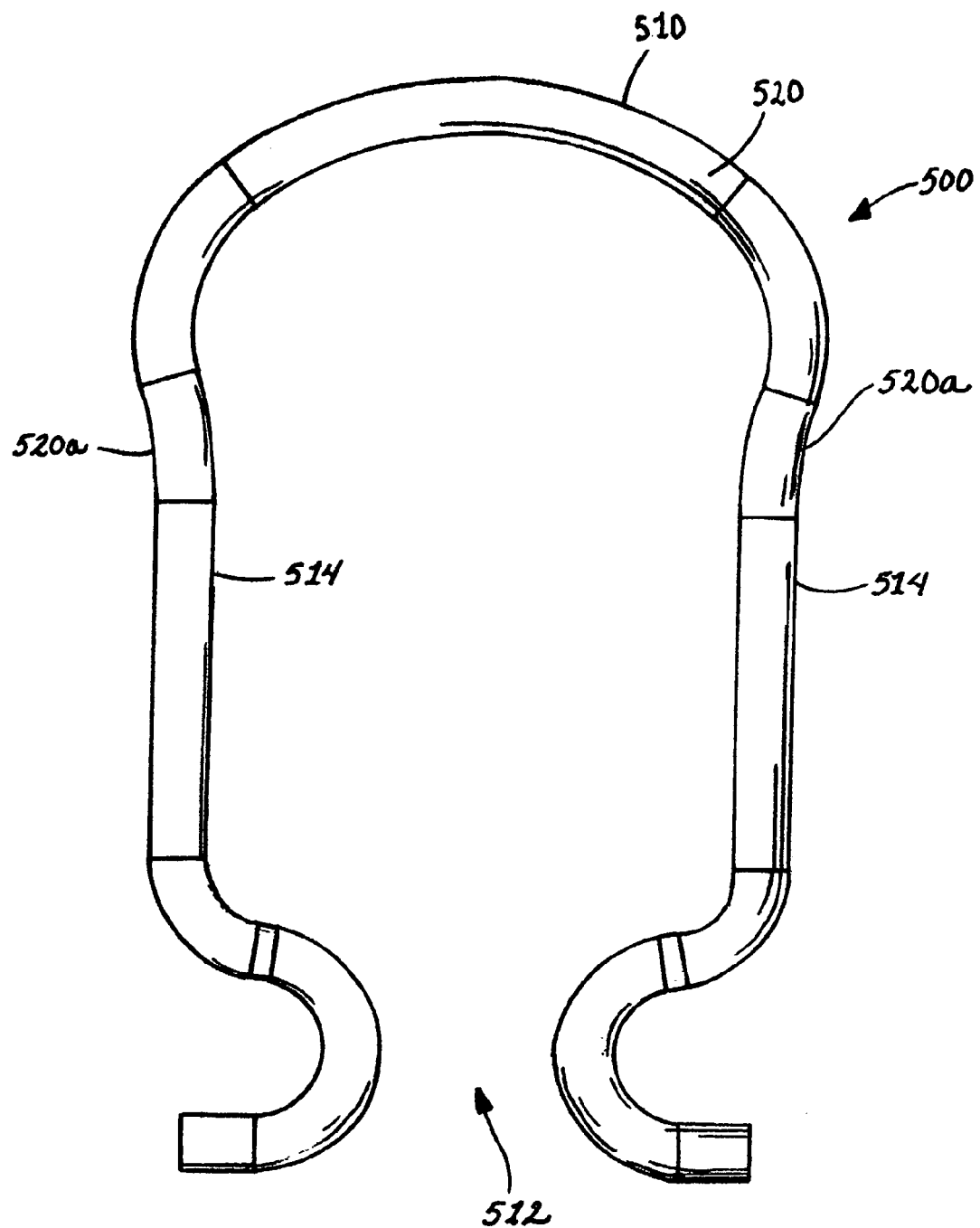
FIG. 24 is a second plan view of the retainer of FIG. 21.

Another form of a bone plate system 250, as illustrated in FIG. 18, includes a plate 252 having an uppermost tier 272, an intermediary tier 274, and a lowermost tier 276, each tier having a pair of bores 24 and, in the preferred embodiment, the uppermost and lowermost tiers 272, 276 having dynamized bores 240, and the intermediary tier having non-dynamized bores 242. The recess 90 discussed above for other embodiments is unnecessary for the plate 252, and, therefore, the bores 240, 242 have a continuous inner surface 280, 284 shaped for providing clearance for securing a polyaxial screw 22 at a selected angle (see FIG. 4), or shaped for mating with a non-polyaxial screw. Accordingly, the bores 240 allow a screw 22 located therein to translate relative to the plate 252, as described above, while the bores 242 do not permit such translation by a screw 22 located therein.

The plate 252 further include retainers in the form of a multi-bore retainer 290 which serves to impede screw back-out for more than one bore 240, 242 simultaneously. Alternatively, the plate 252 may include retainers in the form of a single-bore retainer 292 for impeding screw back-out for a single bore 24, such as 240, 242. Each retainer 290, 292 is generally a wire or generally straight member with a static position crossing through the path of a screw 22 to be located within one of the bores 240,242. Accordingly, as a screw 22 is driven into a bore 240,242, the arcuate profile 82 of the screw head 26 forces the retainer 290, 292 to move away from the center of the bore 240, 242 so that the screw head 26 may pass therethrough. Once the screw head 26 has passed by the deflected retainer 290, 292, the retainer 290, 292, returns to the static position so as to rest over the top surface 29 of the screw head 26 to prevent back-out thereof.

The retainers 290, 292 are elastically resilient with minimal or no plastic deformation due to being deflected. That is, the retainers 290, 292 elastically deform in order to be deflected from the static position, illustrated in FIG. 18, to permit the screw head 26 to pass therethrough. Once the screw head 28 passes by the retainers 290, 292, the elasticity permits the retainers 290, 292 to contract or return generally to the static position.

The retainers 290, 292 may be a single filament wire with any cross-section. Alternatively, the retainers 290, 292 may be a multi-filament, wound wire or a biocompatible polymeric material.

Preferably, the retainers 290, 292 deflect more easily in a direction generally along a top surface 252a of the plate 252 than in a direction orthogonal to the top surface 252a. A force applied by a screw 22 attempting to back out from the bore 240, 242 will force the retainers 290, 292 outwardly from the plate 252 for the portion proximate to the screw head 26. A retainer 290, 292 of constant cross-section and constant material will deflect laterally due to the screw head 26 passing thereby, and the retainer 290, 292 will equally deflect outward from the plate 252 when under equal force.

Accordingly, the retainers 290, 292 may be provided with a structure so that the retainer 290, 292 may deflect elastically an appropriate amount when the screw head 26 passes therethrough and so that the retainer 290, 292 resists outward deflection when under stress. For example, the retainer 290, 292 may have a first dimension in a lateral direction, represented by arrow $\Delta$, and a greater dimension in the direction orthogonal to the plate top surface 252a, that is, outwardly from the plate 252. Accordingly, a greater force is required to deflect the retainer 290, 292 outwardly, such as would happen from screw back-out, than is required to deflect the retainer 290, 292 to permit passage of a screw head 26.

The retainers 290, 292 are generally located at or near the plate top surface 252a. In one form, the retainers 290, 292 may be located on the plate top surface 252a. However, as being located on the top surface 252a may interfere with or abrade living tissues located thereagainst, it is preferred that at least a portion of the retainer 290, 292 is located lower than a highest portion of the plate top surface 252a.

In certain forms, the retainer 290, 292, may be entirely positioned within and below the plate top surface 252a, may be partially positioned within the top surface 252a, or may be within yet flush with the plate top surface 252a. Accordingly, the top surface 252a provides a excavated or depressed portion or region 252b located proximate to the bores 240, 242 such that the deflection of the retainer 290, 292 is permitted though generally localized by a wall 252c. In other words, the top surface 252a of the plate 252 may have a height in a region 252d with respect to the top of the retainers 290, 292 such that the top surface 252a principally contacts the surrounding living tissues. In order to permit the retainers 290, 292 to deflect along but at least partially below the surface 252a, the depression 252b is formed, and the wall 252c is formed between depression 252b and the region 252d. The wall 252c localizes the deflection of the retainer 290, 292 while permitting the entire length of the multi-bore retainer 290 to stretch elastically to permit the screw 22 to be driven into the plate 252.

The retainers 290, 292 may be connected to the plate 252 in a variety of manners. For instance, it may be possible to simply glue the retainers 290, 292 to the top surface 252a. However, it is preferred that the retainers 290, 292 are connected in a more mechanical manner.

One manner for mounting the retainers 290, 292 is to provide a port or bore 301 in the plate for each end of the retainers 290, 292. The retainers 290, 292 may be fed into the port 301 from the top surface 252a to a bottom surface (not shown) and tied or otherwise secured at the bottom surface. The retainers 290, 292 may be fed into the port 301 and soldered or welded into place, or crimped therein either by deformation directly at the port 301 or inward from a side of the plate, as represented by the arrow $\eta$. Furthermore, the plate 252 may be provided with a physical structure (not shown) located on the top surface 252a, the retainers 290, 292 may be placed in the structure, and the retainers 290, 292 may be secured in the structure either by deforming the structure or by adding another securing member, such as a clip or crimp for clamping the retainer 290, 292 therein.

Referring now to FIGS. 19 and 20, a further embodiment of a retainer 400 and bone plate 402 is depicted. As can be seen, the plate 402 has dynamized bores 404 and non-dynamized bores 406. The number and orientation of the dynamized and non-dynamized bores 404,406 may vary in the manner described for the above-discussed embodiments, and the retainer 400 may be utilized singly or in tandem with another similar retainer in conjunction with one or more bores 404, 406. The retainer 400 may be constructed similarly to the retainers 290, 292, and may be a continuous loop such that the retainer passes over a bore, such as 404, twice.

The retainer 400 is secured to the plate 402 by curved or undulating paths 410. The paths 410 are inset into the top surface 402a of the plate 402 and are undercut at their lowest point 412, as can be seen in FIG. 20. Each path has preferably a first apex 416, a second apex 418, and a third apex 420, such that the retainer 400 strung therein is captured. Alternatively, the ends 430 of the retainer 400 may be captured or secured, as has been discussed above.

A further embodiment of an retainer 500, depicted in FIGS. 21-24, may be used with the bone plate 20 similar to the retainer 100, as described above. More specifically, the retainer 500 may be in a plurality of forms, wherein a first form, depicted in FIGS. 21-24, may be used with a dynamized bore 40. The retainer 500 includes two side portions 514 corresponding to the straights 114 of the retainer 100. In other forms, the length of the retainer 500 may be increased, such as by increasing the length of side portions 514, to provide various retainers corresponding to longer dynamized bores, depending on the amount of subsidence desired. Excepting the length, the various forms of the retainer 500 are generally identical in all other respects. Each retainer 500 has a closed end portion 510 and an open end portion 512 opposite the closed end portion 510. The retainer 500 is held within the plate 20 by the recess 90, and closed end portion 510 is received directly within the recess 90. By decreasing the length of retainer 500, it may be used with a non-dynamized bore, such as bore 42.

Prior to the screw 22 being inserted into the plate 20, the straights 514 of the retainer 500 are shaped as is depicted and are in a static position. The position within the bore 24 of the retainer 500 is generally that as depicted in FIG. 9 for the retainer 100. The side portions 514 extend through the bore 24 to interfere with the path of the screw head 26 to contact the seat surface 78. As the screw 22 is driven into the bone 12, the screw head 26 contacts the side portions 514. As the screw 22 continues into the bone 12 and plate 20, the arcuate profile 82 of the screw head 26 cams against the side portions 514 and forces the side portions 514 away from each other and into the recess 90. Once the screw head 26 passes through and below the retainer 500 and its side portions 514, the retainer 500 generally returns to its static position, such as that prior to insertion of the screw. As discussed above, the screw 22 is seated in the bone 12 and plate 20 so that the retainer 500 is over the top surface 29 of the screw head 26 to prevent screw back out.

Like the retainer 100, the retainer 500 is preset in the bores 24. The closed end portion 510 of the retainer 500 includes an arcuate segment 520, though it could include arms 120 joined by the elbow 122 described above for retainer 100. The arcuate segment 520 provides a greater amount of the retainer 500 being received by the recess 90, prospectively enhancing stability and securement to the retainer 500 within the plate 20.

The arcuate segment 520 joins the side portions 514. So that the side portions 514 are positioned to cross the bore 24, ends 520a of the arcuate segment 520 meeting with the side portions 514 are directed such that the arcuate segment 520 curves greater than 180 degrees. In other words, the arcuate segment 520 curves inward so that the side portions 514 have a narrower overall width for crossing the bore 24. Although the depiction of the retainer 500 presents the side portions 514 as generally straight and generally parallel to each other, the side portions 514 may be curved and/or skew to each other such that the distance between them increases as the side portions 514 extend away from the arcuate segment 520, and, thus, the retainer 500 may be generally bowed-in.

The open end portion 512 includes two arms 521 each terminating with a leg 516 separated by a gap 518. Each leg 516 has a straight portion in the form of a foot 517a, 517b, aligned along an axis 517c generally orthogonal to an axis 500a of the retainer 500. As for the retainer 100, the retainer 500 may be inserted within the bore 24 by compressing the open end portion 512 to bring the legs 516 together and reduce or eliminate the gap 518. The closed end portion 510 is then inserted into the recess 90, and the open end portion 512 is then inserted into a tab-shaped recess 96, as depicted in FIGS. 5A and 5B. The retainers 500 are elastically resilient so that the retainer returns to its natural shape when released, and the retainer 500 may cooperate with the screw head 28. Again, the securement and operation of the retainer 500 is similar to that of the retainer 100, as described above.

In addition, the retainer 500 is depicted as generally circular in cross-section. Similar to the above discussion regarding, e.g., FIGS. 12 and 13, the retainer 500 may have a non-uniform geometry, while the feet 517a and 517b are to be properly fitted within the retainer pilot 98. For example, the retainer 500 may have upwardly facing arcuate surfaces corresponding to the arcuate surfaces 134 of retainer 130 in FIG. 12 to facilitate a cam-wedge action between the screw and the retainer 500 when the screw 22 is being driven therethrough. The retainer 500 may also have downwardly facing flat surface corresponding to the bottom surface 136 of the retainer 130 for providing further resistance against screw back-out. Alternatively, the retainer 500 may have a upward, inwardly facing chamfer surface corresponding to the cam surface 144 of retainer 140 in FIG. 13. Again, the retainer may also have a bottom surface corresponding to the bottom surface 146, rising from an inside edge 146a to an outside edge 146b to provide further resistance against screw back-out.

Figure 27:
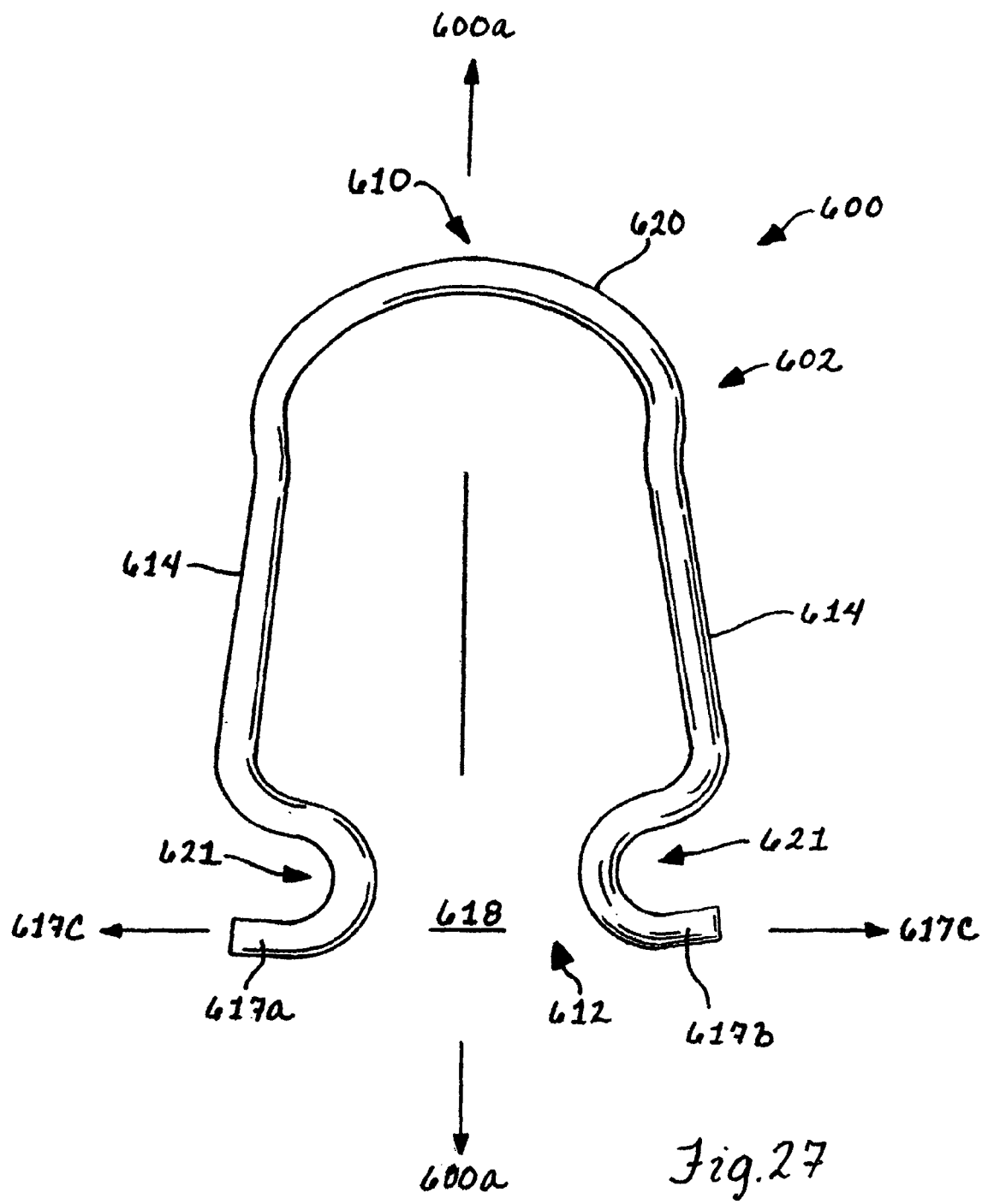
FIG. 27 is a plan view of a second form of the retainer of FIG. 25.

Referring now to FIGS. 25-27, forms of a further embodiment of a retainer 600 are depicted. In FIGS. 25 and 26, the retainer 600 is depicted in a first form 601 for use with a non-dynamized bore 42, while in FIG. 27 the retainer 600 is depicted in a second form 602 for use with a dynamized bore 40. The retainer 600 includes two side portions 614 corresponding to the straights 114 of the retainer 100. In other forms, such as second form 602, the length of the retainer 600 may be increased, such as by increasing the length of side portions 614 in the same manner side portions 514 of the retainer 500 may be increased, to provide retainers 600 with various lengths corresponding to dynamized bores providing for varying amounts of permitted subsidence. As with the retainer 500, the various forms of the retainer 600 are generally identical in all respects other than the lengths. Each retainer 600 has a closed end portion 610 and an open end portion 612 opposite the closed end portion 610. The retainer 600 is held within the plate 20 by the recess 90, and closed end portion 610 is received within directly within the recess 90.

In FIGS. 25-27, the retainer 600 is depicted in a shape prior to insertion in the recess 90. When inserted into a plate 20, the position within the bore 24 of the retainer 600 is generally that as depicted in FIG. 9 for the retainer 100. That is, the side portions 614 are compressed so as to be generally parallel and to extend through the bore 24 to interfere with the path of the screw head 26 to contact the seat surface 78. As the screw 22 is driven into the bone 12, the screw head 26 contacts the side portions 614. Similar to that discussed above, the screw 22 continues into the bone 12 and plate 20, the arcuate profile 82 of the screw head 26 cams against the side portions 614 and forces the side portions 614 away from each other and into the recess 90. Once the screw head 26 passes through and below the retainer 600, the side portions 614 return to the generally parallel position, and the screw 22 is seated so that the retainer 600 is over the top surface 29 of the screw head 26 to prevent screw back-out.

Like the retainers 100 and 500, the retainer 600 is preset in the bores 24. Like for retainer 500, the closed end portion 610 of the retainer 600 includes an arcuate segment 620 providing a greater amount being received by the recess 90, prospectively enhancing stability and securement to the retainer 600 within the plate 20.

The arcuate segment 620 joins the side portions 614 such that the retainer 600 is configured similarly to retainer 500. The arcuate segment 620 curves greater than 180 degrees, that is, curves inward, so that the side portions have a narrower overall width for crossing the bore 24 and for interfering with a seated screw 22.

The retainer 600 has a geometry similar to retainers 100 and 500. That is, the open end portion 612 has two arms 621 each terminating with a leg 616 separated by a gap 618. Each leg 616 has a straight portion in the form of a foot 617a, 617b. When positioned within a bore 24, the feet 617a, 617b are aligned along an axis 617c generally orthogonal to an axis 600a of the retainer 600, and, as described, the straight portions 614 are generally parallel. However, as depicted, the retainer 600 is not inserted and, therefore, the feet 617a, 617b are not aligned along the axis 617c. The retainer 600 may be inserted in to the recess 90 in the same manner as described above for retainers 100 and 500.

Though the retainer 600 is depicted as generally circular in cross-section in FIG. 26, the retainer 600 may have a non-uniform geometry, as described above for retainer 500.

Referring now to FIGS. 28-40, forms of a further bone plate 700 are depicted. More specifically, a bone plate 701 is depicted in FIGS. 28-36, and a bone plate 702 is depicted in FIGS. 37-40. The bone plates 701 and 702 are generally identical in operation and features. However, the plate 701 is generally planar or flat, while plate 702 is curved, as can best be seen in comparing of FIG. 31 with FIG. 40 and in comparing FIG. 29 with FIG. 38. The curvature of the plate 700 will be described in greater detail below.

As described above for plate 20, the plate 700 is provided with representative pairs of bores 24 for receiving screws 22. Each bore 24 has an inner surface 770 and a lowermost portion 770a defining a throughbore 772 corresponding to the above described interior surfaces 50, 60, 70, lowermost portions 50a, 60a, 70a, and throughbores 52, 62, 72 of the dynamized and non-dynamized bores 40, 42. Though, that the plate 700 is depicted with non-dynamized bores 42 only, it should be noted that the plate 700 may also have dynamized bores 40, with a geometry as described above for plate 10. When a screw 22 is secured within the bore 24, the screw head 26 secures against the inner surface 770, and the screw shank 28 extends from the throughbore 772 and is secured within the bone 12.

In one embodiment, the plate is provided with two tiers of paired bores in the form of non-dynamized circular bores at one end and a pair of elongated dynamized bores at the other end. A three tier embodiment having a pair of dynamized bores at each end and non-dynamized bores in the middle may also be provided. In another embodiment, a four tier plate having a pair of dynamized bores sized for about 2 millimeters of movement along the spine axis is followed by circular non-dynamized holes, followed by dynamized holes sized for about 1.25 millimeters of movement, followed by a pair of dynamized bores sized for about 2.5 millimeters of movement as illustrated in FIG. 82. Another possible embodiment consists of a five tier plate with a pair of dynamized bores at the ends sized for 2.5 millimeters of movement, with adjacent pairs of dynamized bores sized for 1.25 millimeters of movement, and a pair of non-dynamized holes in the center as shown in FIG. 83.

As stated above, the screw 22 is preferably polyaxial and may be driven through the bore 24 at a selected angle. Therefore, the screw head 26 is larger than the screw shank 28 and the throughbore 772, and the screw shank 28 is smaller than the throughbore 772. The inner surface 770 includes a brace surface 774 within which the bridge 27 of the screw 22 is positioned, the bridge 27 being smaller in diameter than the bore 24 within the brace surface 774.

As for plate 20, the brace surface 774 transitions to a seat surface 778 at a shoulder position 780. When the screw 22 is secured in a bone 12, the screw head 26 rests against the shoulder position 780, and the arcuate profile 82 of the screw head 26 seats against the shoulder 780 at the selected angle. The neck or bridge 27 is sized relative to the bore 24 within the brace surface 774 to allow the proper amount of angulation for the screw 22 to be pivoted for a selected angle.

As for the shoulder 80, the shoulder 780 may have a number of constructions, such as simply an edge, or may be a chamfer, or the seat surface 778 and screw head 26 may be spherical with closely matched diameters so that the screw head 26 may polyaxially slide against the seat surface 778 for driving the screw 22 in the bone 12 at the selected angle.

As discussed, a retainer is preferably provided for each bore 24. In the same manner as for plate 20, the plate 700 may include a recess 790 above the seat surface 778 and extending around the inner periphery of the inner surface 770. A portion of the retainer may be secured or located in the recess 790. The screw head 26 has height H1 (see FIG. 4) that is less than a height H3 of the seat surface 78. The height differential between H1 and H3 permits the screw 22 to pivot a predetermined amount before the screw head top surface 29 interferes with the retainer when it is pivoted. Accordingly, it is preferred that the top surface 29 of the screw 22 is generally positioned below a lower edge 790a of the recess 790 when the screw 22 is secured straight through the bore 24, or is generally coincident with the lower edge 790a when the screw is secured at a selected pivoted angle.

Above the recess 790, the inner surface 770 has a receiving portion 792 that terminates at a top edge 721 meeting with a top surface 700a of the plate 700. For a non-dynamized bore 42, each described portion of the inner surface 770 is generally circular in shape, while for a dynamized bore 40 the inner surface 770 has straight sides, as described above.

Figure 31:
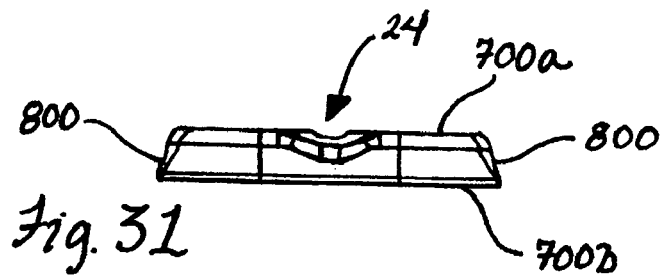
FIG. 31 is an end view of the bone plate of FIG. 28.
Figure 32:
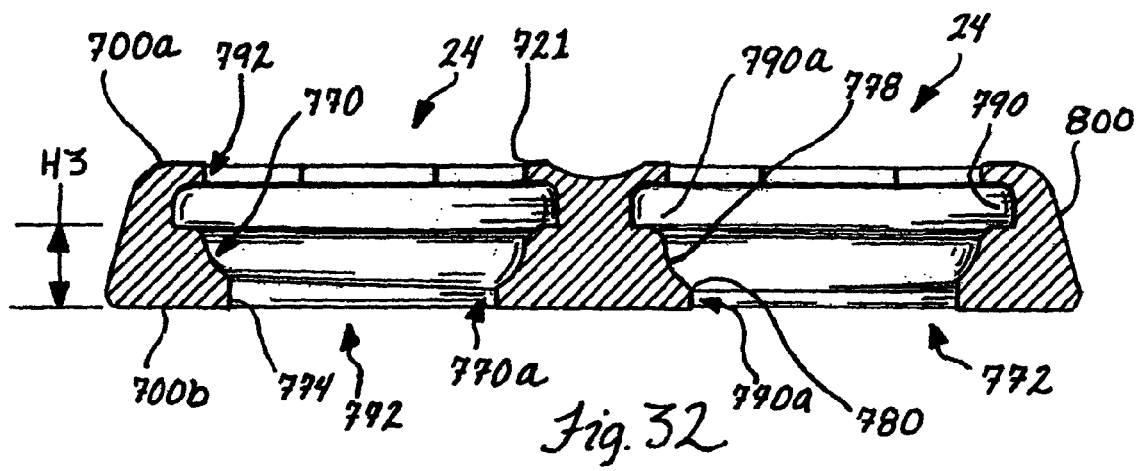
FIG. 32 is a cross-sectional view of the bone plate of FIG. 28 taken through the line 32-32.
Figure 34:
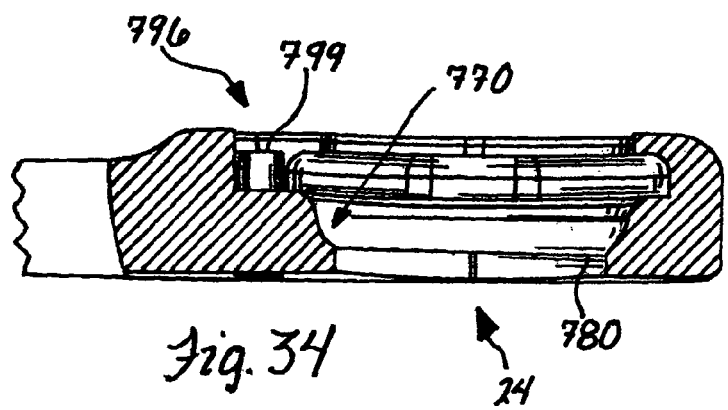
FIG. 34 is a fragmentary cross-sectional view of a bore of the bone plate of FIG. 30.
Figure 36:
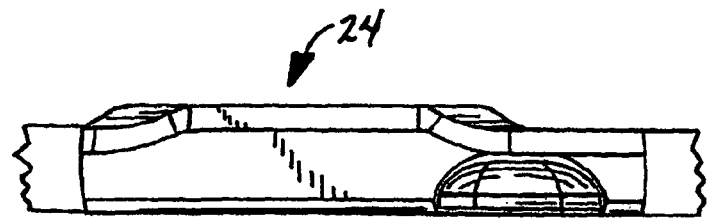
FIG. 36 is a fragmentary side elevation view of the bone plate of FIG. 29.

As can be seen in FIGS. 31 and 32, side edges 800 of the plate 700 are angled inward from the bottom surface 700b to the top surface 700a. This reduces the profile of the plate and the likelihood of flesh becoming irritated from contact with the edges of the plate 700 in the lateral direction.

Figure 33:
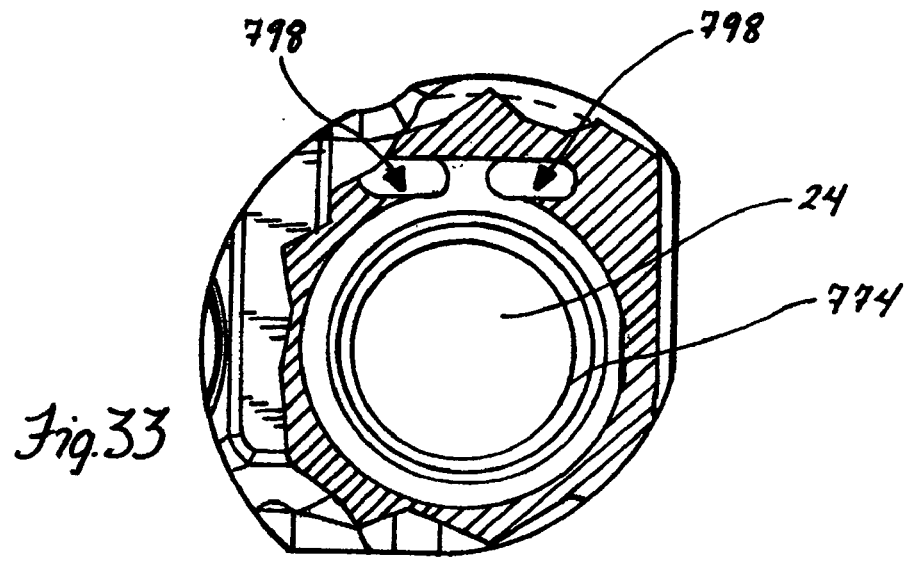
FIG. 33 is a fragmentary cross-sectional view of the bone plate of FIG. 29 along the line 33-33.
Figure 35:
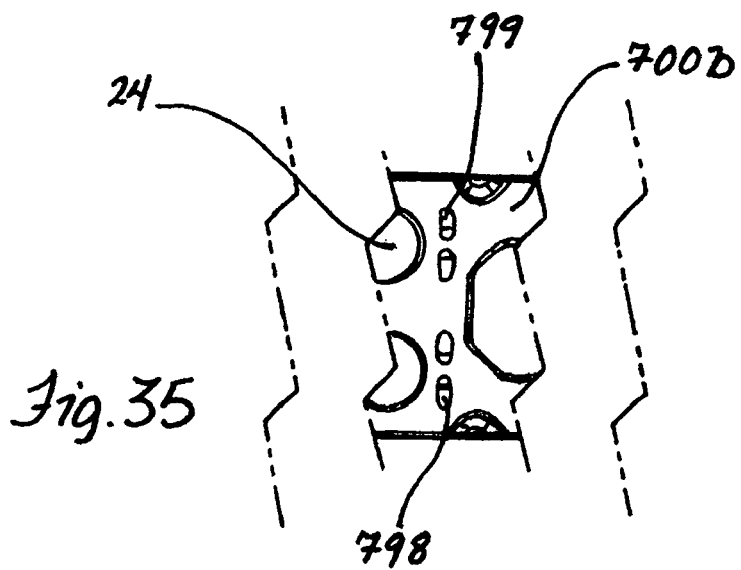
FIG. 35 is a fragmentary bottom plan view of the bone plate of FIG. 28.

The plate 700 includes a tab shaped recess 796, similar to tab recess 96 of plate 20. However, instead of including retainer pilot 98, the plate 700 may include access ports 798, as best seen in FIGS. 28, 33-35 and 37. More specifically, the access port 798 may be cut from the bottom surface 700b towards the top surface 700a to a depth coincident with the recess 790. FIG. 33 illustrates a bore 24 of the plate 700 with a portion removed laterally through the recess 790 such that the access port 798 is visible from a top view of the plate 700. In comparison, FIG. 28 shows the plate 700 without the portion removed such that the access port 798 is partially obscured. A further comparison with FIG. 35 shows the bottom side 700b of the plate 700 such that the access port 798 is fully illustrated, and an interior top surface 799 of the recess 790 proximal to the tab recess 796 can be seen through the access port 798 (see also FIG. 34).

In use, the surgeon may initially locate the bone plate 20 against the bones 12. The bone plate 20 includes windows 200 which permit viewing of a fusion site, such as a graft in place of a spinal disc 14, located between the tiers 30, 32, 34. The windows 200 are preferably square or diamond shaped and oriented so that corners 202 are aligned with the longitudinal and lateral directions of the bone plate 20. In this manner, the windows 200 may extend to a height and a width such that the extent of the permitted view therethrough includes a portion directly between the various bores 24. Alternatively, the window 200 may be an oval so that portions of the window 200 can provide a view located between the bores 24, or any other shape. More specifically, the windows 200 extend so that ends 13 of the vertebrae 12 can be seen such that a surgeon can directly examine fusion sites at the ends 13. By providing a window 200 as described, a surgeon may use radiography to view the fusion site without the plate 20 itself obscuring the view. The size of the window 200 is predetermined and is based on the structural necessities of the plate 20, such as the size, strength and fatigue life of the plate. Although not shown, each window 200 may have a rib or extension spanning the window 200. The rib may include an additional bore for receiving a screw which may secure to a bone or an implant such as a graft. These same features may, also, be present or utilized with bone plates 252, 700.

As a further alternative, a window 200a may be provided as is shown with plate 700 in FIG. 28. In this form, the window 200a has an irregular shape including arcuate portions and straight portions such that the window 200a is configured such as to not impede the structural integrity of the plate 700 while further attempting to maximize the view available therethrough to a surgeon.

The bottom surface 20b of the bone plate 20 (FIG. 4) may include spikes or protrusions (not shown) for securing the bone plate 20 to at least one bone 12. In the depicted embodiments, the non-dynamized bores 42 are located on the intermediary tier 32. Therefore, the bone plate 20 is not to shift relative to the middle bone 12b with non-dynamized bores 42. In order to promote this, the protrusions are provided on the bottom surface 20b of the bone plate 20 in a region proximal to and contacting the middle bone 12b. In various embodiments, the spikes or protrusions may be provided between the bone plate 20 and any bone to which the plate 20 is not to shift relatively, that is, any bone secured to the plate 20 with non-dynamized bores 42.

Once the surgeon has positioned the plate 20 over the bones 12, assisted by the windows 200, the plate with spikes may be manually pushed or tapped into the bone to secure the plate 20 thereto. Alternatively, the fixing of the plate 20 to a bone with bone anchors, such as screws 22 in the non-dynamized bores 42, may force the spikes into that bone. These same features may be present or utilized with each of the bone plates described herein.

Figure 40:
FIG. 40 is an end view of the bone plate of FIG. 37.

The bone plate of the bone plate system, in its various embodiments, is often secured to bones or bone fragments 12 that have a curved surface facing the bone plates. As can be seen in FIGS. 2, 4, and 40, for instance, the plates 20, 700 also have a curved or arcuate profile for following such a curved surface of the bone 12. In addition, spinal vertebrae include characteristic bone protrusions (not shown) or randomly placed incongruities over which the bone plates would commonly be secured.

In order to provide greater accommodation for the spinal bone protrusions, the bone plates 20, 700, for instance, have one or more grooves or valleys 20c, on the bottom surface 20b, 700b of the respective bone plates 20, 700. It should be noted that the bone plates may include grooves or valleys oriented in any direction along the bottom surface 20b, 700b, for instance, of the plate. In other words, the bone 12 may have a distinctly uneven surface, and the valley 20c is provided so that localization of pressure at specific points between the bone 12 and the plate 20,700 is reduced or minimized, thus reducing the likelihood of bone necrosis. In addition, the valleys 20c are preferably formed so that the principal points of contact between the plate 20,700 and the bone 112 are controlled to be generally in the region of the bores 24. Therefore, the positioned plate 20,700 may rest in a balanced position against the bones 12 and may tend to avoid rocking caused by an unbalanced or uneven positioning.

Illustrated in FIGS. 44-52 is a further form of a bone plate system 1000 including a bone plate 1002 and retainers 1004 for retarding the likelihood of backout by a bone screw 22. The plate 1002, as depicted, includes bores 24 in the form of non-dynamized bores 1042 similar to bores 42, the bores 1042 being paired in three transverse tiers 1006a, 1006b, 1006c for securing to three vertebrae 12a, 12b, 12c, as is depicted in FIG. 1 and described above. Although depicted as non-dynamized, one or more of the bores 1042 could alternatively be dynamized, with geometry similar to that described above for plate 10. Additionally, the plate 1002 may be provided with only two tiers of bores 24, or more tiers than three. As depicted, the plate 1002 includes windows 200a as shown and described for plate 700 in FIG. 28.

Similarly to plates 20 and 700, the bores 24 of plate 1002 have an inner surface 1010 and a lowermost portion 1012 defining a throughbore 1014 with a brace surface 1016 corresponding to the above described interior surface 60, lowermost portion 60a, throughbore 62, and 74 of the non-dynamized bores 42. When inserted into the bores 24 and secured therein, the screw head 26 secures against the inner surface 1010, and the screw shank 28 extends from the throughbore 1014 for securing within the bone 12.

The cooperation between the screws 22 and the bores 24 may be polyaxial or fixed, as has been described. A polyaxial screw 22 may be inserted into the bone 12 at a desired angle relative to the plate 1002, and the bridge 27 of the screw 22 is smaller in diameter than the bore 24 within the brace surface 1016. Alternatively, a fixed screw may be desired, which may include a screw shank 28 having a neck or bridge 27 having a substantially cylindrical shape that closely fits into and against the substantially cylindrical brace surface 1016 of the lowermost portion 1012. As has been described above for other bone plate embodiments, the brace surface 1016 forms a shoulder 1022 with a seat surface 1024 corresponding to the seat surface 778 and shoulder 780 of plate 700.

Figure 45:
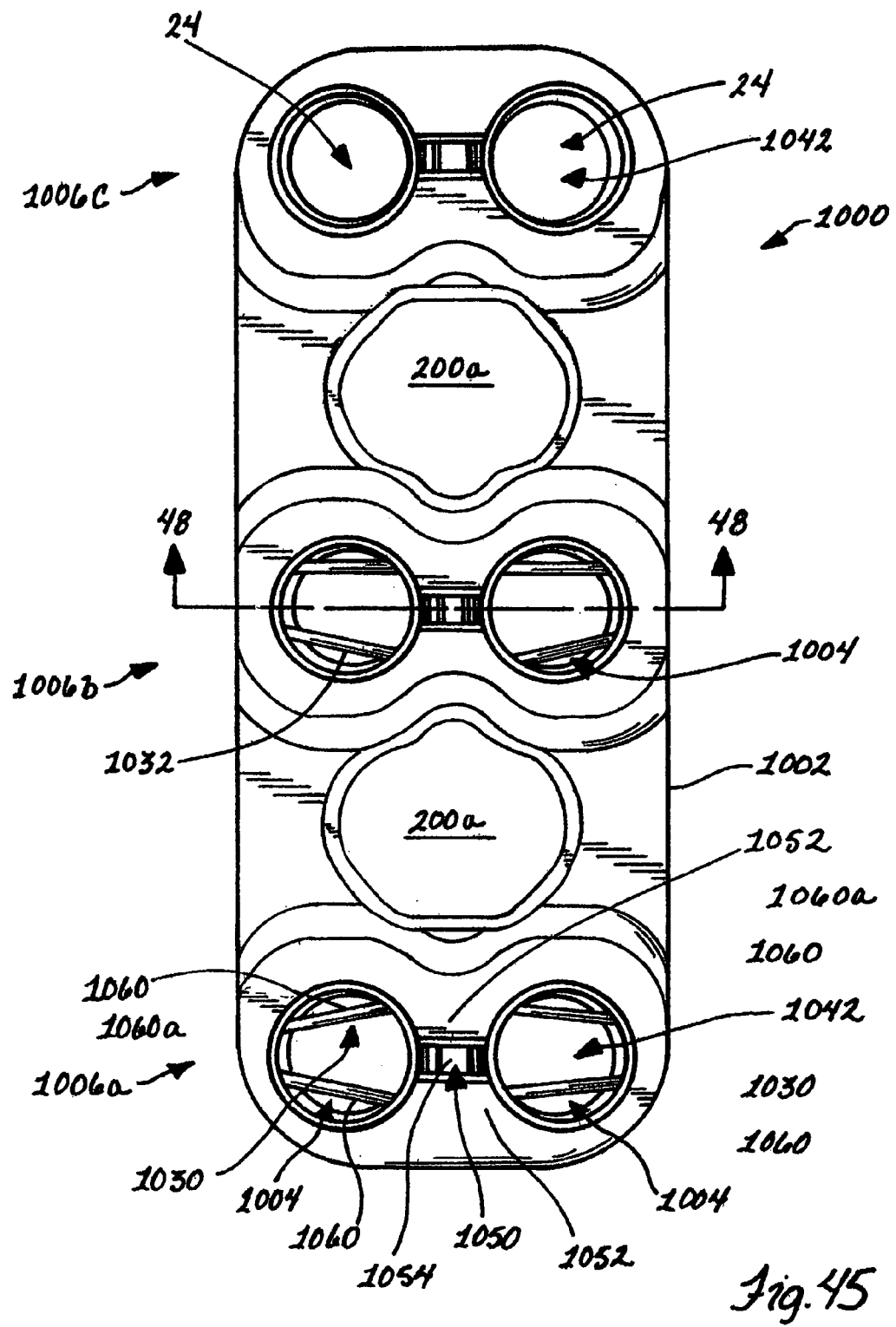
FIG. 45 is a top plan view of the bone plate of FIG. 44 showing three levels having non-dynamized bores and showing a retainer operating in a single hole and a retainer operating in a pair of holes of one of the levels.
Figure 48:
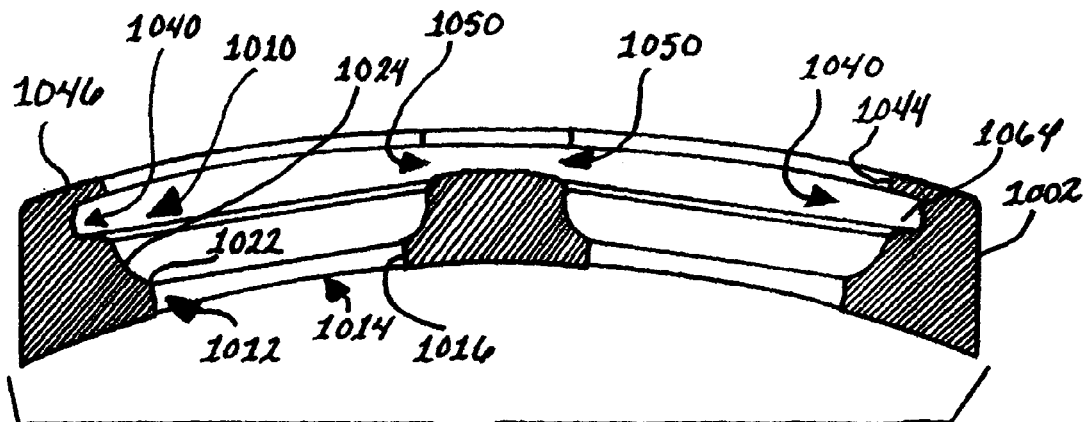
FIG. 48 is a cross-sectional view of the bone plate taken through the line 48-48 of FIG. 45.
Figure 49:
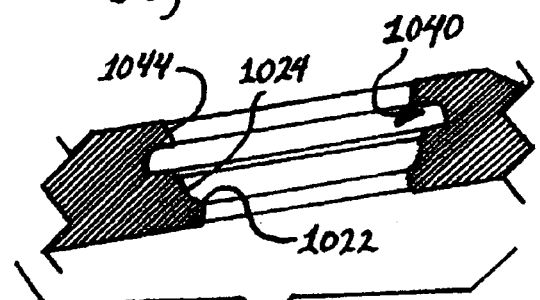
FIG. 49 is a cross-sectional view of the bone plate taken through the line 49-49 of FIG. 46.

With specific reference to FIGS. 45, 51, and 52, two similar forms of the retainer 1004 are depicted. FIG. 51 depicts a preferred somewhat U-shaped retainer 1030 for being located within a single bore 24 to prevent backout of a single screw 22 located in the bore 24. In comparison, FIG. 52 illustrates a retainer 1032 for preventing backout of a pair of screws 22 located in adjacent bores 24, either of the same tier 1006 or spanning across tiers 1006. In FIG. 45, the plate 1002 presents the respective position of each retainer 1030, 1032, though it is expected that the plate 1002 is provided with one form of the retainer 1004 or the other. The retainers 1004 are generally wire-like and have a cross-sectional geometry as described above.

As for previously described plates, recesses 1040 for receiving the retainers 1004 and extending around the inner periphery of the inner surface 1010 are included above the seat surfaces 1024. Preferably, at least a portion of the retainer 1004 is positioned in the recess 1040 at a height greater than a height of the screw head 26 so that the difference between the heights permits the screw 22 to pivot a predetermined amount before the screw head top surface 29 interferes with the retainer 1004, as has been described above.

The inner surface 1010 also has a receiving portion 1044 spanning between the recess 1040 and a top plate edge 1046. Non-dynamized bores 42 may include a generally circular receiving portion 1044, whereas the dynamized bores 40 may have generally straight sides, as described above.

Each bore 24 of the plate 1002 includes a recess 1050, similar to the tab-shaped recess 796 described for plate 700. However, the tab-shaped recesses 796 are oriented generally along the longitudinal axis of the plate 700. For plate 1002, recesses for adjacent bores 24 may be joined to form a single recess 1050. Preferably, the recesses 1050 are laterally oriented so that a pair of bores 24 of the same tier 1006 are provided with the single recess 1050. Above the recess 1050, opposed tab walls 1052 are formed extending transverse to the recess 1050 and having a gap 1054 therebetween.

The gap 1054 allows the retainers 1004 to be located in the plate 1002. Retainer 1030 includes a pair of arm portions 1060 and a bridge portion 1062. In an unconstrained and natural position, the arms 1060 angle outward from the bridge 1062. The retainer 1030 is located in the recess 1040 so that the bridge 1062 is positioned within an outboard portion 1064 of the recess 1040 and central portions 1060a of the arms 1060 extend across the bore 24. To insert the retainer 1030 in the plate 1002, terminal portions 1060b and the arms 1060 are elastically deflected inward and are passed through the gap 1054 between the tab walls 1052. Once through the gap 1054, the arms 1060 shift outward towards their natural position. Accordingly, the bridge 1062 may be positioned in the recess outboard portion 1064, and the arm terminal portions 1060b are positioned below the tab walls 1052.

With the retainers 1030 located in the plate 1002 in this position, the screw 22 may be driven through the retainers 1030 and secured with the plate 1002 and bone 12. As the screw 22 passes through the retainer 1030, the screw head 26 contacts the central portions 1060a, thereby forcing or camming the central portions 1060a away from each other to permit the head 26 to pass between the arms 1060. Once the head 26 is through, the arms 1060 shift back toward each so that at least a portion of the arms 1060 is positioned above the top surface 29 of the screw 22, thereby being positioned to restrict screw back-out.

The retainer 1032 operates is manner similar to that of retainer 1030. The retainer 1032 includes arms 1070, two bridges 1072 connected to respective arms 1070, and a connecting span 1074 between the bridges 1072. To insert the retainer 1032, the connecting span 1074 is inserted through the gap 1054 and the arms 1070 are elastically deflected or compressed inward to force the retainer 1032 into the bores 24. In this manner, at least a portion of each bridge 1072 is located in recesses 1040 of respective bores 24, and the arms 1070 are located underneath one tab wall 1052 while the span 1074 is located underneath the opposed tab wall 1052.

Screws 22 may be secured with the plate 1002 by driving them through the retainers 1032 located therein. The screw head 26 being advanced into the plate 1002 contacts one of the arms 1070 and a portion of the span 1074, elastically deflecting the arms 1070 and span portion 1074 outward to permit passing thereby. Once the head 26 has passed through, the arm 1070 and span portion 1074 return inwardly toward each so that at least a portion of the each is positioned above the top surface 29 of the screw 22, thereby being positioned to restrict screw back-out. Once retainers 1030 and 1032 are inserted into the plate during assembly, the tab walls 1052 are bent down to prevent the retainers 1030 and 1032 from escaping recess 1040.

Each of the bone plates is preferably made of biocompatible materials, such as titanium or titanium alloys, and stainless steels, or made of bioabsorbable materials, or made of a polymer, such as the polymer known as PEEK. In one embodiment, the plate is formed from anodized titanium.

As can be seen in FIGS. 4 and 53-55, the screw head 26 includes a drive recess 300. In the preferred embodiment, the drive recess 300 is a hexagonal recess for receiving a driver 900 (see FIGS. 41-43) with, for example, a standard hex driving end 902. With specific reference to FIGS. 54 and 55, a top portion 300a of the drive recess 300 is equipped with internal threads 302 with a large enough diameter that the driving end 902 may be inserted into the drive recess 300 with sufficient clearance of the internal threads 302 such that a sleeve 904 of the driver 900 may be threaded into the threads 302 with the driving end 902 located in the drive recess 300.

The sleeve 904 may be utilized when a surgeon desires to remove the bone screw 22. For instance, when installing the bone plate, the screws 22 may strip the threading made in the bone 12. Therefore, the screw 22 must be removed and a new one inserted. In order to extract the screw 22 from the stripped bone portion, the driving end 902 may be inserted into the drive recess 300 and rotated, but the lack of purchase will prevent the driver 900 alone from removing the screw 22. Therefore, the driving end 902 may be used to hold the screw 22 in a particular position, and the threaded sleeve 904 may be lowered and threaded into the top portion threads 302, wherein the sleeve 904 may be used to extract the screw 22. The sleeve 904 may also be used at any time that there may be a concern about the screw 22 becoming disconnected from the driver 900, such as insuring that the removed screw is not dropped into the surgical site.

Turning now to FIGS. 41-43, the driver 900 is depicted. The driver 900 includes a handle 910 connected to a driving shaft 912 that terminates in the driving end 902 that is received by the drive recess 300. Accordingly, turning of the handle 910 when the driving end 902 is seated within the drive recess 300 effects rotation of the screw 22. The driver 900 also includes the sleeve 904 including external threads 920 at its distal end 922 for threading into the internal threads of the top portion 300a of the drive recess 300 of the screw 22, as described above. The sleeve 904 is positioned closely about the driving shaft 912.

The sleeve 904 and driving shaft 912 may shift relative to each other along the longitudinal axis 901. That is, the sleeve 904 may be shifted relative to the driving shaft 912 in a distal direction such that the threads 920 of the sleeve 904 may be threaded into the drive recess 300. When the sleeve 904 is being threaded into or out of the drive recess 300, the driving end 902 will also be seated in the recess 300. In order to permit this, the sleeve 904 and driving shaft 912 need to rotate relative to each other so that the driving shaft 912 is held stationary relative to the screw 22. However, when the screw 22 is being inserted or extracted and the sleeve 904 is threaded into the recess 300, the sleeve 904 and driving shaft 912 do not rotate relative to each other. Accordingly, the sleeve 904 is held in position around the driving shaft 912 with a bushing, such as a pair of rings 930, 932. The rings 930, 932 provide a frictional fit so that the driving shaft 912 and sleeve 904 may be rotated together, and provide for an adjustable position longitudinally and rotationally, as manual force can overcome the friction between the driving shaft 912, sleeve 904, and rings 930, 932. The sleeve 904 may further include a grip 918 for manually holding or operating the sleeve 904.

A screw 22 to be implanted first receives the driving end 902 in the recess 300. Next, the sleeve 904 is advanced to the recess 300, and then screwed into the threaded portion 300a. In this manner, the screw 22 is secured to the driver 900. The screw 22 is then driven into the bone by clockwise rotation. To remove the driver 900, the sleeve 904 is rotated counterclockwise while the driving shaft 912 is held stationary. Once the sleeve 904 is freed from the recess 300, the driving shaft end 902 is removed from the recess 300. To remove the screw 22, the steps are simply reversed.

As is shown, the region 924 proximate to the distal end 922 of sleeve 904 is tapered. As such, the region 924 is not substantially larger than the threads 920 of the sleeve 904. However, the driver 900 may further be used to shift the retainer to an open position such that the screw 22 may be extracted. Therefore, the region 924 may alternatively be sized to the diameter of the screw head 26 such the driver 900 may be used to shift the retainer to the open position for extracting the screw 22. As a further alternative, a separate tool, such as in the form of an extractor 1900 (FIGS. 74, 75), may be used to shift the retainer to an open position.

Figure 75:
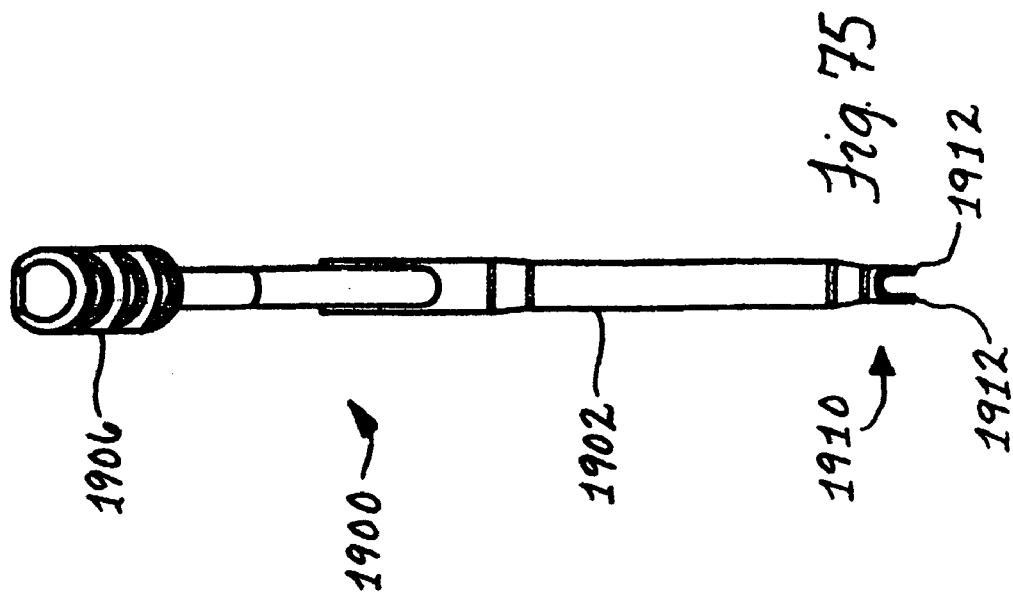
FIG. 75 is a rear elevational view of the extractor showing retainer-shifting tines.
Figure 74:
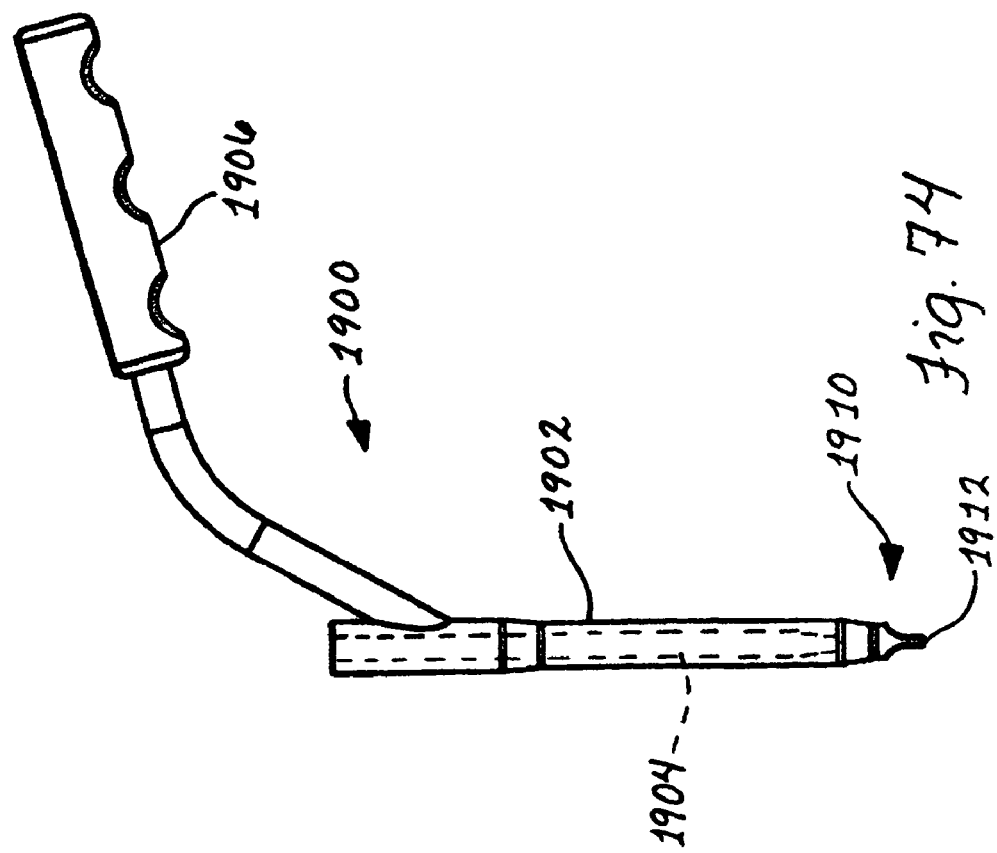
FIG. 74 is a side elevational view of an extractor tool for assisting in removal of bone anchors from an implanted bone plate.

The extractor 1900 may be used in conjunction with the driver 900 for removing screws. As shown in FIGS. 74 and 75, the extractor 1900 includes a sleeve member 1902 with an elongated cavity 1904 therein, and a handle 1906 angled away from the sleeve member 1902 so that a surgeon may utilize the extractor 1900 without the handle 1906 obstructing the view. At a distal end 1910 of the extractor 1900, a pair of prongs 1912 extends from the sleeve member 1902. To remove the screws, the prongs 1912 may be placed within a retainer and then rotated so that each prong 1912 contacts a portion of the retainer to force the retainer to an open position.

While holding the retainer open with the extractor 1900, the driver 900 may be inserted through the extractor cavity 1904. The driving end 902 of the driver is received in the screw, and the external threads 902 of the driver sleeve 904 may be threaded into the screw head 26 so that the screw 22 may be easily and safely removed. The driver 900 is then rotated or pulled to withdraw the screw 22 from the bone, and is finally removed.

Figure 53:
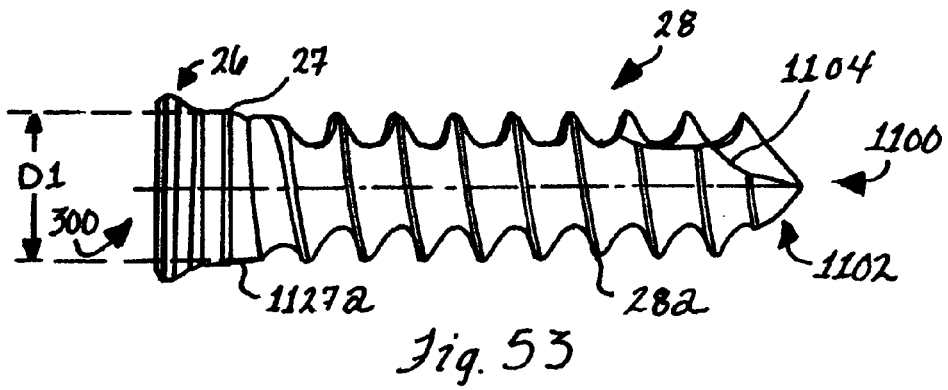
FIG. 53 is a side elevation view of a bone plate fastener in the form of a self-drilling bone screw.
Figure 54:
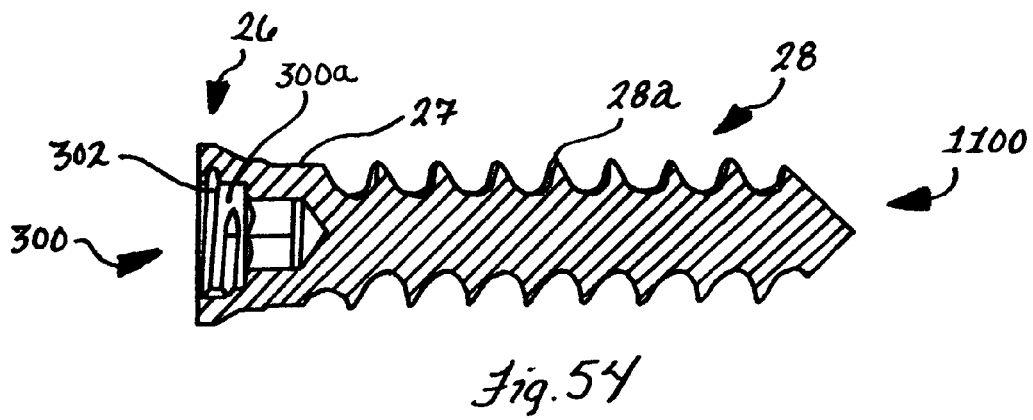
FIG. 54 is a cross-sectional view of the bone screw of FIG. 53.
Figure 55:
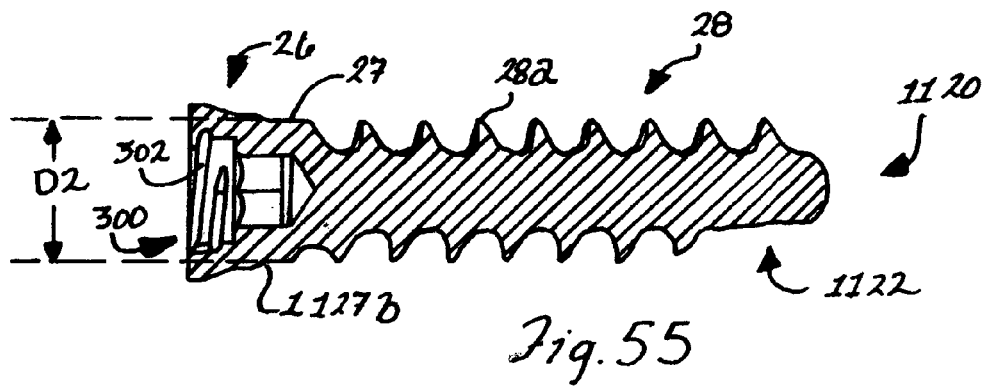
FIG. 55 is a cross-sectional view of a bone plate fastener in the form of a self-tapping bone screw.
Figure 56:
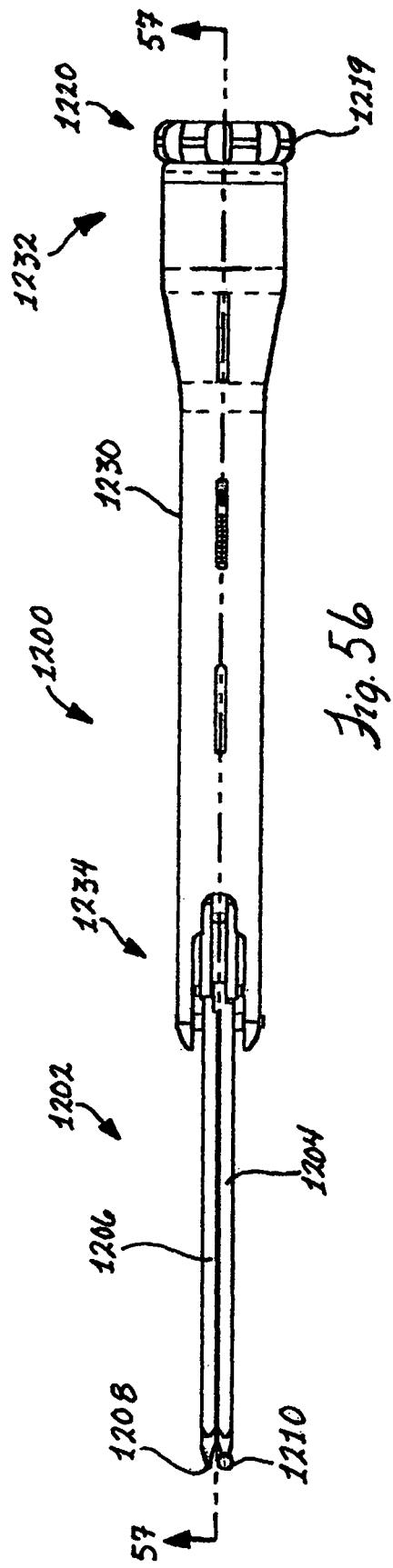
FIG. 56 is a side elevational view of a sizing tool for measuring portions of a spine.
Figure 57:
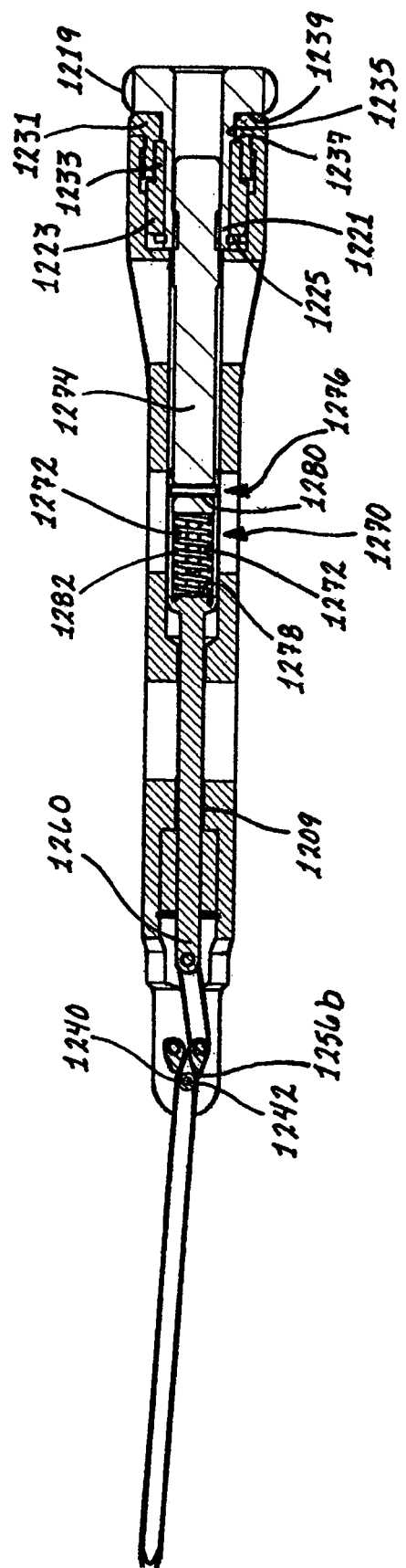
FIG. 57 is a cross-sectional view of the sizing tool taken through the line 57-57 of FIG. 56.
Figure 58:
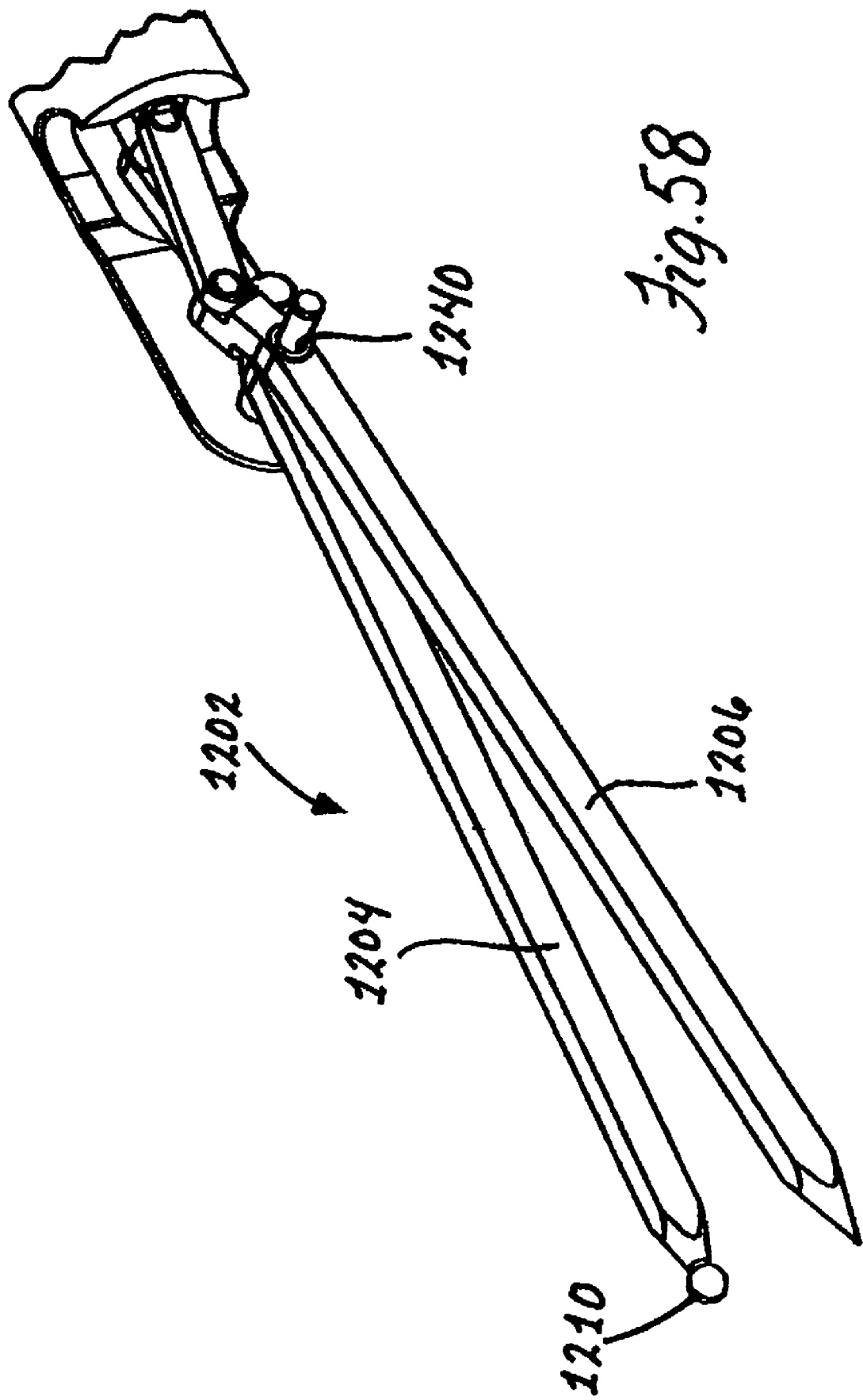
FIG. 58 is a fragmentary view of a distal end of the sizing tool.
Figure 59:
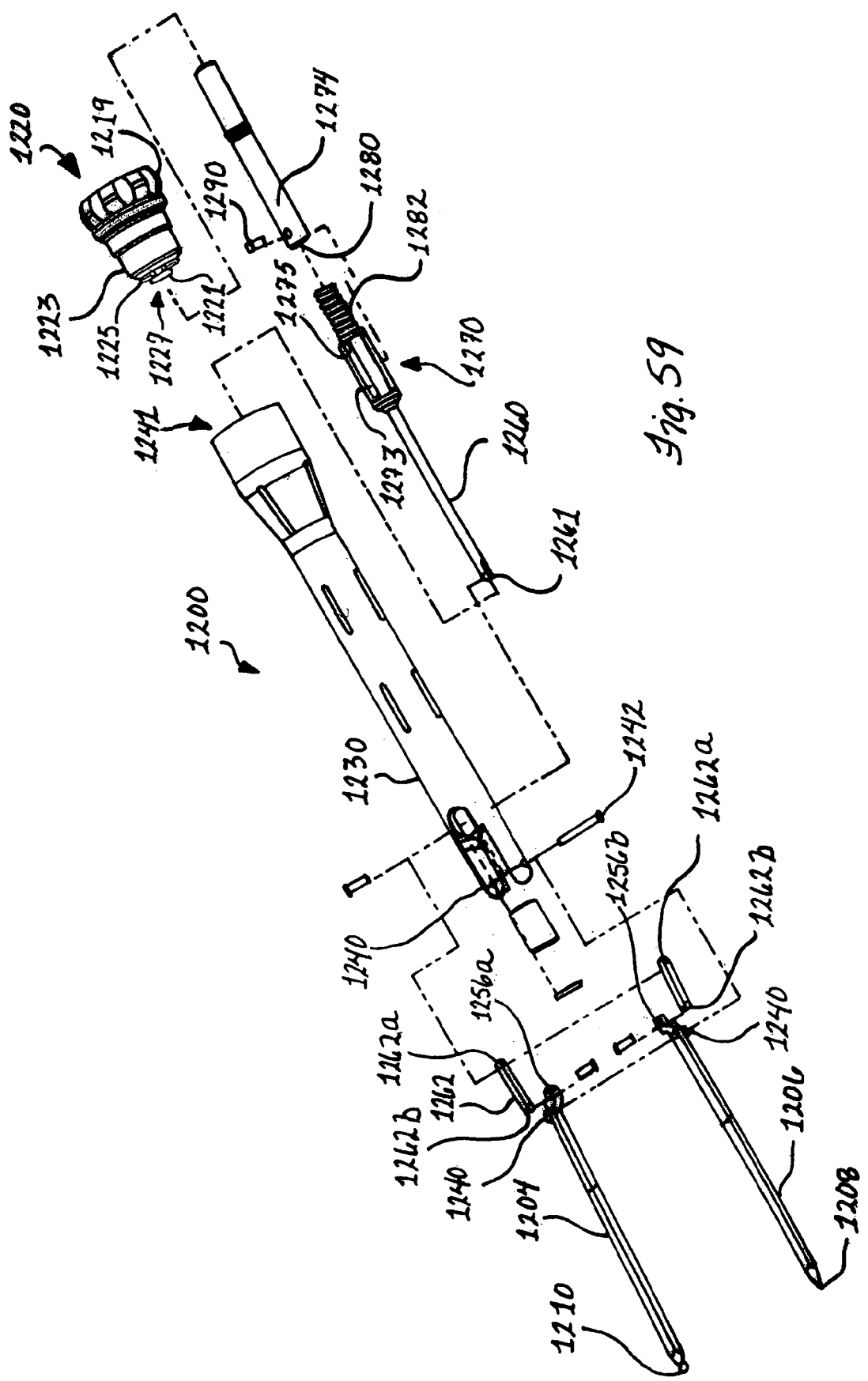
FIG. 59 is an exploded view of the sizing tool.
Figure 60:
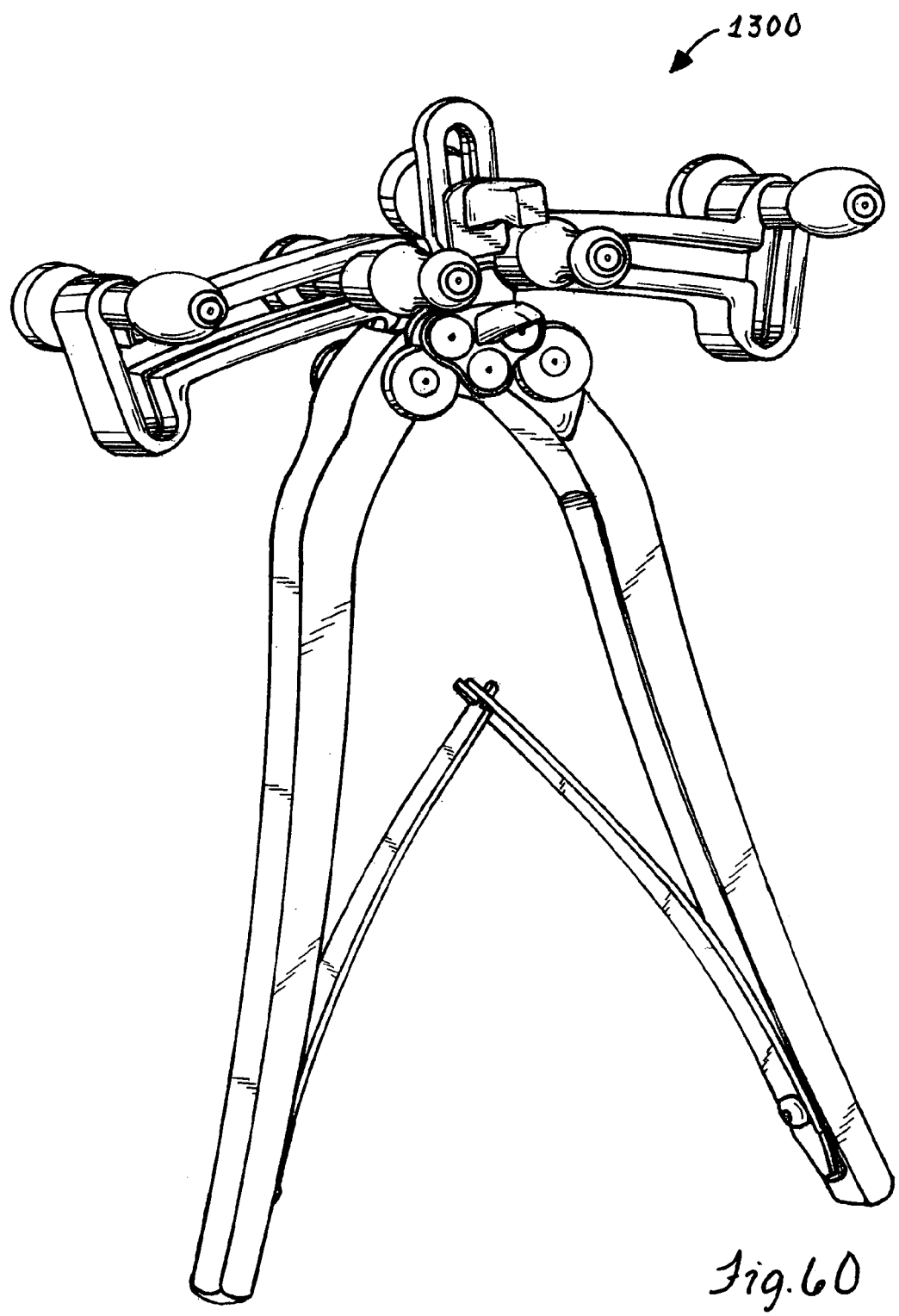
FIG. 60 is a perspective view of a bending tool for adjusting the shape of a bone plate in accordance with the present invention.
Figure 61:
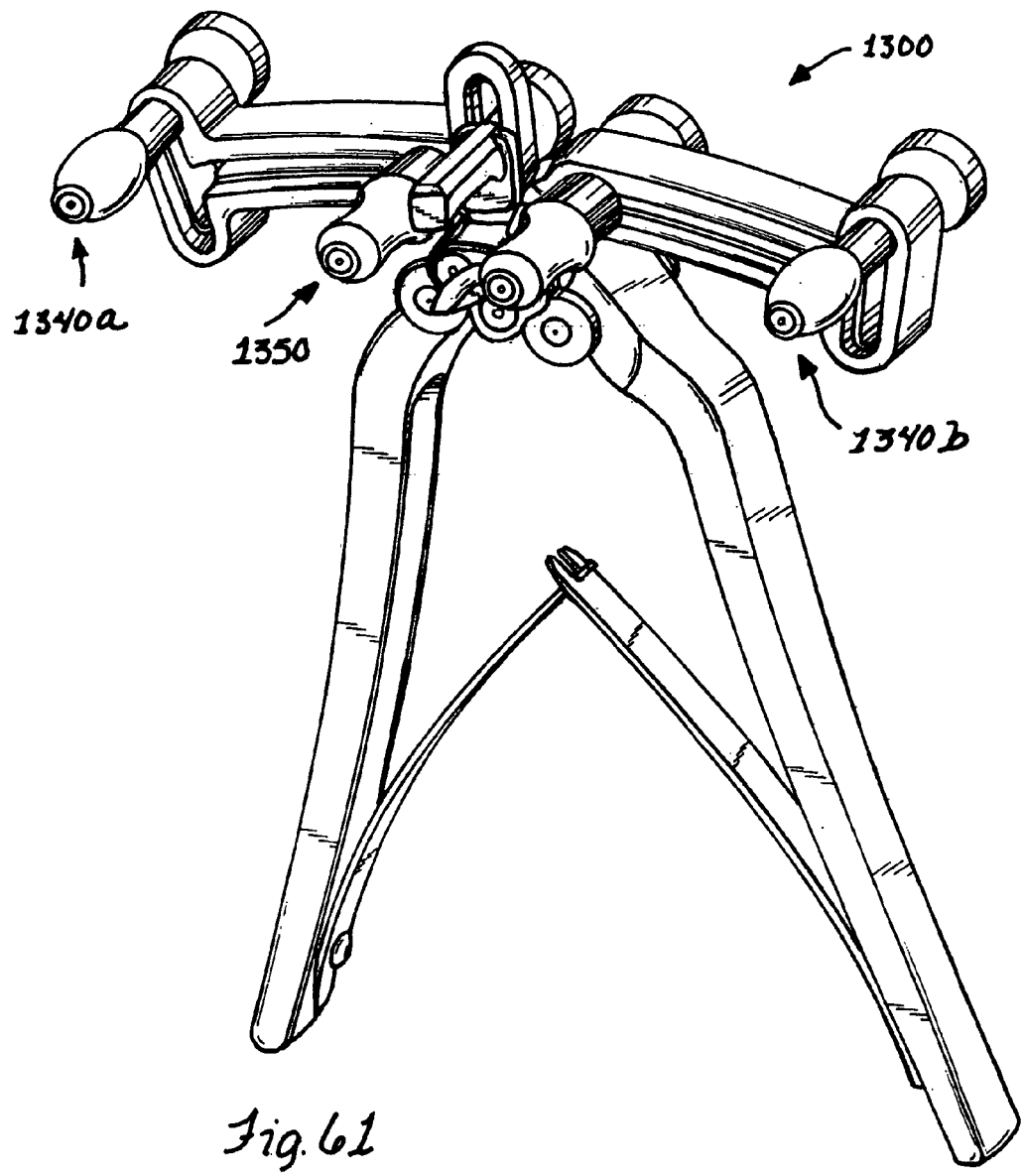
FIG. 61 is a second perspective view of the bending tool.
Figure 62:
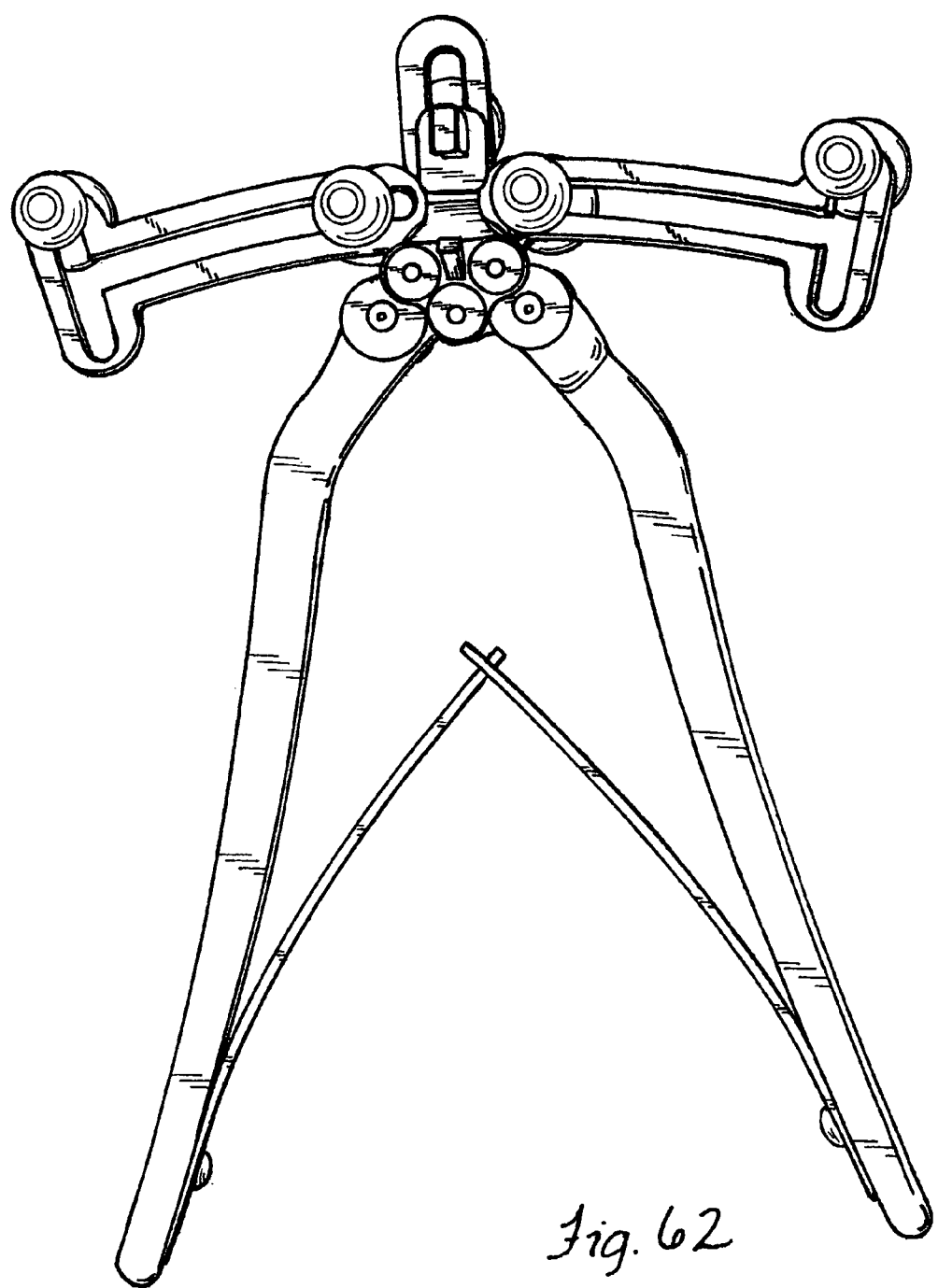
FIG. 62 is a front plan view of the bending tool.

A self-drilling screw 1100 is depicted in FIGS. 53 and 54, and a self-tapping screw 1120 is depicted in FIG. 55. Each screw 1100, 1120 has a shank 28 including threads 28a, a head 26, and a neck 27 therebetween. As can be seen, the self-drilling screw 1100 includes a tip 1102 that is pointed and a cutting flute 1104 formed in the threads 28a. Thus, the self-drilling screw 1100 may be placed against a bone 12, or in a pilot hole of a bone 12, and advanced by forcibly driving the screw 1100 into the bone 12. The cutting flute 1104 forms a hole in the bone 12 as the screw 22 is advanced, and the threads 28a cut into the bone 12 to form cooperating threads in the bone 12. Preferably, the self-drilling screws 1100 are provided in a length short enough to prevent accidental driving of these sharper screw tips into sensitive tissues, such as nerves or blood circulatory passages.

The self-tapping screw 1120 is provided with a tip 1122 that is rounded and substantially dull. The screw 1120 may be advanced into a pilot hole formed in the bone 12, and the threads 28a form cooperating threads in the bone 12 as the screw 1120 is forcibly driven into the bone 12.

As noted above, the bone screws 22 are preferably polyaxial for being driven into the bones 12 at an angle desired by the surgeon or dictated by the surgical site, or may be formed to provide a specific angle with the plate, these being referred to as fixed. As represented, the self-drilling screw 1100 is polyaxial, and the self-tapping screw 1120 is a fixed screw. More specifically, screw 1100 has a neck 1127a with a diameter D1, and screw 1120 has a neck 1127b with a diameter D2. The bone plates are provided with a brace surface surrounding a lower portion of the bore, and the bore lower portion has a specific diametral size or, for a dynamized bore, a transverse size or distance across the bore lower portion. These sizes may be uniform for an individual plate, or different bores may be provided with different sizes.

The screw necks 1127a, 1127b are, when secured in the plate, positioned within the bore lower portion 1012. For the polyaxial screw 1100, the diametral size of the bore 1012 is larger than the screw neck diameter D1. For the fixed screw 1120, the diametral size of the bore 1012 is sized large enough only to permit the screw neck 1127b with the diameter D2 to be inserted therein and fit against the brace surface 1016, in a peg and hole fashion. Thus, the fixed screw 1120 is provided with an angle of insertion.

It should also be noted that, in the event the bone is stripped, rescue screws (not shown) may be provided for securing in the bone. A rescue screw is a screw that has a larger thread diameter, or a larger central or minor diameter, or both. The rescue screw is able to gain purchase in the stripped hole, treating the it as if it were merely a pilot hole, by virtue of its larger size.

As discussed, a surgeon may select from an array of bone plate systems. The number of bores and tiers in the plate may be chosen based on the number of vertebrae to be spanned. The bores may be selected to be dynamized or non-dynamized depending on the amount of post-implantation compression desired. The screws may be fixed or polyaxial depending on the ability or desire for having a variable or fixed orientation or angle for the screw to be driven. For each of these choices, the surgeon may also select the actual size or dimensions of the plate, bores, and screws, typically determined by examining the vertebral portions to which the plate is to be secured.

To determine the plate size for a particular patient, a plate sizer or sizing caliper 1200 is utilized, as is shown in FIGS. 56-59. In the present embodiment, the sizing caliper 1200 includes a pair 1202 of legs adjustably positioned to align with points on one or more vertebrae to determine the proper distance for the screws 22 or the proper length of the plate required for the patient's anatomy.

The pair 1202 is composed of a measuring leg 1204 and a reference leg 1206 that has a sharp tip 1208 for being placed on a first desired location point on a vertebra. The location point may be a location for a bone screw 22 to be inserted thereat, or it could be a location defining the extent of one end of the bone plate itself. A pilot hole may be made in the vertebra, and the sharp tip 1208 may be placed in the pilot hole so that the position of the reference leg 1206 is more easily retained in place on the vertebra.

The sizing caliper 1200 is then adjusted by rotating a knob 1220. This rotation causes the measuring leg 1204 to move towards or away from the reference leg 1206 positioned at the first desired location point. The measuring leg 1204 includes a ball-shaped tip 1210 so that it may move across the surface of the vertebra, for instance, with minimal catching on the surface or other tissue attached thereto. The position of the measuring leg 1204 is adjusted until the ball tip 1210 is located at a second location point, which also may be a location for insertion of a bone screw 22 or a location defining the extent of a bone plate end. The measurement taken by the legs 1204, 1206 may then be compared directly to a plate, or may be compared to a scale.

The sizing caliper 1200 includes an elongate body 1230 with the knob 1220 located at a proximal end 1232 and the legs 1204, 1206 generally secured at a distal end 1234. The legs 1204, 1206 are secured together at a pivot point 1240 through which a pin 1242 is inserted to retain the legs 1204, 1206 on the body 1230. When the knob 1220 is rotated, the legs 1204, 1206 shift position, either inward or outward depending on the direction of knob rotation, by pivoting around the pivot point 1240.

Both legs 1204, 1206 include a pivot arm 1256 that is outwardly angled in the proximal direction from the rest of the leg 1204, 1206 such that force on a terminal end of the pivot arm 1256 causes the legs to rotate around the pivot point 1240. The respective pivot arms 1256*a*, 1256*b* of the legs 1204, 1206 are angled away from each other and, when force is applied to both pivot arms 1256*a*, 1256*b*, the legs 1204, 1206 pivot in opposite directions. The legs 1204, 1206, thus, operate in a scissors-like fashion.

To effect such movement with the knob 1220, the pivot arms 1256 are pivotally connected to a central reciprocating member 1260. Movement of the reciprocating member 1260 in one direction causes the legs 1204, 1206 to move towards each other, while movement in the other direction causes the legs 1204, 1206 to move apart. The path of the reciprocating member 1260 is defined by a channel 1209 in the body 1230 so that the path is generally linear.

The reciprocating member 1260 has a connection end 1261 pivotally attached to a proximal ends 1262*a* of links 1262, which are then pivotally attached at distal ends 1262*b* to the outwardly angled pivot arms 1256. Being attached to the connection end 1261 and to the outwardly angled pivot arms, the links 1262 are inwardly angled in the proximal direction. As the connection end 1261 moves towards the pivot point 1240 common to both legs 1204, 1206 and the distance therebetween is decreased, the links 1262 attached to the connection end 1261 are further spread outward relative to each other. Conversely, when the connection end 1261 is retracted along with the reciprocating member 1260, the links 1262 are drawn together to draw the legs 1204, 1206 together.

The reciprocating member 1260 includes a proximal, drive end 1270 having a recess or cavity 1272 for receiving therein a drive end 1276 of a drive member 1274. The cavity 1272 includes a distal wall 1278 generally facing an end surface 1280 of the drive end 1276. A bias or compression member 1282 is located within the cavity 1272 in between the distal wall 1278 and the end surface 1280. When the drive end 1270 is directed in a distal direction, the end surface 1280 of the drive end 1270 applies force to the compression member 1282, which is translated to the distal wall 1278 and, hence, to the reciprocating member 1260. In this manner, advancement of the drive member 1274 forces the reciprocating member to advance, which in turn spreads the legs 1204, 1206 towards an open position.

To retract the legs 1204, 1206, the drive member 1274 is withdrawn, thereby retracting the reciprocating member 1260. The reciprocating member cavity 1272 is provided with a transversely oriented opening 1273 or rail for guiding the motion of the drive member 1274. The drive member 1274 is secured within the cavity 1272 by inserting a pin 1290 through the opening 1273 and through the drive member 1274. When the drive member 1274 is retracted, the pin 1290 interferes with a rear wall 1275 in the opening 1273 so that the reciprocating member 1260 is also retracted.

The minimally invasive sizing caliper 1200 may be utilized over a span of vertebrae for which the surrounding tissue is not completely removed or resected. The minimally invasive sizing caliper 1200, as well as other instruments, preferably may access the implant site without requiring an opening in the patient as large as the implant site. The sizing caliper 1200 may be directed into the patient opening, and the legs 1204, 1206 may then be opened.

When the legs 1204, 1206 are opened, they are often larger than the patient opening. So that the sizing caliper 1200 may be removed prior to comparing the caliper to, for instance, the distance between bores on a plate, the legs 1204, 1206 may pivot to a smaller position as the caliper 1200 is being withdrawn. Once clear of the patient opening, the legs 1204, 1206 return to the position they were in prior to removal and positioned at the vertebrae measuring points. This is achieved by use of the compression member 1282. After the instrument is removed from the patient, it may be compared directly to the plates of different sizes or may be compared to a scale to determine the required plate size.

When the caliper 1200 is withdrawn, the patient's flesh may force the legs 1204, 1206 together, or a surgeon may alternatively force them closed to ease removal of the caliper 1200. As can be seen, in order to force the legs 1204, 1206 together, the reciprocating member 1260 must retract towards the proximal end of the caliper 1200. The compression member 1282 in the form of a spring permits such retraction.

As the legs 1204, 1206 are forced together, the reciprocating member 1260 compresses the spring 1282 against the drive member 1274. The drive member 1274 remains stationary so that, once the caliper 1200 is removed and the force applied to the legs 1204, 1206 is relieved, the legs 1204, 1206 return to the position in which they were when measuring the implant site. An accurate measurement may then be taken from the legs 1204, 1206.

To advance or retract the drive member 1274, the knob 1220 is rotated in one direction or the other, as previously noted. The knob 1220 does not change position relative to the body 1230, other than by rotating. The knob 1220 includes an enlarged grip portion 1219, and a shaft portion 1221 extending therefrom in the distal direction and received within the body 1230. More specifically, the shaft portion 1221 is received by a bushing 1223, and a snap ring or C-ring 1225 is secured to a distal end 1227 of the shaft portion 1221 to retain the shaft portion 1221 within the bushing 1223. The grip portion 1219 may be manually operated to rotate the knob 1220 relative to and within the bushing 1223.

A nut 1231 with a threaded exterior portion 1233 and an internal bushing surface 1235 is located between a shoulder 1237 on the bushing 1223 and a shoulder 1239 on the grip portion 1219. The threaded portion 1233 is threaded into a threaded opening 1241 in the proximal end of the body. Accordingly, the nut 1231 is retained with a generally stationary position within the body 1230. Furthermore, the nut 1231 between the shoulders 1237, 1239 retains the knob 1220 in a position permitting rotation only.

The drive member 1274 is prevented from rotation by the pin 1290 received by the opening 1273 in the reciprocating member 1260. The shaft portion 1221 of the knob 1220 includes an inner threaded cylindrical bore 1251 into which the drive member 1274 is threadably received. As the knob 1220 rotates relative to the body and reciprocating member, the drive member 1274 is unable to similarly rotate. Accordingly, the knob 1220 also rotates relative to the drive member 1274. Because the drive member 1274 is threadably engaged with the knob 1220, the threads therebetween cause the drive member 1274 to advance or retract relative to the knob 1220, depending on the direction of rotation. Accordingly, the reciprocating member 1260 is advanced or retracted, and the legs 1204, 1206 are opened or closed.

Implantation of a bone plate is a relatively invasive procedure, and the bone plate residing in a living tissue environment contacts and interacts with that tissue. In fact, patients who have received bone plates on the anterior side of the cervical portion of the spine have been known to physically feel the presence of the plate, particularly when swallowing. Accordingly, it is desirable to minimize the degree to which the bone plate interferes with the surrounding tissues. Moreover, the structural performance of the bone plate benefits from conforming its shape to the natural curves of the spinal column. However, for each individual implant site, the lordotic curve of the spinal column and the lateral curve of each vertebrae is unique, though certainly within typical, somewhat predictable ranges.

As discussed herein, the cervical plate may be provided with a curvature in the longitudinal direction that is provided for the plate in order to conform the plate to the average natural lordotic curvature of the spine, as well as to reduce interference with surrounding tissues. It is often desirable to alter the standard shape of the plate to fit an individual patient's unique anatomy. This should be done in a manner so as not to scratch or mar the surfaces of the bone plate, which otherwise may negatively affect the long term fatigue performance of the bone plate. For this purpose, a plate bending instrument 1300 is provided for altering the curvature of the plate when necessary due to a unique anatomy, a preferred form of which is illustrated in FIGS. 60-66.

The plate bender 1300 is operated to either increase or decrease the radius of the lordotic curvature of the plate. In operation, the plate bender 1300 is selectively operable so that a pair of opposed actuator handles 1331,1332 for bending the plate operate to impart a bending motion in a selected direction by directing the handles 1331, 1332 towards each other. The plate bender 1300 includes a pair of opposed arms 1310, 1320 extending laterally from the handles 1331, 1332, and each of the handles 1331, 1332 and arms 1310, 1320 are operatively connected and pivotally secured at a pivot point 1375a by a pin 1375. As will be described herein, the plate bender 1300 includes engaging pegs or keys 1372, 1382 that are selectively shiftable so that the each of the handles 1331, 1332 are operatively engageable with either of the arms 1310, 1320.

Figure 63:
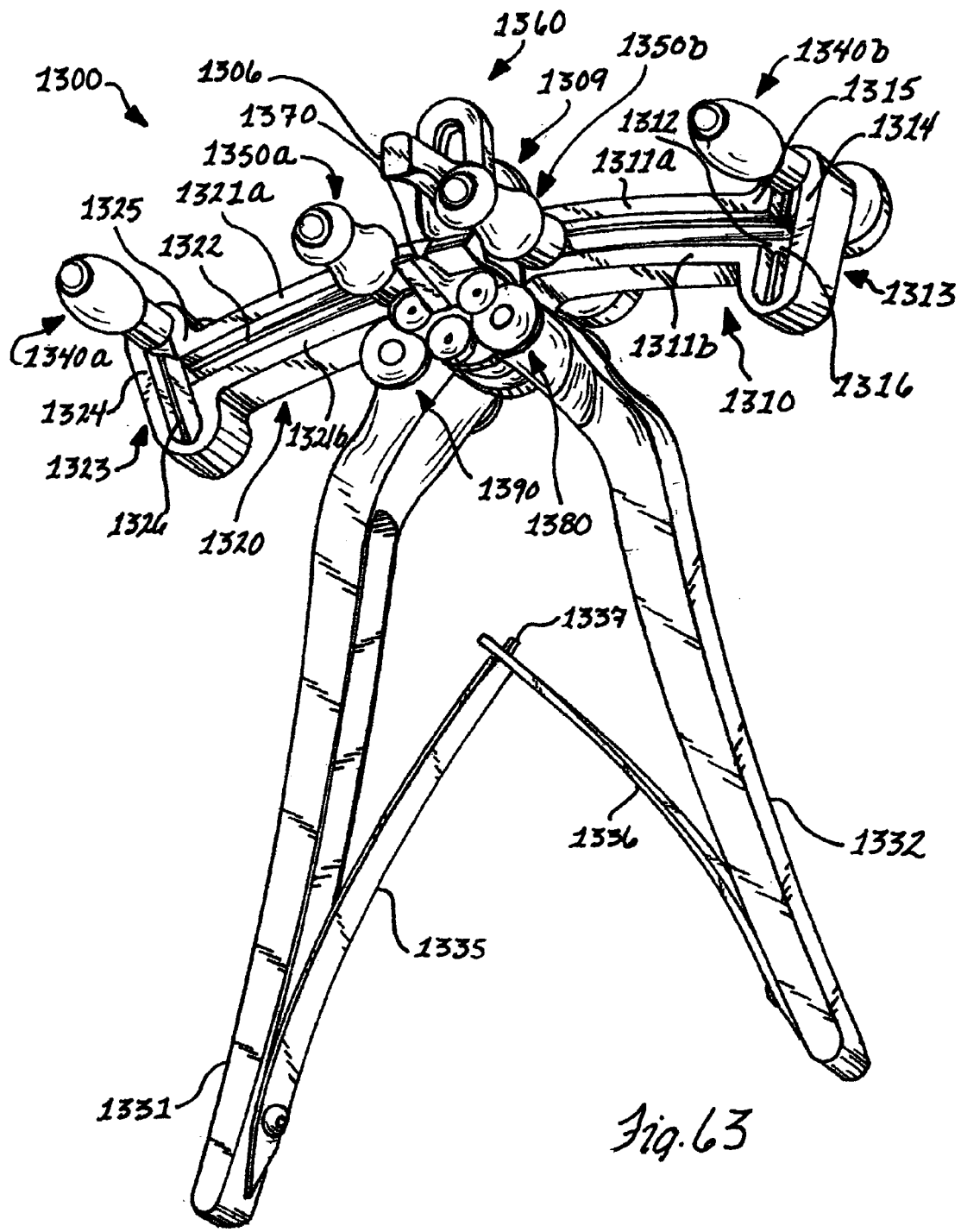
FIG. 63 is a perspective view generally of a front side of the bending tool taken from above thereof.
Figure 64:
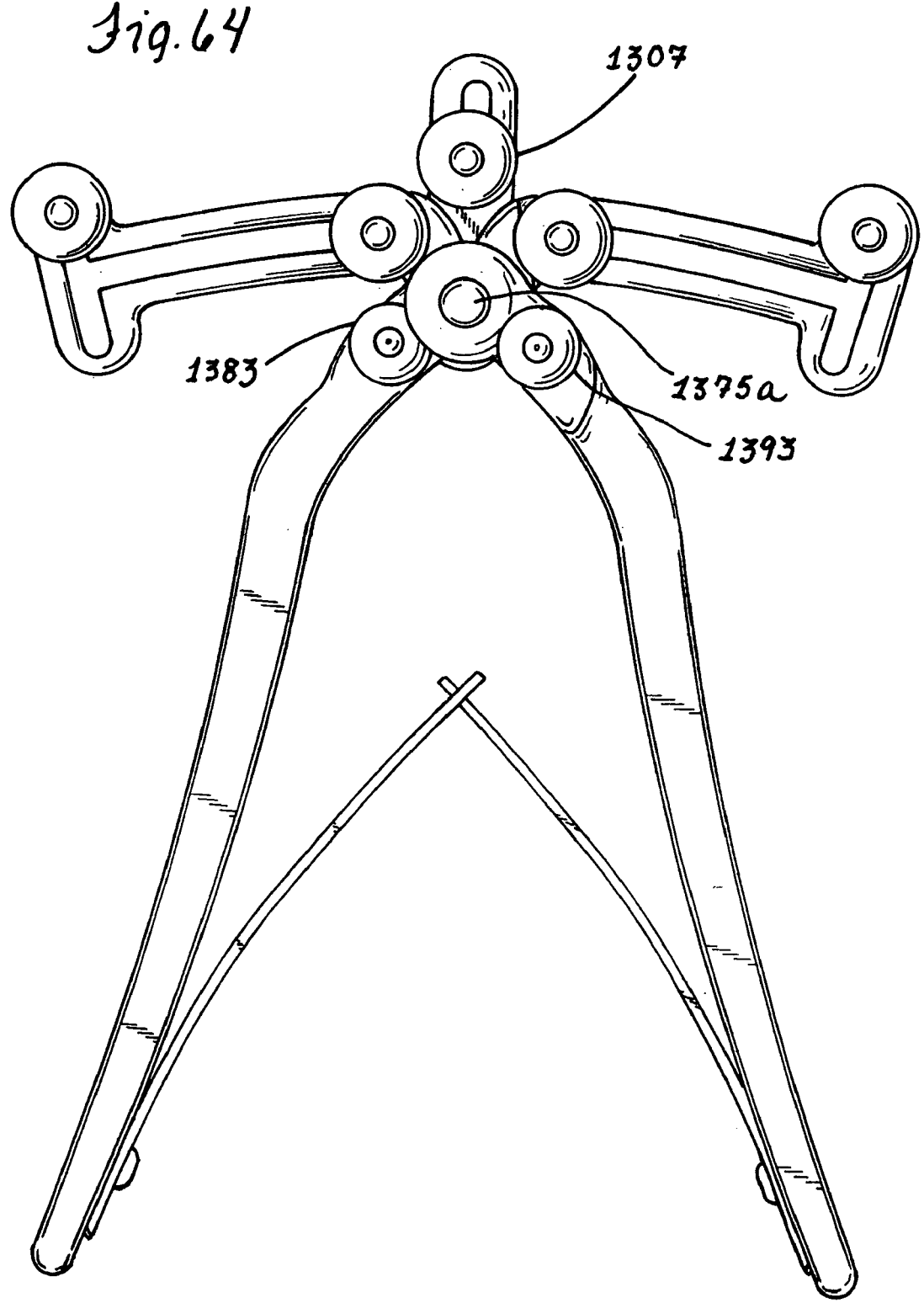
FIG. 64 is a perspective view generally of the front side of the bending tool taken from below thereof.

With reference to FIG. 63, the opposed actuator handles 1331 and 1332 are pivotally joined at an upper portion. The opposed lower gripping portions of the handles 1331 and 1332 are biased outward from each other by a bias member in the form of attached springs 1335 and 1336, which connect by insertion of tab 1337 into the mating slot 1338 of the spring 1336. The springs 1335 and 1336 are connected to the inward facing sides of handles 1331 and 1332 by rivets or by any other suitable means of attachment.

Each handle 1331, 1332 respectively includes an upper shoulder portion including an extending flange 1333, 1334, and a central aperture 1333a, 1334a. The flanges 1333 and 1334 are connected to the cylindrical pin 1375 which extends through the apertures 1333a and 1334a to provide a central pivot 1375a for the handles 1331 and 1332, and squeezing the handles 1331, 1332 against the bias provided by springs 1335, 1336 causes the flanges 1333, 1334 and handles 1331, 1332 to pivot about the pivot 1375a.

Figure 66A:
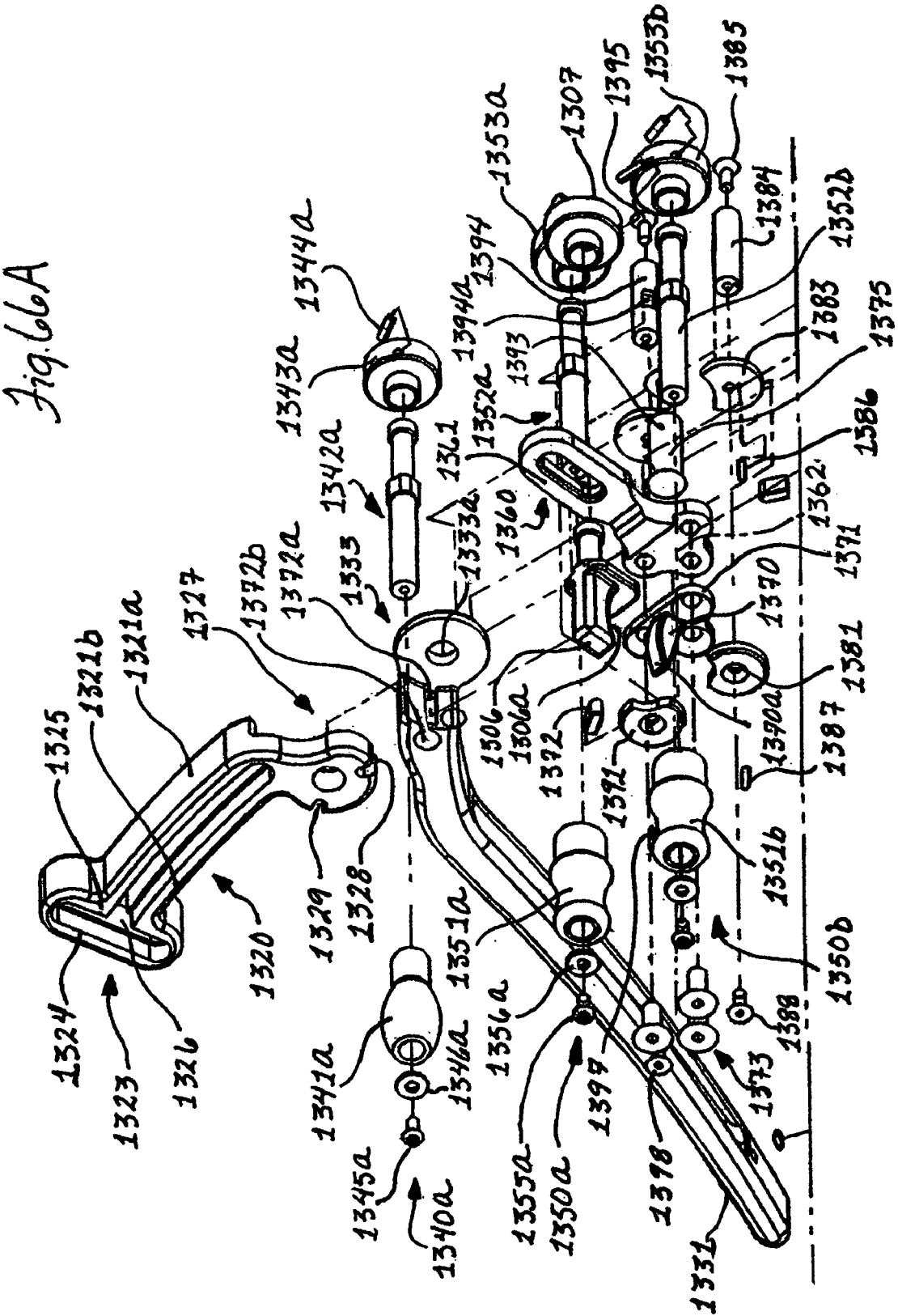
FIGS. 66A and 66B are partial exploded views of the bending tool.
Figure 66B:
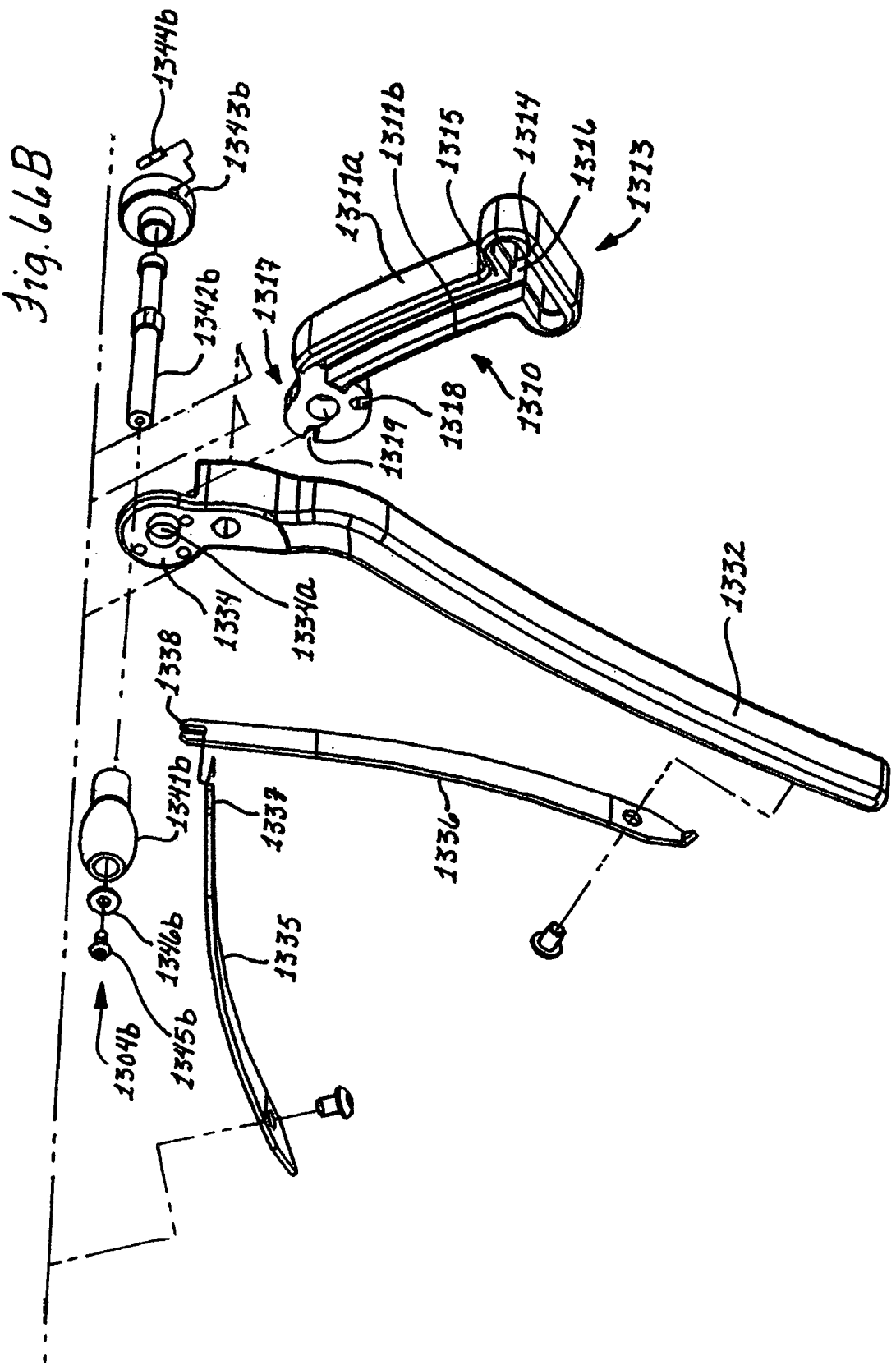
Figure 67:
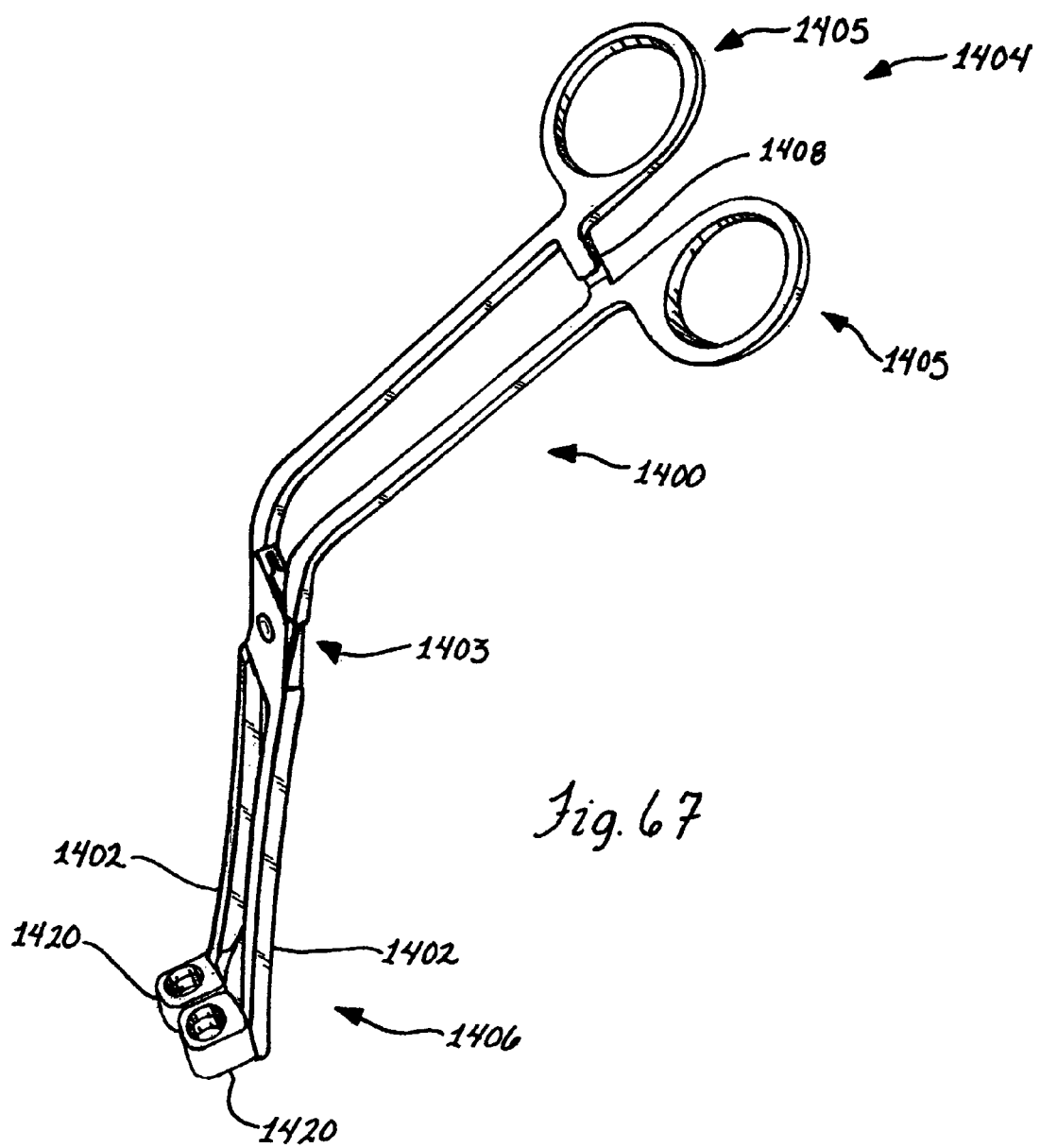
FIG. 67 is a perspective view of a holding tool for positioning the plate during implantation.
Figure 68:
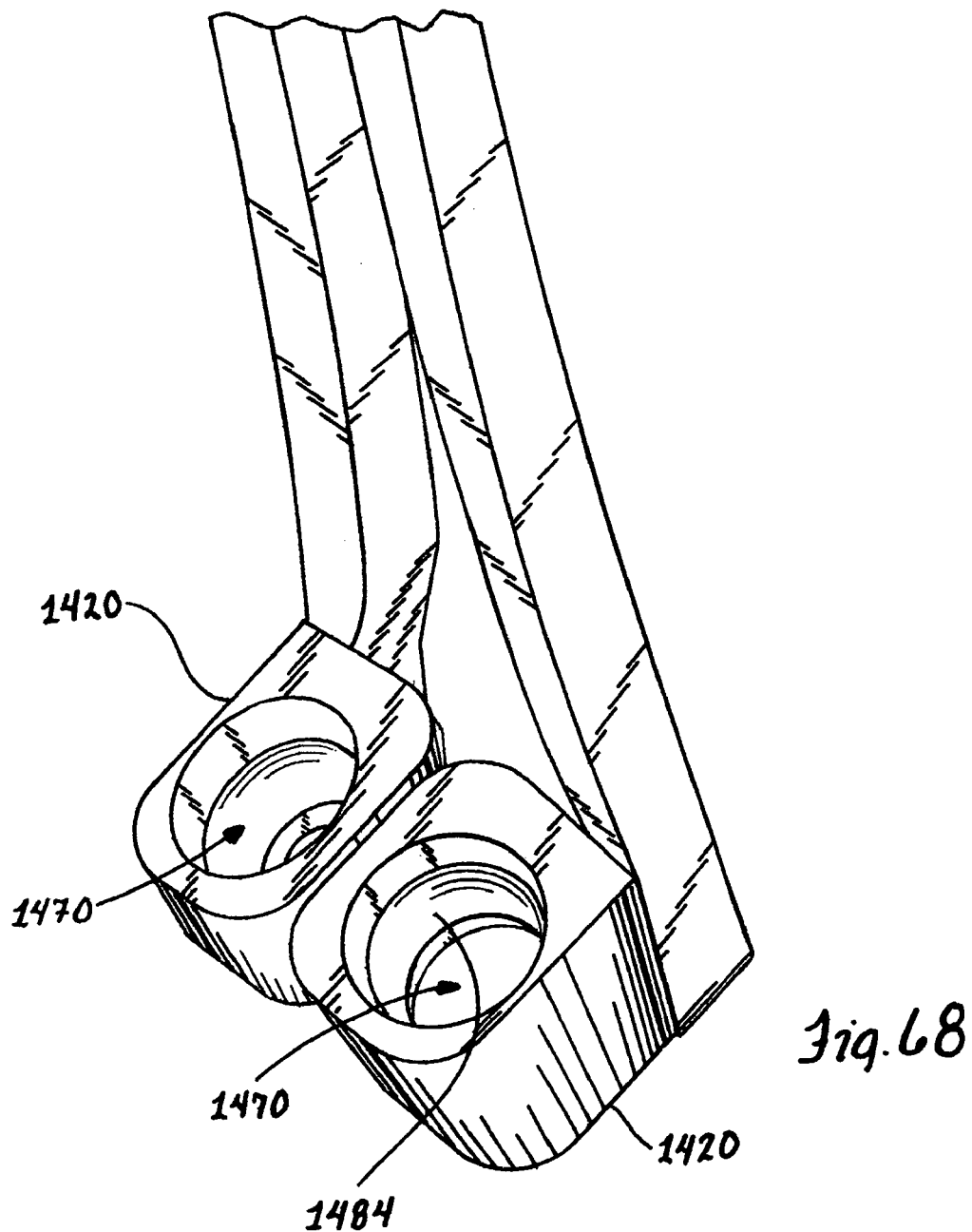
FIG. 68 is a fragmentary view of a side of a distal end of the holding tool showing recess for a drill guide for implanting a bone plate.
Figure 69:
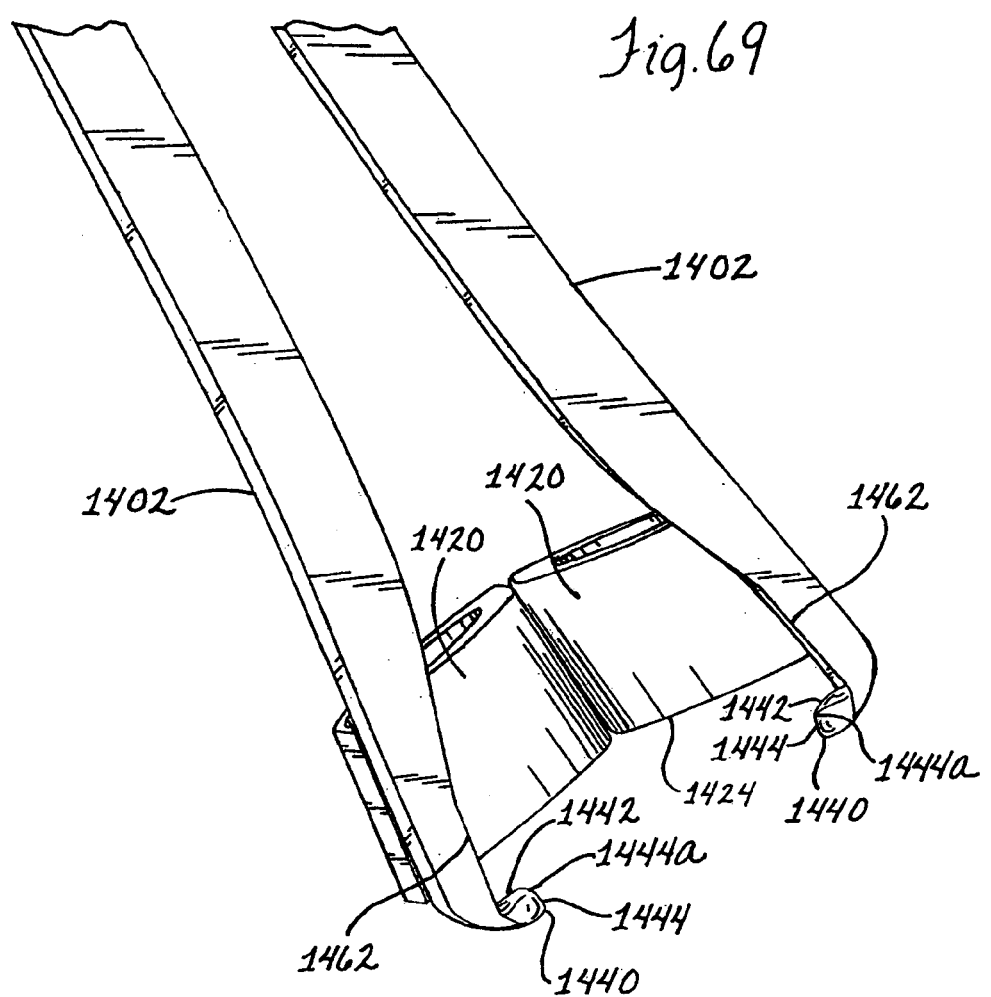
FIG. 69 is a second fragmentary view of a back side of the distal end of the holding tool.
Figure 70:
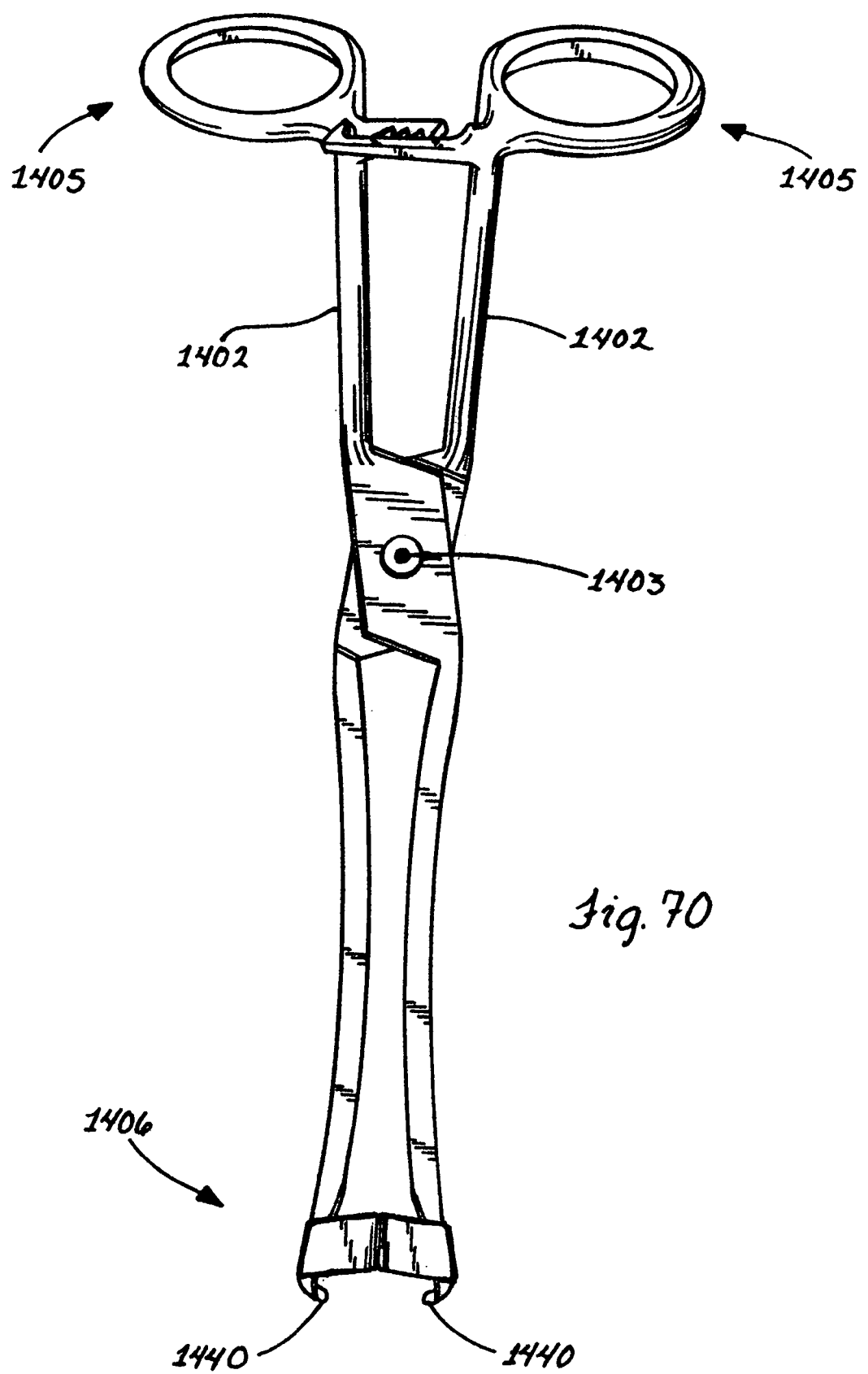
FIG. 70 is a front elevational view of the holding tool.

With reference to FIG. 63 and with particular reference to FIGS. 63 and 66, the first arm 1320 includes a portion extending generally laterally from the central pivot 1375a formed by opposed arm portions 1321a and 1321b, which define a central horizontally extending race 1322. The arm 1320 also includes an end portion 1323 which extends generally perpendicular to extending members 1321a and 1321b. Extending members 1321a and 1321b are preferably curved to match the standard anterior and posterior curvature of the cervical plate.

The arm end portion 1323 includes opposed side walls 1324 and 1325 defining a channel or a race 1326 oriented transverse to the race 1322. Similarly, the arm 1310 includes a laterally extending portion including extending members 1311a and 1311b which define a race 1312 extending in the opposite direction of the race 1322. The arm 1310 includes an end portion 1313 formed from opposed sidewalls 1315 and 1314 which define the race 1316 extending generally perpendicular to the race 1312.

Each arm 1310 and 1320 includes roller assemblies selectively positionable within races of the respective arms 1310, 1320. Each arm 1310,1320 is provided with a convex roller assembly 1340 and a concave roller assembly 1350. Each roller assembly includes a roller having a central longitudinal aperture and a pin mounted through the aperture on one side and to a knob connected to the pin on the backside of the instrument.

Representatively, with reference to FIG. 66, convex roller assembly 1340a is comprised of convex roller 1341a which is positioned about its central aperture on the pin 1342a and connected to the pin by a screw 1345a through a washer 1346a. A knob 1343a is attached to the opposite end of the pin 1342a by means of a connecting pin 1344a, which extends through the knob 1343a in a direction traverse to the longitudinal direction of the pin 1342a and is retained by a shoulder at the end of the pin 1342a. Loosening the knob 1343a permits the convex roller assembly 1340a to be positioned at any desired location within the race 1326 or the race 1322. Tightening the knob 1343a secures the roller assembly 1340a at its desired position. As shown in FIG. 66, convex roller assemblies 1340a, 1340b and concave roller assemblies 1350a and 1350b are movably secured to the arms of the plate bending instrument 1300 in a corresponding manner.

The roller assemblies are used in conjunction with one of two fulcra to adjust the curvature of the plate. The plate bender instrument includes a lower fulcrum 1370 extending frontward in the general direction of the central pivot access 1375 and an upper fulcrum 1306 also extending in the same direction. The lower fulcrum 1370 has a convex bending surface 1370a directed upward, and the upper fulcrum 1306 has a concave bending surface 1306a directed downward. The fulcra 1306, 1370 are connected to tool mount 1360, and the upper fulcrum 1306 is selectively positionable upward and downward along a slot 1361 in the tool mount 1360 by a knob 1307 that may be loosened to allow the movement thereof and may be tightened to fix the selected position. The concave roller assemblies are used in combination with the lower fulcrum 1370 to increase the curvature of a plate, while the convex roller assemblies are used in with the upper fulcrum 1306.

Figure 65:
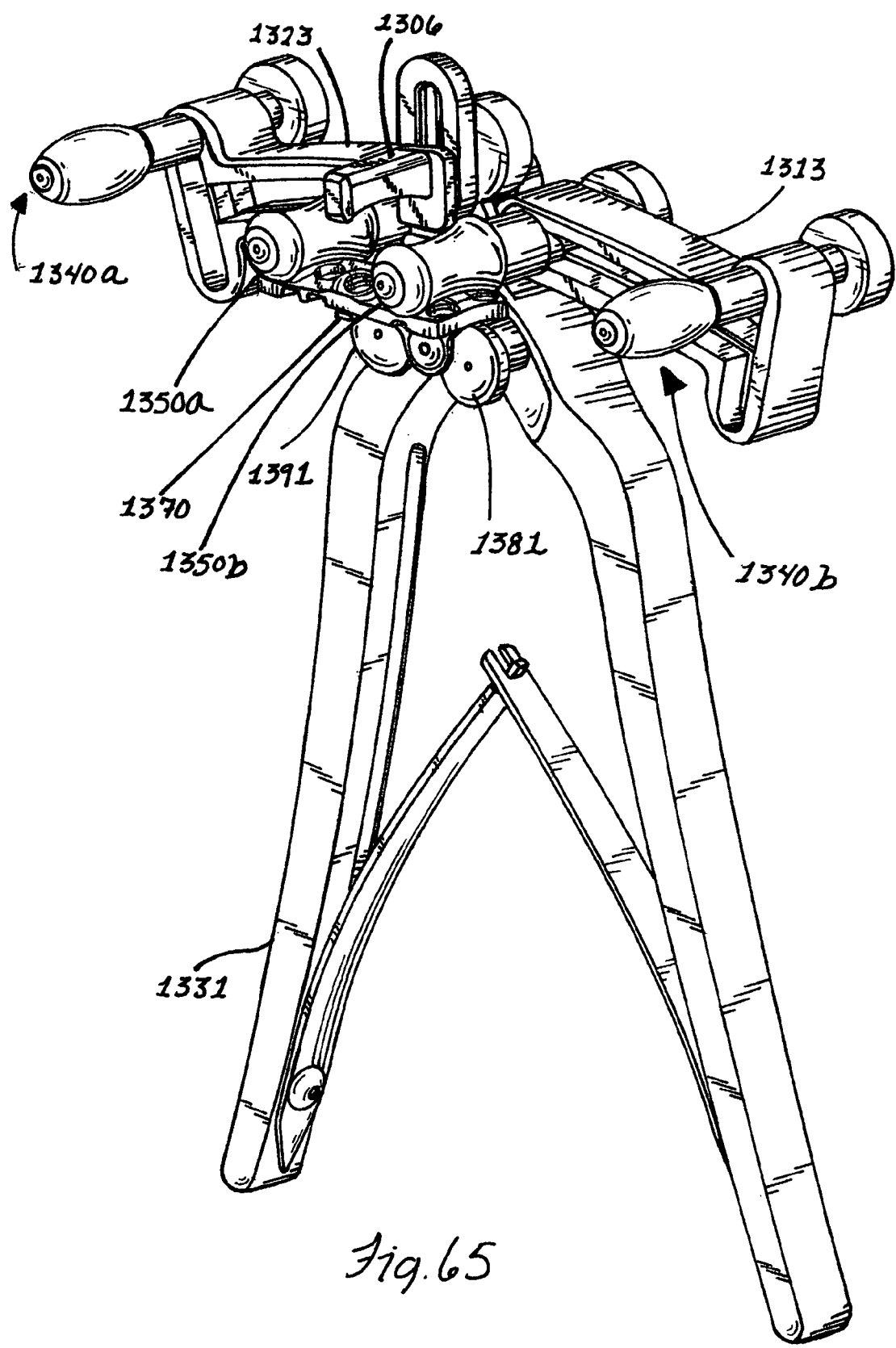

Representatively, by placing the plate above the fulcrum 1370 and positioning the concave roller assemblies 1350a and 1350b above the plate and spaced horizontally from the fulcrum 1370, the concave rollers may apply a downward force to bend the plate about the fulcrum 1370, as shown in FIG. 65, thereby increasing the curvature of the plate when the tool 1300 is operated. When used for this purpose, the convex roller assemblies 1340*a* and 1340*b* may be moved to the positions shown in FIG. 63 so as to not interfere with the bending operation. On the other hand, a plate placed between the convex rollers 1340*a*, 1340*b* and against the upper fulcrum 1306 may be bent by the plate bender 1300 to decrease the curvature.

Each roller and fulcrum has a surface engageable with the plate that is covered by, and is preferably entirely formed of, a material that does not scratch or mar the plate during the bending operation, which otherwise may affect the fatigue life of the plate. Preferably, the rollers are made with the polymer known as PEEK. The curvature of the rollers and of the fulcra match the radius of the plate to minimize kinking, or incongruities in the plate bending, which also would affect the fatigue life of the plate.

As can be seen in FIG. 66, the arms 1320,1310 include flange portions 1327, 1317 also connected by the pivot pin 1375 and pivotable about the pivot point 1375. Thus, the arms 1320, 1310 and handles 1332, 1331 are joined at the common pivot point 1375. More specifically, the flange portions 1317, 1327 are in a generally facing relationship.

Each flange portion 1317, 1327 has a pair of slots that are aligned with a counterpart of the other flange portion. That is, flange 1317 has a slot 1319 aligned with slot 1329 of the flange 1327, and has a slot 1318 aligned with slot 1328 of the flange 1327. When the arms 1320,1310 and handles 1331, 1332 are joined at the pivot point 1375*a*, the slots 1329 and 1319 are aligned with a key slot 1372*a* of the handle 1331. Similarly, the slots 1328 and 1318 are aligned with a key slot (not shown) of the handle 1332. More specifically, at least a portion of the key slot 1372*a* is aligned with the aligned arm slots 1329, 1319 so that a key 1372 may be received in the key slot 1372*a* and the arm slots 1329, 1319. Moreover, the key 1372 is shiftable from a position where the key 1372 is received in the key slot 1372*a* and only one of the arm slots, such as 1329, to a position where the key 1372 is received the key slot 1372*a* and only the other arm slot 1319.

When the key 1372 is located in the key slot 1372*a* of the handle 1331 and, for instance, the arm slot 1329 of the arm 1320, the handle 1331 and arm 1320 behave as a unitary arm around the pivot point 1375*a*. Alternatively, when the key 1372 is located in the arm slot 1319, the handle 1331 and arm 1310 pivot as a unit. The handle 1332 operates in the same way as described, cooperating with the arm slots 1318 and 1328.

The position of the keys is shifted with selector buttons 1391, 1381, respectively coupled with buttons 1393 and 1383. Representatively, selector button 1393 is secured to a barrel 1394 located in a throughbore 1372*b* of the handle 1331, and the barrel 1394 is then secured to selector button 1391. The throughbore 1372*b* and the key slot 1372*a* are in communication so that a key recess 1394*a* of the barrel 1394 located in the throughbore 1372*b* may be accessed through the key slot 1372*a*. The key 1372 is inserted into the key slot 1372*b* so that a portion is received in the barrel key recess 1394*a* and a portion extends out of the key slot 1372*b* for being received in one of the arm 1310, 1320, as discussed above.

In this manner, movement of one of the selector buttons 1393, 1391 selects which of the arms 1310, 1320 with which the handle 1331 is joined. As an example, shifting the front selector button 1391 inward shifts the barrel 1394 connected thereto through the throughbore 1372*b* in the rearward direction, which causes the other button 1393 to also shift rearward. The shifting of the barrel 1394 also causes the key 1372 to shift in the key slot 1372*a* from the arm slots 1329 to the other arm slot 1319. In this manner, the handle 1331 is disengaged from arm 1320, and is engaged with arm 1310.

In this manner, the handles are cooperatively attached by the described slot-key configuration to one of the arms to form bending levers. With the keys 1372, 1382 in a forward position, the handle 1331 and arm 1320 are connected to form a first opposed bending lever while the other handle 1332 is connected with the other arm 1310 to form a second opposed bending lever. On the other hand, when the keys 1372, 1382 are in a rearward position, the handle 1331 and arm 1310 are connected to form a first crossing bending lever while the other handle 1332 is connected with arm 1320 to form a second crossing bending lever. The bending levers, in any configuration, are connected by the pivot pin 1375 to pivot around pivot point 1375*a*.

When in the configuration with the opposed bending levers (i.e., the keys 1372, 1382 in the forward position), the concave bending roller assemblies 1350*a*, 1350*b* are selectively positioned on the races towards the center of the plate bender 1300 in proximity to the lower fulcrum 1370, as shown in FIG. 63. A plate is then placed between the rollers 1351*a* and 1351*b* and the lower fulcrum 1370 with the top plate surface against the rollers 1351*a*, 1351*b* and the bottom plate surface against the lower fulcrum 1370. As the plate bender 1300 is operated by directing the handles 1331, 1332 inward, the arms 1310, 1320 move downward toward the lower fulcrum 1370 so that the concave rollers 1351*a*, 1351*b* press the plate between the rollers 1351*a*, 1351 and the lower fulcrum 1370. In this manner, the plate is bent over the 1370 fulcrum to increase the curvature.

Conversely, when in the configuration with the crossing bending levers (i.e., the keys 1372,1382 in the rearward position), the convex roller assemblies 1340*a*, 1340*b* are selectively positioned on the races and toward the center of the plate bender 1300 in proximity to the upper fulcrum 1306. A plate is placed between the rollers 1341*a*, 1341*b* and upper fulcrum 1306 so that the top plate surface is against the upper fulcrum 1306 and the bottom plate surface is against the rollers 1341*a*, 1341*b*. Operating the crossing bending levers in a scissors-like fashion by directing the handles 1331, 1332 inward causes the arms 1310, 1320 to move upward toward the upper fulcrum 1370, thereby pressing plate between the convex rollers 1341*a*, 1341*b* and the upper fulcrum 1306. Accordingly, the plate is bent to decrease its curvature.

Figure 37:
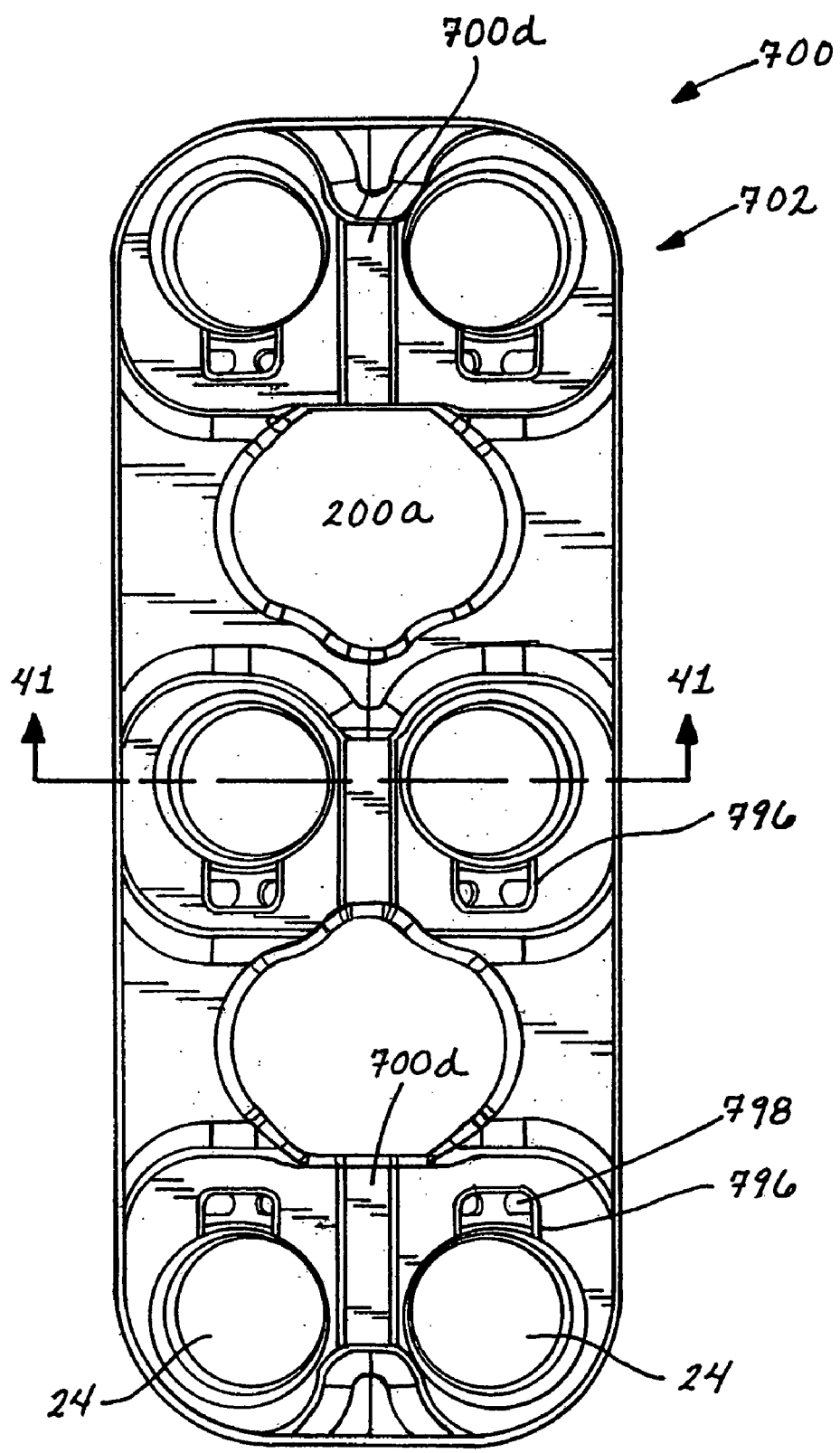
FIG. 37 is a plan view of a further embodiment of a bone plate similar to the bone plate of FIGS. 28-36.
Figure 39:
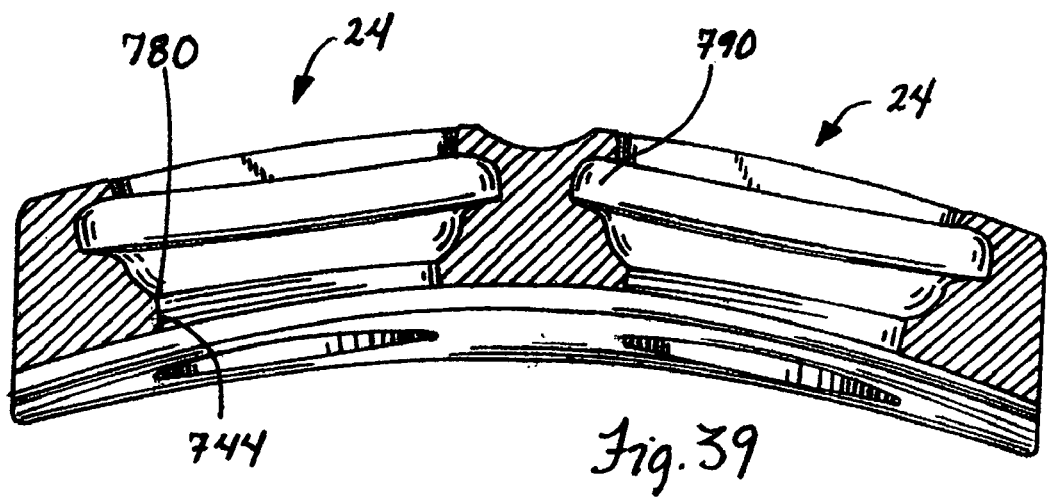
FIG. 39 is a cross-sectional view of the bone plate of FIG. 37 taken through the line 41-41.
Figure 38:
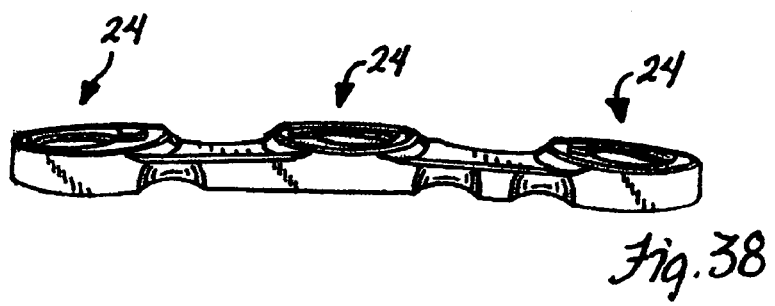
FIG. 38 is a side elevational view of the bone plate of FIG. 37.

Particular features of the bone plates themselves may assist in bending the bone plate. Though these same features may be present in each of the described bone plates, the valleys 20*c* of plate 20, and plate 700 includes valleys 700*d*, as can be seen in FIGS. 28 and 37, on the top surface 700*a* to assist in bending the plate. These are meant to be exemplary only. These valleys 20*c*, 700*d* create stress concentrations to control or predict where the greatest amount of bending takes place, particularly in the event a surgeon chooses to manually adjust the shape of the bone plate.

Once the proper bone plate has been selected and configured with the desired curvature to follow the lordotic curve of the section of the spine to which it is to be secured and to follow the curve of the vertebrae, a plate holder 1400 is used to hold the plate during implantation, and to hold a guide tool 1500 for positioning a pilot hole tool 1600 for creating a pilot hole in the vertebrae for the screws.

As can be seen in FIGS. 67-70, the plate holder 1400 is a scissors or forceps-type instrument having cooperating pivotable arms 1402. The arms 1402 have proximal ends 1404 including finger grips 1405 allowing a surgeon or the like to manipulate the plate holder 1400. The arms 1402 also have distal ends 1406 for connecting to the plate and for receiving the guide tool 1500, as will be described below. The arms 1402 are connected at a pivot point 1403, and, when the proximal ends 1404 are directed towards each other, the distal ends 1406 also move towards each other. The proximal ends 1404 also include opposed ratcheting bars 1408 so that, as the proximal ends 1404 move inwardly, the ratcheting bars 1408 catch each other. In this manner, once the plate holder 1400 is compressed on a plate, the ratcheting bars 1408 retain the position of the arms 1402 in the compressed position. To release the catch of the ratcheting bars 1408, the arms 1402 are simply deformed or flexed slightly in a direction generally orthogonal to the plane of their pivotal movement.

Each of the distal ends 1406 of the arms 1402 includes a guide tool receptor 1420 for receiving the guide tool 1500. The arms 1402 are bent at a point between the pivot point 1403 and the proximal ends 1404, and the guide tool receptors 1420 are attached to a side 1422 of each of the arms 1402 that is opposite the direction of the bend of the arms 1402 so that a surgeon's hand that is manipulating the finger grips 1405 does not obstruct the surgeon's view of the distal ends 1406 or the guide tool receptors 1420.

Figure 44:
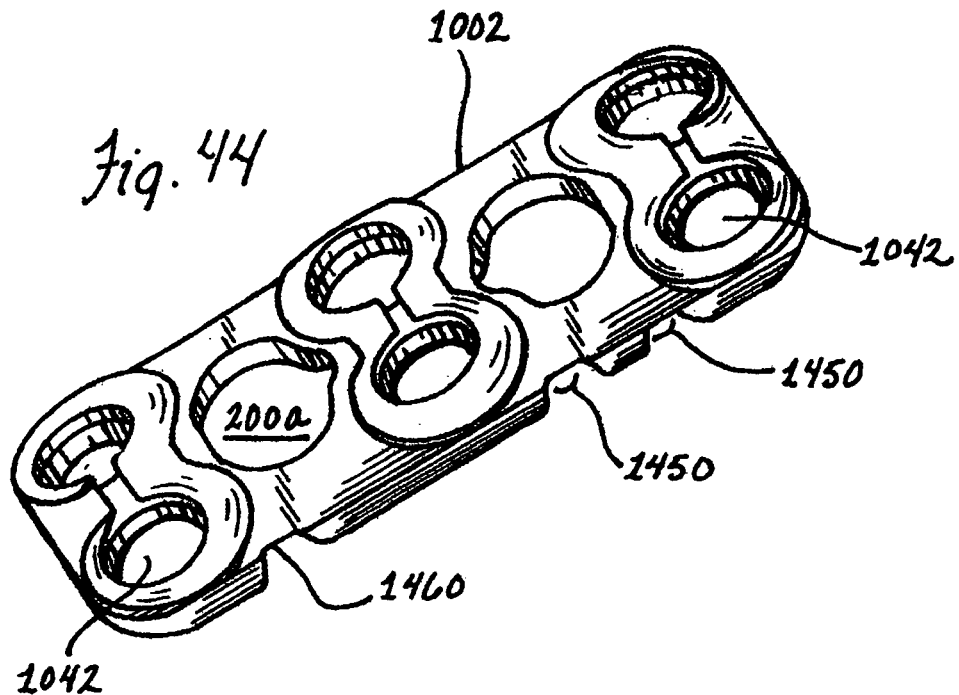
FIG. 44 is a perspective view of a further embodiment of a bone plate.
Figure 46:
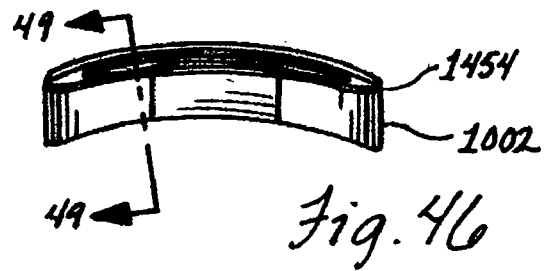
FIG. 46 is an end elevational view of the bone plate of FIG. 44 showing a curvature in the lateral direction.
Figure 47:
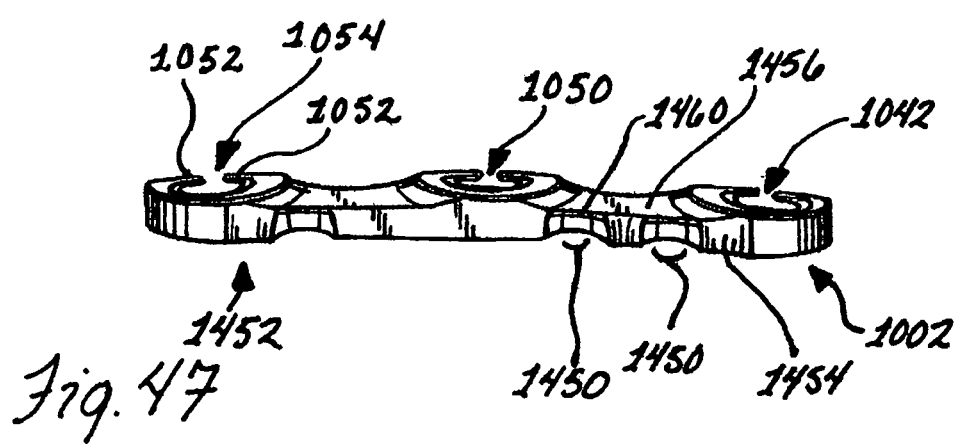
FIG. 47 is a side elevational view of the bone plate of FIG. 44 showing a curvature in the longitudinal direction.
Figure 50:
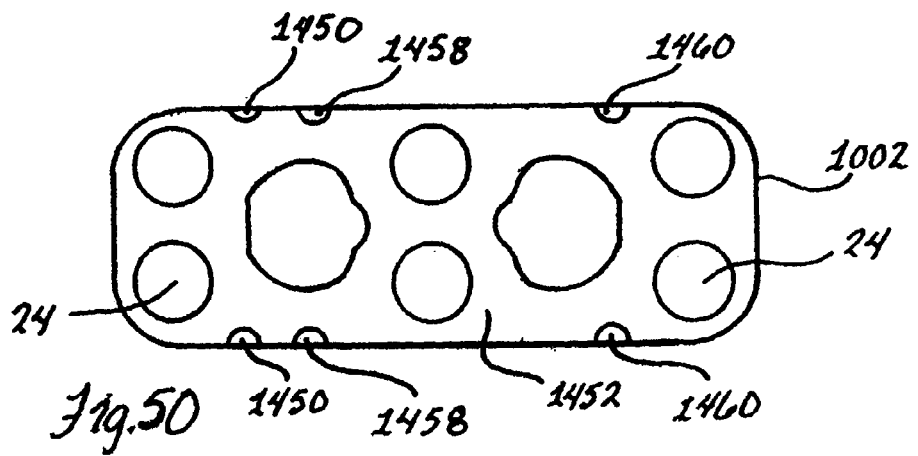
FIG. 50 is a bottom plan view of the bone plate of FIG. 44.

Each of the guide tool receptors 1420 has a bottom surface 1424, and terminal portions 1430 of each arm 1402 include opposed barbs or prongs 1440. As can be seen in FIGS. 44, 47, and 50, the bone plate 1002, as an example, includes recesses 1450 for receiving and cooperating with the prongs 1440. The plate 1002 has a bottom surface 1452 and side edges 1454, and a top surface 1456. The recesses 1450 are formed in pairs, each pair corresponding to a point along the plate 1002 that may receive the opposed prongs 1440 of the plate holder 1400.

The recesses 1450 are generally formed to open to the side edges 1454 and the bottom surface 1452. Accordingly, the recess 1450 has a upper surface 1458 generally facing downward. Thus, a wall 1460 is formed between the upper surface 1458 of the recess 1450 and the top surface 1456 of the plate 1002. The top surface 1456 may be provided with surface marks (not shown) that indicate where the recesses 1450 are located.

Figure 71:
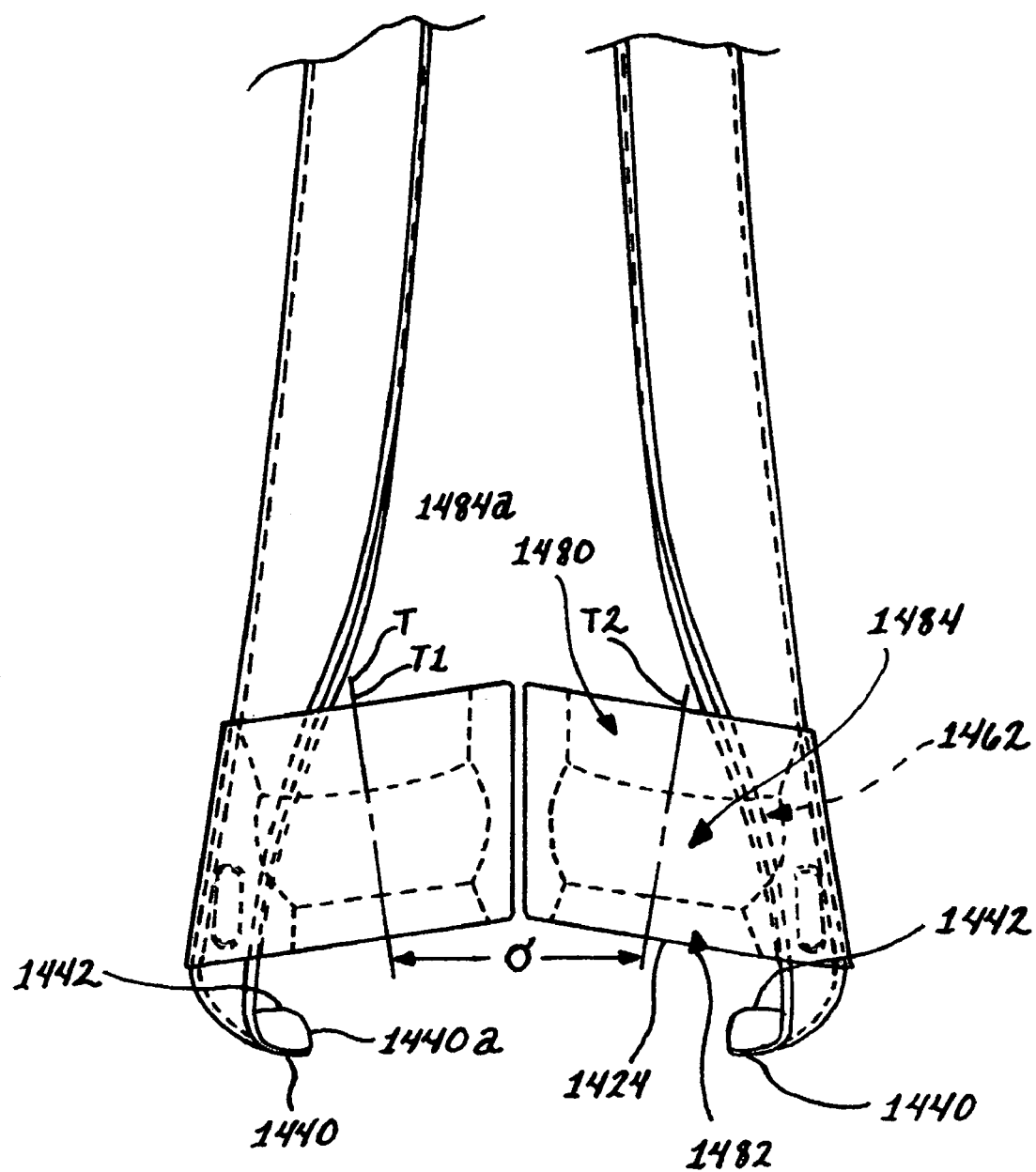
FIG. 71 is a third fragmentary view of a front side of the distal end of the holding tool showing the recess formed therein in phantom.

The recess 1450 has a structure and shape generally corresponding to the shape of the prongs 1440. As can be seen best in FIGS. 69 and 71, each prong 1440 has a curved or arcuate top surface 1442 so as to be hemi-cylindrical. Each prong 1440 also has a tip surface 1444 that may have the edges 1444a rounded for ease of insertion into the recesses 1450.

The plate holder arms 1402 may be pivoted to an open position such that the prongs 1440 are positioned at a distance greater than the lateral width of the plate 1002. The prongs 1440 are then aligned with a selected pair of recesses 1450 corresponding to a pair of bores 24 in the plate 1002. The proximal ends 1404 are then operated to direct the distal ends 1406 towards each other, and the prongs 1440 enter and fit closely within the recesses 1450 in the bone plate 1002.

In order to ensure the plate holder 1400 holds the plate 1002 relatively tightly, portions 1462 of the arms 1402 proximate to the terminal portions 1430 are angled inwardly. This inward angle allows the portions 1462 to cooperate with the prongs 1440 so that the wall 1460 partially defining the recess 1450 is securely held therebetween. Furthermore, the bottom surface 1424 of the guide tool receptors 1420 may contact the bone plate top surface 1456 to constrain any movement between the plate 1002 and the plate holder 1400.

As noted, each guide tool receptor 1420 is configured to receive a guide tool 1500. The guide tool 1500 is used to direct a pilot hole tool 1600 into contact with a point on the vertebrae for forming a pilot hole thereon. As will be discussed below, the pilot hole tool 1600 may be an awl 1620, a drill 1630, or a tap 1640. It should be noted that the term pilot hole, as used herein, may mean a hole formed by compressing bone in a localized area so as to make a recess in which a screw may find purchase, may be a hole formed by a rotating drill tip, or may be a hole formed by a tap such that the hole includes threads therein. The guide tool 1500 may be provided for cooperating with a single guide tool receptor 1420 and pilot hole tool 1600, or may be provided for cooperating with a pair of guide tool receptors 1420 and pilot hole tools 1600.

The guide tool receptor 1420 includes a throughbore 1470 therethrough for receiving the guide tool 1500 and the pilot hole tool 1600 therein. The throughbore 1470 has a central axis T, and the axes T1, T2 of the pair of guide tool receptors 1420 for an included angle σ that is, in the preferred embodiment, 18 degrees. When the plate holder 1400 is secured to a plate, the guide tool receptors 1420 are positioned over and aligned with the bores 24 in the plate.

Each throughbore 1470 includes an upper portion 1480, a lower portion 1482, and a socket 1484 for cooperating with the guide tool 1500. As can be seen in FIGS. 72 and 73, the guide tool 1500 includes a distal end 1502 including a socket portion 1504 for cooperating with the socket 1484 of the guide tool receptor 1420. As will be described below, the guide tool socket portion 1504 is received in the throughbore 1470 so that, in a first form, the guide tool 1500 is fixed thereto and accepts a predetermined orientation so that its central longitudinal axis G is aligned and coincident with the axis T of the throughbore 1470. In a second form, the guide tool 1500 may be received in the throughbore 1470 and be pivotable so that its axis G is offset from the throughbore axis T through a range, such as ±10 degrees in the direction of the longitudinal axis of the plate (cephalad/caudal direction) and ±5 degrees in the lateral direction. In this manner, a pilot hole tool 1600 is received within the guide tool 1500 and may be directed through a fixed guide tool 1500 along the longitudinal axis of the guide tool 1500 and the throughbore 1470, or may be directed through a pivotable guide tool 1500 allowing the surgeon to make a selection as to the angle of entry by the pilot hole tool 1600 into the bone, and, thus, the angle of entry by a screw 22 subsequently inserted therein. The upper portion 1480 of the guide tool receptor socket 1484 is angled radially outward, such as to be frusto-conical, so that the guide tool 1500 may pivot therein, and the lower portion 1482 is also angled radially outward as a frusto-cone so that a pilot hole tool 1600 received within a pivoted guide tool 1500 may pass through the throughbore 1470 to engage the bone at the angle dictated by the guide tool 1500.

The socket portion 1504 of the guide tool 1500 includes a number of finger-like projections 1520 extending in a circular array from a distal end 1522 of a cannula member 1524. The projections 1520 include slot recesses 1526 therebetween so that the projections 1520 may be deflected inwardly. A terminal portion 1528 of each projection 1520 includes an arcuate outer surface portion 1521, and the combination of the portions 1521 combine so that the socket portion 1504 is generally ball-like. The socket 1484 of the guide tool receptor 1420 has an inner surface 1484a that is generally partially spheroidal, and the socket 1484 of the guide tool receptor 1420 and the guide tool socket portion 1504 form a ball-and-socket type connection, though with limited movement, as described above.

To insert the guide tool socket portion 1504 in the socket 1484 of the guide tool receptor 1420, the projections 1520 are compressed or deflected inwardly so that the ball-shape socket portion 1504 is received within the spheroidal socket 1484. Once inserted in the spheroidal socket 1484, the projections 1520 of the guide tool socket portion 1504 are then permitted to deflect outward towards their natural position so that the arcuate surface portions 1521 thereof may contact the spheroidal inner surface 1484*a* to form the ball-and-socket type joint.

The projections 1520 include an angled portion 1540 that angles radially outward from the cannula 1524, increasing towards the distal end 1502. The angled portion 1540 has an edge 1548 at the point of its maximum dimension, which serves to form a shoulder 1549 on the projections generally facing the distal end 1502. A sleeve 1530 is utilized for camming against the angled portion 1540 to deflect the projections inward. The sleeve 1530 is generally cylindrical and has an inner surface 1532, an outer surface 1534, a distal end 1536, and a proximal end 1538. The sleeve 1530 may be reciprocated with respect to the guide tool cannula 1524 so that the inner surface 1532 cams against the angled portion 1540 between a first position in which the projections 1520 in a natural configuration, or are at least minimally deflected inwardly, and a second position in which the projections 1520 are deflected inwardly sufficient to allow the ball shape socket portion 1504 to be received within the socket 1484 of the guide tool receptor 1420. For instance, in the first position the inner surface 1532 at the distal end 1532 may contact a lower portion 1542 of the angled portion 1540. The sleeve 1530 may then be advanced so that the inner surface 1532 cams along the angled portion 1540 of the projections 1520, thereby forcing the projections 1520 inward.

The sleeve proximal end 1538 includes a grip portion 1550 for manual manipulation of the sleeve 1530 relative to the cannula 1524. Near the proximal end 1538, the inner surface 1532 includes an annular shoulder 1552 oriented generally in the distal direction. The cannula 1524 has an inner surface 1554 that also includes an annular shoulder 1556, though the shoulder 1556 is oriented generally towards the proximal end 1538 of the sleeve 1530. The shoulders 1556, 1552 generally face each other, and a spring 1560 or other bias member is positioned between the shoulders 1556, 1552. In this manner, the sleeve 1530 is biased to the first position wherein the projections 1520 are generally undeflected, or are minimally so.

When the sleeve 1530 is advanced, such as by applying manual force to the grip portion 1550 toward the distal end 1536 to deflect the projections 1520 inwardly, the spring 1560 is compressed against its bias. The cannula socket portion 1504 is then inserted and located into the guide tool receptor socket 1484, whereupon the sleeve 1530 may be retracted, such as by releasing the sleeve 1530, by the bias of the spring 1560. The projections 1520 then shift outwardly toward their natural position within the socket 1484.

Whether the guide tool 1500 is a fixed angle or variable angle guide tool 1500 is dependent on the construction of the guide tool 1500 itself. The projections 1520, as stated, include the angled portion 1540 forming a shoulder 1549 generally facing the distal end 1502. The movement of the guide tool 1500 relative to the socket 1484 is dependent on the shoulder 1549. For the fixed guide tool 1500, the projections 1520 assume a predetermined orientation within the socket 1484, and, thus, the guide tool 1500 assumes a predetermined orientation. The variable angle guide tool 1500 may be pivoted with respect to the socket 1484 within a range, such as defined above.

The guide tool 1500 orients and directs a pilot hole tool 1600, as noted above. More specifically, the cannula 1524 of the guide tool 1500 receives and guides the pilot hole tool 1600, as well as limits the depth to which the pilot hole tool 1600 may advance therewithin. As can be seen in FIGS. 77-79, pilot hole tools 1600 in the form of an awl 1620, a drill 1630, and a tap 1640 are each formed as an elongate member having respective chuck or threaded ends 1650, upper shoulders 1660, shanks 1670, lower shoulders 1680, and driving end 1690.

For each of the pilot hole tools 1600, the threaded end 1650 is secured within an instrument for manual or powered operation. Once secured, the pilot hole tool 1600 is inserted into the cannula 1524. As the pilot hole tool 1600 is directed into the bone, the tool 1600 advances further into the cannula 1524. The cannula 1524 has an upper terminal edge 1570, and the tool 1600 may be advanced until the upper shoulder 1660 contacts the terminal edge 1570. Thus, the depth to which the tool 1600 may be driven into the bone is limited by the edge 1570 and the shoulder 1660. In addition, the lower shoulder 1680 is positioned around the tip 1690 so that the tool 1600 may be driven into the bone only to a depth provided by the length of the tip 1690 below the lower shoulder 1680. The lower shoulder 1680 is particularly provided in the event the tool 1600 is used without a guide tool 1500.

Each of the tips 1690 of the respective awl 1620, drill 1630, and tap 1640 is provided with a construction particular to its operation. As depicted, the awl 1620 has a pyramidal-shaped tip 1622 having flat faces that meet in sharp edges, similar to a nail. However, the awl 1620 may, alternatively, have any pointed construction for being driven into bone to create a hole therein. For the awl 1620, the bone may be compressed in the localized region of driving.

The drill 1630 includes a spirally fluted cutting bit 1632, as is depicted. In this manner, the drill 1630 operates in the manner typical of drill bits or tips. As the bit 1632 rotates under pressure, a sharp terminal tip 1634 pierces the bone, and a fluted cutting edge 1636 widens the hole formed by the tip 1634. The spiral configuration of the bit 1632 allows the drill 1630 to draw removed material out of the hole formed thereby.

The tap 1640 is inserted in a pilot hole that has already been made and is used for providing threads in the hole for receiving a screw therein. The tap 1640 has a tip 1642 having threads 1644 along its length to the lower shoulder 1680. A spiral flute 1646 is provided across the threads along the length of the tip 1642 so that each thread 1644 is provided with a leading cutting edge. The threads 1644 may also include an outer sharp edge along their major profile for cutting bone. Accordingly, as the tap 1640 is rotated and advanced into the screw hole, the flute 1646 and threads 1644 cut threads into the bone for the screw.

Figure 80:
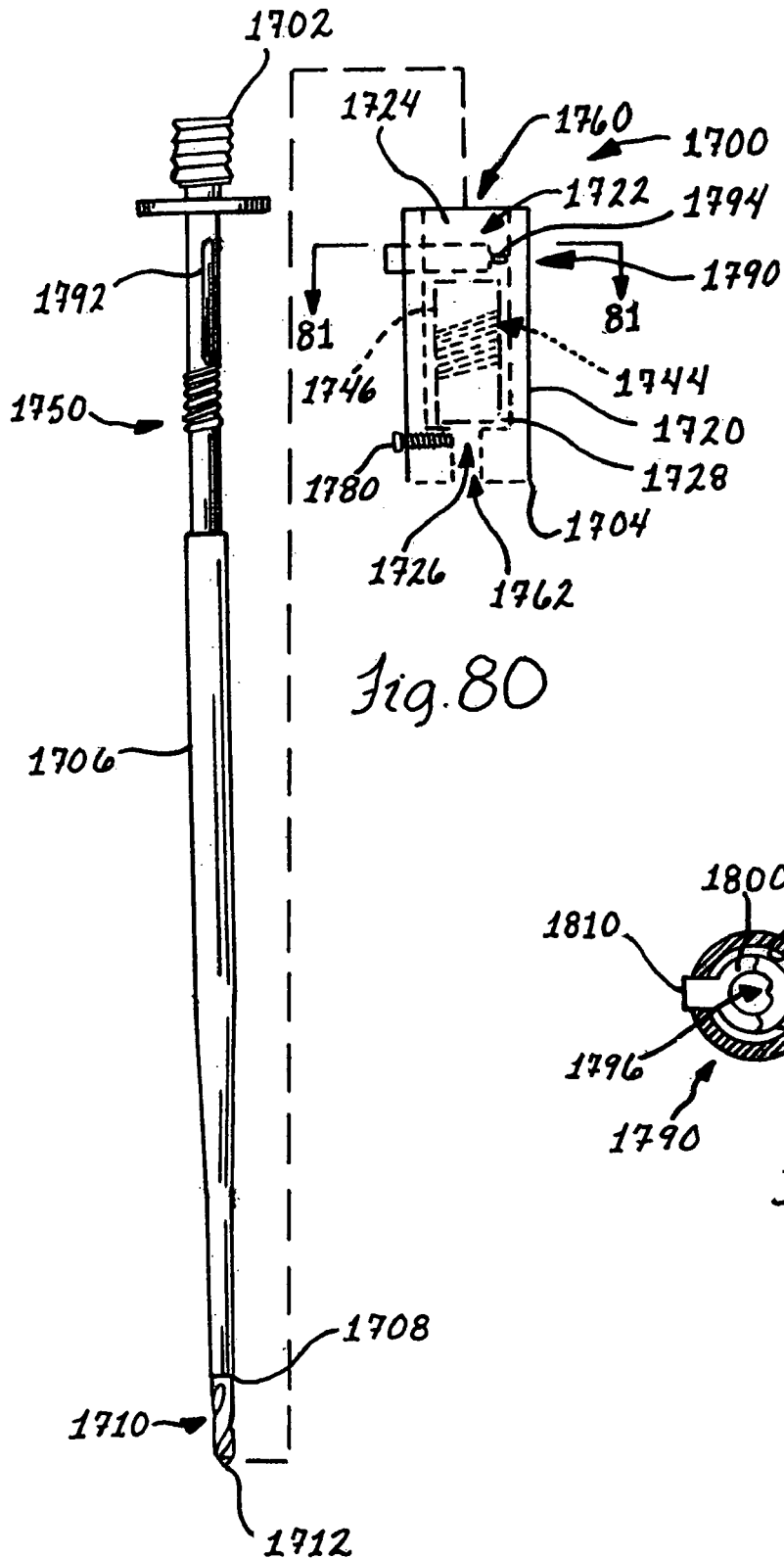
FIG. 80 is a partially exploded view of a variable depth drill, shown without corresponding gripping handle.
Figure 81:
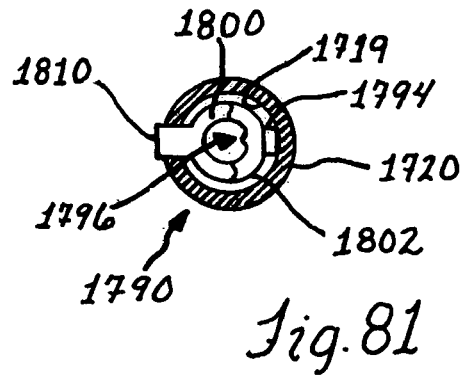
FIG. 81 is top plan view of a position ratchet of the variable depth drill taken through the line 81-81 of FIG. 80.

Referring now to FIG. 80, a variable pilot hole tool 1700 is depicted. As illustrated, the tool 1700 is a variable depth drill, though it may also be a tap, for instance. The variable drill 1700 includes a threaded end 1702, upper shoulder 1704, a shank 1706, a lower shoulder 1708, and a driving end in the form of a fluted drill tip 1710 similar to the drill bit 1620 described above. The drill tip 1710 may be longer than the drill bit 1620 described above so that the lower shoulder 1708 limiting the drilling depth is positioned a greater distance from a drill tip end 1712. The upper shoulder 1704 operates to contact the cannula upper edge 1570 when the drill 1700 has been advanced within the cannula 1524 to the desired depth.

However, for the variable drill tool 1700, the upper shoulder 1704 may be selectively positioned along a portion of the shank 1706. The upper shoulder 1704 is located on a housing 1720 that is, preferably, generally cylindrical. The housing 1720 has an inner cylindrical cavity 1722 including an upper portion 1724 and a lower portion 1726. The lower portion 1726 has a reduced diameter in comparison to the diameter of the upper portion 1724. Accordingly, a shoulder 1728 is formed between the upper and lower portions 1724, 1726.

The upper portion 1724 includes an interior surface having a threaded portion 1744. Alternatively, a threaded nut 1746 may be inserted within the upper portion 1724 and have a threaded interior surface.

The shank 1706 is received within and through the housing 1720. More specifically, the shank 1706 passes through a top opening 1760 and a bottom opening 1762 so that the threaded end 1702 is positioned above the top opening 1760 and the tip 1710 is positioned below bottom opening 1762. The shank 1706 includes an externally threaded portion 1750 so that the shank 1706 may be threaded into the threads 1744 of the housing 1720. In order to vary the depth of the variable drill tool 1700, the shank 1706 is rotated relative to the housing 1720 so that the threads 1744, 1750 therebetween cooperate to advance or retract the shank 1706 with respect to the housing 1720, thereby altering the amount of the shank 1706 extending below the bottom opening 1762. As the bottom opening 1762 is aligned with the upper shoulder 1704, the amount of shank 1706 that may be received in and through the guide tool 1500 is adjusted by the rotation of the shank 1706 along the threads 1744 of the housing 1720. A set screw 1780 is provided for extending through the housing 1720 and into the lower cavity portion 1726 and, when advanced thereinto, the set screw 1780 contacts the shank 1706 to prevent movement of the shank 1706 relative to the housing 1720.

The housing 1720 further includes a limiter 1790 for controlling the rotation of the shank 1706 relative to the housing 1720. Specifically, the shank 1706 includes one or more grooves 1792 or recesses, and the limiter 1790 cooperates with the groove 1792 to regulate the relative rotation between the housing 1720 and the shank 1706. The limiter 1790 is fixed within the housing 1720 and includes a bias member 1794 that biases a protrusion in the form of a V-tab 1796 into engagement with the spline recess 1972. In the present embodiment, a single groove 1792 is provided, such that the V-tab 1796 engages the groove 1792 once for each rotation. In this manner, advancement of the shank 1706 relative to the housing 1720 is presented with discrete stops.

The V-tab 1796 is preferably biased into engagement with the groove 1792 by a bias member in the form of a spring 1794. In the event the spring 1794 has a relatively low spring constant, rotation of the shank 1706 will cause the V-tab to cam out of engagement in the groove 1792. If the spring 1794 is relatively stiff, the V-tab 1796 does not allow rotation of the shank 1706 relative to the housing 1720.

To allow the shank 1706 to rotate relative to the housing 1720 when the spring 1794 is relatively stiff, the V-tab 1796 is manually released. The V-tab 1796 is secured on an inner surface 1798 of a limiter ring 1800. The spring 1794 biases the limiter ring 1800 so that the V-tab 1796 engages the groove 1792. To do so, the spring 1974 is located between an outer surface 1802 of the limiter ring 1800 and the interior 1719 of the housing 1720. The V-tab 1796 is manually released by forcing the limiter ring 1800 against the bias of the spring 1794.

An actuator button 1810 is provided for disengaging the groove 1792 and V-tab 1796. The actuator button 1810 extending outward from the limiter ring 1800 and out through the housing 1720. By depressing the actuator button 1810 into the housing 1720, the limiter ring 1800 is shifted against the spring 1794, thereby shifting the V-tab 1796 out of the groove 1792. In this manner, the shank 1706 may then be rotated for being advanced or retracted relative to the housing 1720 and for adjusting the depth the drill permitted into the bone. The variable drill 1700 may be inserted into the guide tool 1500, and a depth gage (not shown) may be used to confirm the proper drill depth.

As described, after resecting surrounding tissue from the implant site, the sizing caliper 1200 may be used to determine the proper plate size. The plate is selected based on dynamized bores, non-dynamized bores, or a combination. The plate bender 1300 is used if it is desired to alter the curvatures of the plate. The types of screws 22 are selected, whether they be fixed or variable angle (polyaxial) screws, and whether they be self-drilling, self-tapping, or neither so that a tap is minimally required. The plate is then grasped by the plate holder 1400 and positioned in the desired location on the vertebrae. A guide tool 1500 is selected to be either fixed or variable, and then inserted into the guide tool receptors 1420 of the plate holder 1400. A self-drilling screw may be driven through the guide tool 1500 into the bone, or one or more pilot hole tools 1600 may be likewise used.

In the event a pilot hole tool 1600 is used, a temporary holding pin 1850 (FIG. 76) may be inserted through the guide tool 1500 to secure a hole made in the bone, or to create a hole in the bone. The temporary holding pin 1850 has a threaded shank 1852, and an enlarged head height 1854 so that the pin 1850 is clearly noticed as being temporary. In this manner, the plate may be secured so that the surgeon may address prepping other bone holes and driving screws through the other bores of the bone plate.

A preferred sequence of inserting screws in the bores of the plate is presented. Each screw should not be completely tightened until all are partially secured. After a first bore has received a screw, the bore diagonal thereto receives the next screw. Next, the third bore to receive a screw is the bore on the same vertebrae as the first bore receives a screw. The fourth bore is diagonal to the third bore. Any intermediate bores may then receive screws. Once all the screws are in place, they should be tightened in the same order. To remove the screws, the extractor 1900 may be used in conjunction with the extractor 1900.

While the invention has been described with respect to specific examples including presently preferred modes of carrying out the invention, those skilled in the art will appreciate that there are numerous variations and permutations of the above described systems and techniques that fall within the spirit and scope of the invention.

We claim:

1. A device for stabilization of adjacent vertebrae of a spine, the device comprising:
    a rigid bone plate having a rigid plate body with an elongate configuration including a longitudinal axis;
    a plurality of bone anchor members each having an enlarged head and a shank depending therefrom;
    a plurality of aligned bores in the rigid bone plate body extending therethrough with the bores generally aligned along the longitudinal axis and being configured for receiving the bone anchor members therethrough;
    at least one upper dynamized bore of the aligned plurality of bores that is elongated along the longitudinal axis with an upper one of the bone anchor members extending therethrough for being driven into an upper vertebra to allow relative longitudinal movement between the upper bone anchor member and the upper dynamized bore with the upper bone anchor member extending through the upper dynamized bore and driven into the upper vertebra;
    at least one lower dynamized bore of the aligned plurality of bores that is elongated along the longitudinal axis with a lower one of the bone anchor members extending therethrough for being driven into a lower vertebra to allow relative longitudinal movement between the lower bone anchor member and the lower dynamized bore with the lower bone anchor member extending through the lower dynamized bore and driven into the lower vertebra;

at least one intermediate non-dynamized bore of the plurality of aligned bores that is aligned between the upper and lower elongated bores along the longitudinal axis with an intermediate one of the bone anchor members extending therethrough for being driven into an intermediate vertebra between the upper and lower vertebrae, the intermediate non-dynamized bore being configured to fix the bone anchor member extending therethrough and the intermediate vertebra against longitudinal movement relative to the plate with the elongated upper and lower dynamized bores permitting movement of the associated anchor member extending therethrough and the respective upper and lower vertebrae relative to the plate;

a lower, curved surface of each of the heads of the bone anchor members; and a curved seating surface in each of the bores against which the lower, curved surface of the bone anchor members engage with the curved, seating surfaces in the upper and lower dynamized bores having a radius of curvature greater than that of the lower, curved surface of the heads of the bone anchor members to allow for the relative longitudinal movement between the bone anchor members and the upper and lower dynamized bores.

2. The device of claim 1 wherein the bone plate has top and bottom surfaces, and the bone plate has a uniform thickness between the top and bottom surfaces thereof that is the same at each of the upper, lower and intermediate bores of the plate.

3. The device of claim 1 wherein the plate has parallel sides that extend along the longitudinal axis of the rigid plate body, the parallel sides defining a constant width of the plate body to minimize torsional bending of the plate about the longitudinal axis.

4. The device of claim 1 wherein the bone plate includes a plurality of viewing windows with each viewing window located longitudinally between the bores for adjacent vertebrae, and at least one of the viewing windows having an edge extending substantially perpendicular to the longitudinal axis of the plate to permit alignment of the window edge with an edge of an adjacent vertebra.

5. The device of claim 1 in combination with the bone anchor members, the elongated upper and lower dynamized bores each having an upper end and a lower end, with the upper bone anchor member extending through the upper dynamized bore positioned at the upper end thereof and the lower bone anchor member extending through the lower dynamized bore positioned at the lower end thereof and driven into the lower vertebrae so that the upper and lower bone anchor members are limited to moving toward the intermediate bore upon compressive loading of the vertebrae.

6. The device of claim 1 including at least one intermediate dynamized bore longitudinally between the intermediate non-dynamized bore and one of the upper and lower dynamized bores.

7. The device of claim 6 wherein the one of the upper and lower dynamized bores has a predetermined length along the longitudinal axis that is greater than that of the intermediate dynamized bore.

8. The device of claim 1 wherein the upper, lower and intermediate bore comprise a pair of upper bores, a pair of intermediate bores, and a pair of lower bores.

9. The device of claim 8 wherein the pairs of upper, lower and intermediate bores form two aligned columns extending along the longitudinal axis.

10. The device of claim 8 wherein the bone plate includes a plurality of viewing windows each located longitudinally between the pairs of bores for adjacent vertebrae, at least one of the windows having a projecting portion that extends along the longitudinal axis toward an area between one of the pairs of bores to allow a surgeon to view the vertebrae for securing the bone plate thereto.

11. The device of claim 1 wherein the rigid body of the rigid bone plate is of one of a titanium, stainless steel, and PEEK material.

12. The device of claim 1 wherein the bone plate has top and bottom surfaces; and a resilient retainer within at least one of the dynamized bores between the top and bottom surfaces of the bone plate, the retainer having a pass-through position wherein the retainer is resiliently deformed so that the corresponding bone anchor member may be inserted or removed from the dynamized bore, and a retention position wherein the retainer partially intersects the dynamized bore and is located above the head of the bone anchor member inserted therein.

13. The device of claim 1 wherein the at least one intermediate non-dynamized bore comprises a pair of intermediate non-dynamized bores;

a resilient retainer within both of the pair of intermediate bores, the resilient retainer having a pass-through position wherein the retainer is resiliently deformed so that the corresponding bone anchor may be inserted or removed from at least one of the intermediate bores, and a retention position wherein the retainer partially intersects at least one of the intermediate bores and is located above the head of the bone anchor member inserted therein;

a connecting span of the resilient retainer extending transversely to the longitudinal axis of the bone plate; and a pair of arms of the resilient retainer, each of the pair of arms being disposed within one of the pair of intermediate bores and deflecting away from the connecting span when the retainer is resiliently deformed to the pass-through position thereof.

14. A device for stabilization of adjacent vertebrae of a spine, the device comprising:

a bone plate having a top and a bottom surface, and an elongate configuration including a generally longitudinal axis;

a plurality of bores that extend between the top and bottom surfaces of the bone plate along bore axes that extend generally normal to the top surface of the bone plate;

a plurality of bone anchors each configured for extending through a respective bore, the bone anchors each having a drive head including a top surface thereof and a shank depending from the drive head;

curved engagement surfaces of the bores and the drive heads of the bone anchors that are adapted to engage each other with the bone anchors driven through the bores into the vertebrae therebelow and which are configured to allow for the pivoting of the drive heads in the bores with the curved engagement surfaces engaging each other;

at least one bore of the plurality of bores that is elongated along the longitudinal axis of the bone plate, the elongated bore having a predetermined length that permits the bone anchor extending therethrough to translate along the length of the bore relative to the bone plate;

a resilient retainer for resisting bone anchor back-out positioned within the elongated bore between the top and bottom surfaces of the bone plate, the retainer having a pass-through position wherein the retainer is resiliently deformed so that the bone anchor may be inserted or removed from the elongated bore, and a retention position wherein the retainer partially intersects the elongated bore and is located above the top surface of the bone anchor drive head;

a pair of spaced, straight portions of the retainer extending substantially parallel to each other and the bone plate longitudinal axis along the length of the elongated bore with the bore configured so that the pair of retainer straight portions are completely exposed in the bore in the retention position of the retainer such that no portion of the bone anchor drive head extends above either of the retainer straight portions and no portion of the bone plate overhangs either of the retainer straight portions a predetermined axial gap spacing between the top surface of the bone anchor drive head and both of the retainer straight portions along the bore axis with the bone anchor shank extending parallel to the bore axis with the axial gap spacing sized to allow for polyaxial driving of the bone anchor transverse to the bore axis into a vertebra with a predetermined amount of pivoting of the bone anchor shank from the bore axis allowed via the curved engagement surfaces of the bore and the drive head of the bone anchor before the bone anchor top surface engages at least one of the retainer straight portions.

15. The device of claim 14 wherein the bone anchor drive head has a predetermined axial height that is substantially greater than the predetermined axial gap spacing.

16. The device of claim 15 wherein the plate has a predetermined thickness that is approximately two times as great as the predetermined axial height of the bone anchor drive head.

17. The device of claim 14 wherein the plate has an inner surface that extends between the top and bottom surfaces of the bone plate about the elongated bore, the inner surface including the engagement surface of the bore and a laterally recessed pocket therein above the engagement surface which permits the straight portions of the resilient retainer exposed in the bore to be deformed therein when the retainer is resiliently deformed to the pass-through position thereof.

* * * * *

UNITED STATES PATENT AND TRADEMARK OFFICE
CERTIFICATE OF CORRECTION

PATENT NO. : 7,740,649 B2
APPLICATION NO. : 10/973891
DATED : June 22, 2010
INVENTOR(S) : Lawrence Mosca et al.

It is certified that error appears in the above-identified patent and that said Letters Patent is hereby corrected as shown below:

In the Claims

In claim 14, column 37, line 15, after "portions" insert --; and--.

Signed and Sealed this
Twentieth Day of August, 2013

Teresa Stanek Rea
*Acting Director of the United States Patent and Trademark Office*